US010301614B2

(12) United States Patent
Duchateau et al.

(10) Patent No.: US 10,301,614 B2
(45) Date of Patent: May 28, 2019

(54) METHOD TO OVERCOME DNA CHEMICAL MODIFICATIONS SENSITIVITY OF ENGINEERED TALE DNA BINDING DOMAINS

(71) Applicant: CELLECTIS, S.A., Paris (FR)

(72) Inventors: Philippe Duchateau, Draveil (FR); Julien Valton, Charenton le Pont (FR)

(73) Assignee: CELLECTIS, Paris (FR)

( * ) Notice: Subject to any disclaimer, the term of this patent is extended or adjusted under 35 U.S.C. 154(b) by 554 days.

(21) Appl. No.: 14/387,162

(22) PCT Filed: Mar. 15, 2013

(86) PCT No.: PCT/IB2013/000721
§ 371 (c)(1),
(2) Date: Sep. 22, 2014

(87) PCT Pub. No.: WO2013/140250
PCT Pub. Date: Sep. 26, 2013

(65) Prior Publication Data
US 2015/0037809 A1 Feb. 5, 2015

Related U.S. Application Data

(60) Provisional application No. 61/615,011, filed on Mar. 23, 2012, provisional application No. 61/674,083, filed on Jul. 20, 2012.

(51) Int. Cl.
C12N 15/10 (2006.01)
G01N 33/53 (2006.01)
C07K 14/47 (2006.01)
C12N 9/22 (2006.01)

(52) U.S. Cl.
CPC ............ C12N 15/102 (2013.01); C07K 14/47 (2013.01); C12N 9/22 (2013.01); G01N 33/5308 (2013.01); C07K 2319/61 (2013.01); C07K 2319/80 (2013.01)

(58) Field of Classification Search
CPC .... C12N 15/102; C12N 9/22; G01N 33/5308; C07K 14/47; C07K 2319/80; C07K 2319/61
USPC ......................... 435/188, 6.19, 455; 530/350
See application file for complete search history.

(56) References Cited

U.S. PATENT DOCUMENTS

2011/0145940 A1 6/2011 Voytas et al.
2011/0239315 A1* 9/2011 Bonas ................ C12N 15/1034
800/13

FOREIGN PATENT DOCUMENTS

EP 2 206 723 A1 7/2010
WO 2012/158986 A2 11/2012

OTHER PUBLICATIONS

Deng et al. (Feb. 10, 2012) Science, vol. 335, 720-723.*
Bultmann et al. (2012) Nucleic Acids Research, vol. 40(12), 5368-5377 (published online Mar. 2, 2012).*
Baker, M., "Gene Editing Nucleases", Nature Methods (2012), vol. 9:1, pp. 23-27.
Bogdanove, A., et al., "TAL Effectors: Customizable Proteins for DNA Targeting", Science (2011), vol. 333, pp. 1843-1846.
Daboussi, F., et al., "Chromosomal Context and Epigenetic Mechanisms Control the Efficacy of Genome Editing by Rare-Cutting Designer Endonucleases" NAR (2012), vol. 40:13, pp. 6367-6379.
Grizot, S., et al., "Efficient Targeting of a SCID Gene by an Engineered Single-Chain Homing Endonuclease", NAR (2009), vol. 37:16, pp. 5405-5419.
Grizot, S., et al., "Generation of Redesigned Homing Endonucleases Comprising DNA-Binding Domains Derived from Two Different Scaffolds", NAR (2010), vol. 38:6, pp. 2006-2018.
Jaenisch, R., et al., "Epigenetic Regulation of Gene Expression: How the Genome Integrates Intrinsic and Environmental Signals", Nature Genetics Supplement (2003), vol. 33, pp. 245-254.
Li, T., et al., "Modularly Assembled Designer TAL Effector Nucleases for Targeted Gene Knockout and Gene Replacement in Eukaryotes", NAR (2011), vol. 39:14, pp. 6315-6325.
Reyon, D., et al., "FLASH Assembly of TALENs Enables High-Throughput Genome Editing", Nat. Biotechnol. (2012), vol. 30:5, pp. 460-465.
Ziller, M., et al., "Genomic Distribution and Inter-Sample Variation of Non-CpG Methylation Across Human Cell Types", PLoS Genetics (2011), vol. 7:12, (www.plosgenetics.org—e1002389), 15 pgs.
Arnould, S., et al., "Engineering of Large Numbers of Highly Specific Homing Endonucleases that Induce Recombination on Novel DNA Targets.", JMB (2005), vol. 355, pp. 443-458.
Boch, J. et al., "Breaking the Code of DNA Binding Specificity of TAL-Type III Effectors.", Science (2009), vol. 326, pp. 1509-1512.
Bogdanove, A. et al., "TAL Effectors: Finding Plant Genes for Disease and Defense", COPB (2010), vol. 13, pp. 394-401.
Chames, P. et al., "In Vivo Selection of Engineered Homing Endonucleases Using Double-Strand Break Induced Homologous Recombination", NAR (2005), vol. 33:20, pp. e178, 10 pgs.
Wei, C. et al., "TALEN or Cas9—Rapid, Efficient and Specific Choices for Genome Modifications" JGG (2013), vol. 40, pp. 281-289.
Epinat, J. et al., "A Novel Engineered Meganuclease Induces Homologous Recombination in Yeast and Mammalian Cells", NAR (2003), vol. 31:11, pp. 2952-2962.

(Continued)

Primary Examiner — Anne Marie S Wehbe
(74) Attorney, Agent, or Firm — Arrigo, Lee, Guttman & Mouta-Bellum LLP

(57) ABSTRACT

The present invention relates to polypeptides and more particularly to Transcription Activator-Like Effector derived proteins that allow to efficiently target and/or process nucleic acids. Particularly, the present invention reports the characterization of TALE derived proteins that can efficiently target methylated DNA. The present invention more specifically relates to TALE derived proteins that allow activation of methylated promoters responsible for gene silencing.

Figure 1:
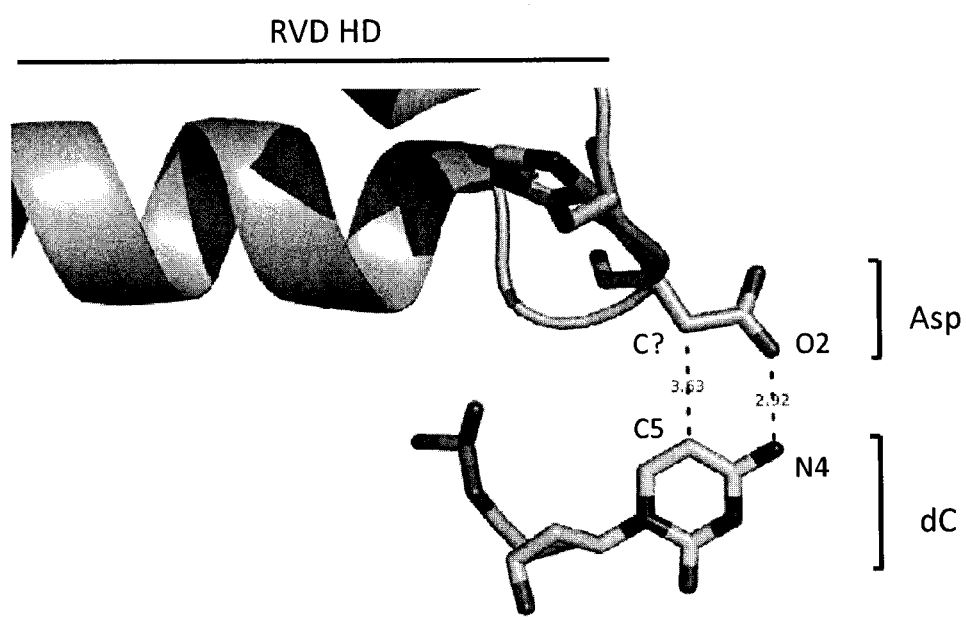

16 Claims, 9 Drawing Sheets
Specification includes a Sequence Listing.

(56) References Cited

OTHER PUBLICATIONS

Huang, P. et al., "Heritable Gene Targeting in Zebrafish Using Customized TALENs", Nat. Biotech. (2011), vol. 29:8, pp. 699-700.
Li, T. et al., "Tal Nucleases (TALNs): Hydrid Proteins Composed of TAL Effectors and FokI DNA-Cleavage Domain", NAR (2011), vol. 39:1, pp. 359-372.
Mahfouz, M. M. et al., "De Novo-Engineered Transcription Activator-Like Effector (TALE) Hybrid Nuclease With Novel DNA Binding Specificity Creates Double-Strand Breaks", PNAS (2011), vol. 108:6, pp. 2623-2628.
Mak, A. et al., "The Crystal Structure of TAL Effector PthX01 Bound to Its DNA Target", Science (2012), vol. 335, pp. 716-719.
Miller, J. et al., "A TALE Nuclease Architecture for Efficient Genome Editing", Nat. Biotech. (2011), vol. 29:2, pp. 143-148.
Morbitzer, R. et al., "Assembly of Custom TALE-Type DNA Binding Domains by Modular Cloning", NAR (2011), vol. 39:13, pp. 5790-5799.
Moscou, M. et al., "A Simple Cipher Governs DNA Recognition by TAL Effectors", Science (2009), vol. 326, p. 1501.
Mussolino, C. et al., "A Novel TALE Nuclease Scaffold Enables High Genome Editing Activity in Combination With Low Toxicity", NAR (2011), vol. 39:21, pp. 9283-9293.
Mussolino, C. et al., "TALE nucleases: tailored genome engineering made easy", Curr. Opin. Biotech (2012), vol. 23, pp. 644-650.
Sander, J. et al., "Targeted Gene Disruption in Somatic Zebrafish Cells Using Engineered TALENs", Nat. Biotech. (2011), vol. 29:8, pp. 697-698.
Scholze, H. et al., "TAL effectors are remote controls for gene activation" Curr. Opin. Microbio. (2011), vol. 14, pp. 47-53.
Smith, J. et al., "A Combinatorial Approach to Create Artificial Homing Endonucleases Cleaving Chosen Sequences", NAR (2006), vol. 34:22, e149, 12 pgs.
Streubel, J. et al., "TAL Effector RVD Specificities and Efficiencies", Nat. Biotech. (2012), vol. 10:7, pp. 393-395.
Weber, E. et al., "Assembly of Designer TAL Effectors by Golden Gate Cloning", PLos One (2011), vol. 6:5, e19722, 5 pgs.
Zhang, F. et al., "Efficient Construction of Sequence-Specific TAL Effectors for Modulating Mammalian Transcription", Nat. Bitotech. (2011), vol. 29:2, pp. 149-153.

* cited by examiner

A xpc1 locus

<u>Left target</u>   Spacer

TCCGAGATGTCACACAG AGGTACGACCC AGTCTGGATGACAGTGA
AGGCACTACAGTGTGTC TCCATGCTGGG TCAGACCTACTGTCACT

<span style="text-decoration: overline">                Right target                </span>

B

XPCT1L_HD
HD-HD-NN-NI-NN-NI-NG-NN-NG-HD-NI-HD-NI-HD-NI-NG#

XPCT1L_N*
HD-N*-NN-NI-NN-NI-NG-NN-NG-HD-NI-HD-NI-HD-NI-NG#

XPCT1R
HD-NI-HD-NG-NN-NG-HD-NI-NG-HD-HD-NI-NN-NI-HD-NG#

Figure 3

METHOD TO OVERCOME DNA CHEMICAL MODIFICATIONS SENSITIVITY OF ENGINEERED TALE DNA BINDING DOMAINS

FIELD OF THE INVENTION

The present invention relates to polypeptides and more particularly to Transcription Activator-Like Effector derived proteins that allow to efficiently target and/or process nucleic acids. Particularly, the present invention reports the characterization of TALE derived proteins that can efficiently target methylated DNA. The present invention more specifically relates to TALE derived proteins that allow activation of methylated promoters responsible for gene silencing. The present invention also concerns methods to use these proteins. The present invention also relates to vectors, compositions and kits in which Repeat Variable Diresidue (RVD) domains and Transcription Activator-Like Effector (TALE) proteins of the present invention are used.

BACKGROUND OF THE INVENTION

Transcription activator-like effectors (TALEs), a group of bacterial plant pathogen proteins have recently emerged as new engineerable scaffolds for production of tailored DNA binding domains with chosen specificities (1, 2). TALE DNA binding domain is composed by a variable number of 33-35 amino acid repeat modules. These repeat modules are nearly identical to each other except for two variable amino acids located at positions 12 and 13 (i.e. Repeat Variable Di residues, RVD). The nature of residues 12 and 13 determines base preferences of individual repeat module. Moscou M. J and Bogdanove A. J and Boch et al. described the following code: HD for recognizing C; NG for recognizing T; NI for recognizing A; NN for recognizing G or A; NS for recognizing A or C or G or T; HG for recognizing T; IG for recognizing T; NK for recognizing G; HA for recognizing C; ND for recognizing C; HI for recognizing C; HN for recognizing G; NA for recognizing G; SN for recognizing G or A; and YG for recognizing T (International PCT Applications WO 2011/072246 and 3, 4). This remarkably simple cipher, consisting in a one-repeat-to-one-base pair code, allowed for prediction of TAL effector binding site and more importantly for construction of custom TAL effector repeat domains that could be tailored to bind DNA sequence of interest. This unprecedented feature unmasked exciting perspectives to develop new molecular tools for targeted genome applications and within the past two years, TALE-derived proteins have been fused to transcription activator/repressor or nuclease domains and successfully used to specifically regulate transcription of chosen genes (5) or to perform targeted gene modifications and insertions (6-9).

Critical to the efficiency of engineered TALE-derived proteins is their ability to access and efficiently bind their chromosomal target sites. Numerous factors may hinder binding, including DNA packaging into chromatin, position of nucleosomal proteins with respect to the target site and chemical DNA modifications such as methylation. In higher eukaryotes, DNA methylation is involved in the regulation of genes expression and predominantly occurs at the C5 position of cytosine found in the dinucleotide sequence CpG (10) and also CpA, CpT and CpC (11). The presence of such additional methyl moiety may hinder recognition of modified cytosine by RVD HD that is commonly used to target cytosine. This feature may represent an important epigenetic drawback for genome engineering applications using TALE-derived proteins.

There remains a need for designing new RVDs, repeat sequences and TALE derived proteins comprising RVDs to overcome chemical DNA modifications and to efficiently detect, target and process nucleic acids comprising these chemical modifications.

Unexpectedly, the inventors have found as part of their laboratory intensive research that shorter TAL repeats including a gap at the level of amino acid positions 12 and/or 13 (which could be regarded as forming "incomplete RVDs") can better accommodate chemically modified nucleic acid bases in particular methylated bases. Based on this finding, they have synthetized TALEs that can efficiently target methylated target nucleic acid sequences, and more generally chemically modified bases, as a way to overcome the above limitations of current TALE-derived proteins.

BRIEF SUMMARY OF THE INVENTION

In a general aspect, the present invention relates to polypeptides that allow to efficiently detect, target and/or process nucleic acids comprising chemical modifications. More particularly, the present invention reports the characterization of TALE derived protein sensitivity to chemical modifications such as cytosine methylation and presents an efficient method to overcome such sensitivity. This method relies on the utilization of RVDs "star", which means incomplete RVDs including a gap symbolized by "*" to accommodate chemically modified nucleic acid base within a nucleic acid target sequence. This gap is revealed when the TAL repeat is aligned using ClustalW alignment with other standard di-residues. The invention more particularly relies on the inclusion of the RVDs N* and H* or **, in TALE repeat domains to specifically target methylated bases, especially 5-methyl-cytosine. The present invention also concerns methods to use Transcription Activator-Like Effector proteins comprising such RVDs. The present invention also relates to vectors, compositions and kits in which RVDs and Transcription Activator-Like Effector proteins of the present invention are used.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Close up structure of the eighth RVD HD of PthXo1 Tal repeat domain interacting with the eighth deoxycytidine of its cognate target (12). Distances between deoxycytidine C5 and aspartate Cβ and hydrogen bond between deoxycytidine N4 and aspartate O2 are indicated with dashed lines.

Figure 2:
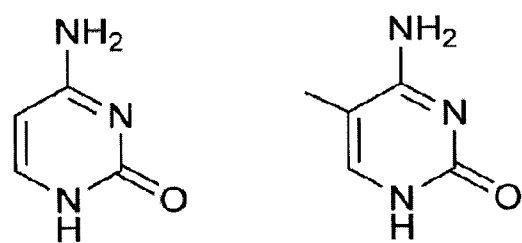

FIG. 2: Chemical structures of cytosine, 5-methyl-cytosine.

FIG. 3: Description of XPCT1_HD and XPCT1_N* TALE-nucleases. A. Description of xpc1 locus target. B. sequences of XPCT1L_HD, XPCT1L_N* and XPCT1R TAL repeat arrays used to generate XPCT1_HD and XPCT1_N* TALE-nucleases. "T" as the first nucleotide of the target DNA sequence (5' to 3') is recognized and bound by "RVD0" repeat, named for a postulated $0^{th}$ repeat (16) at the C-terminus extremity of the N-terminal domain of a natural TALE.

Figure 4:
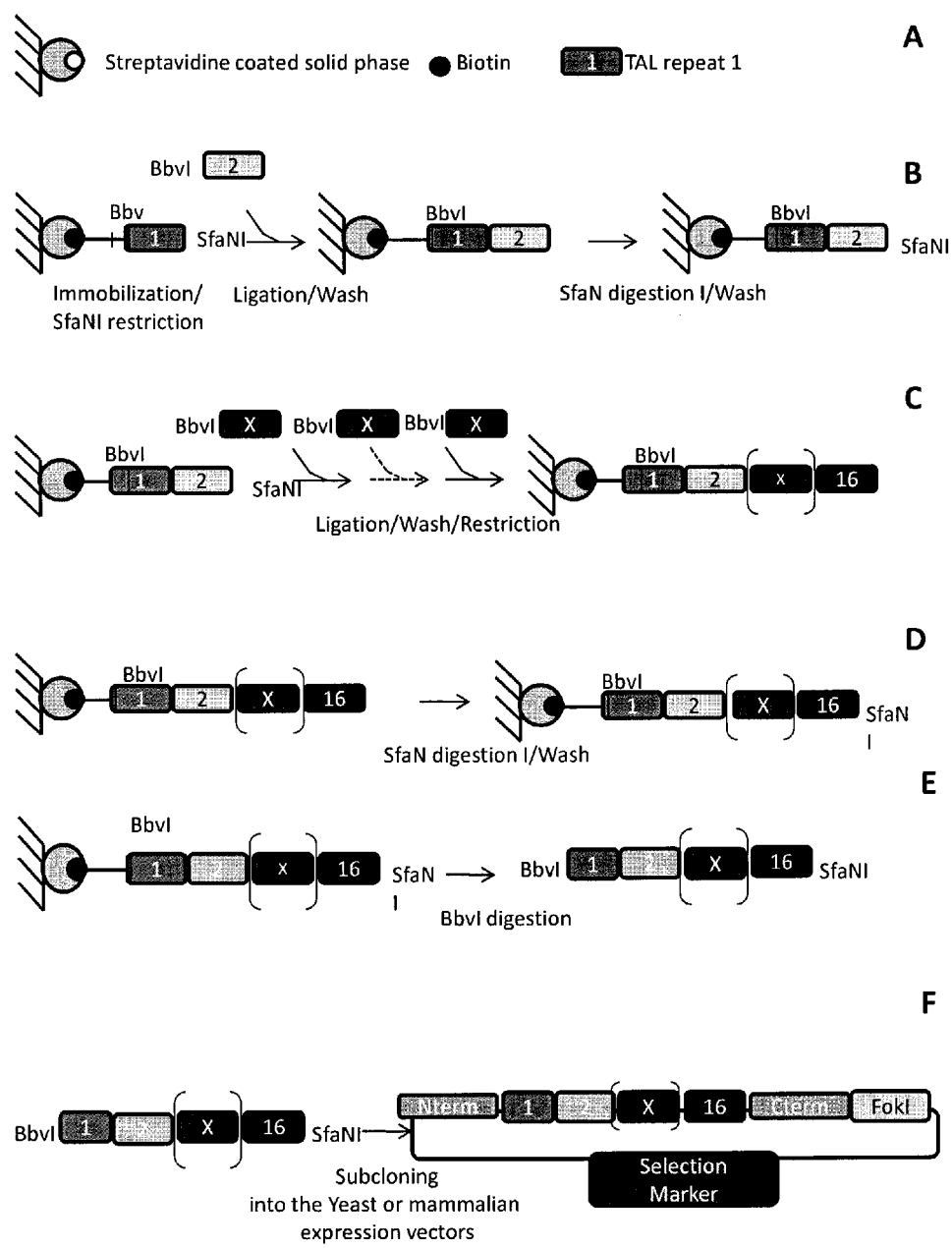

FIG. 4: Tal repeats array_HD or N* assembly and subcloning into yeast and mammalian expression plasmids. A. Legend of materials used for TAL repeat assembly. B. Immobilization of the first biotinylated TAL repeat fragment on a streptavidin coated solid support and ligation to a second TAL repeat harboring SfaNI compatible overhangs (BbvI overhangs displayed in red). C. Consecutive ligation/restriction of TAL repeats to generate the complete XPCT1L TAL repeats array. D. SfaNI digestion of the XPCT1L TAL repeats array. E. BbvI digestion and recovery of the XPCT1L TAL repeats array. Subcloning of XPCT1L TAL repeats array into yeast or mammalian expression plasmids harboring the Nterminal domain of AvrBs3 TAL effector, the eleven first amino acids of its Cterminal domain fused to FokI type IIS restriction endonuclease.

Figure 5:
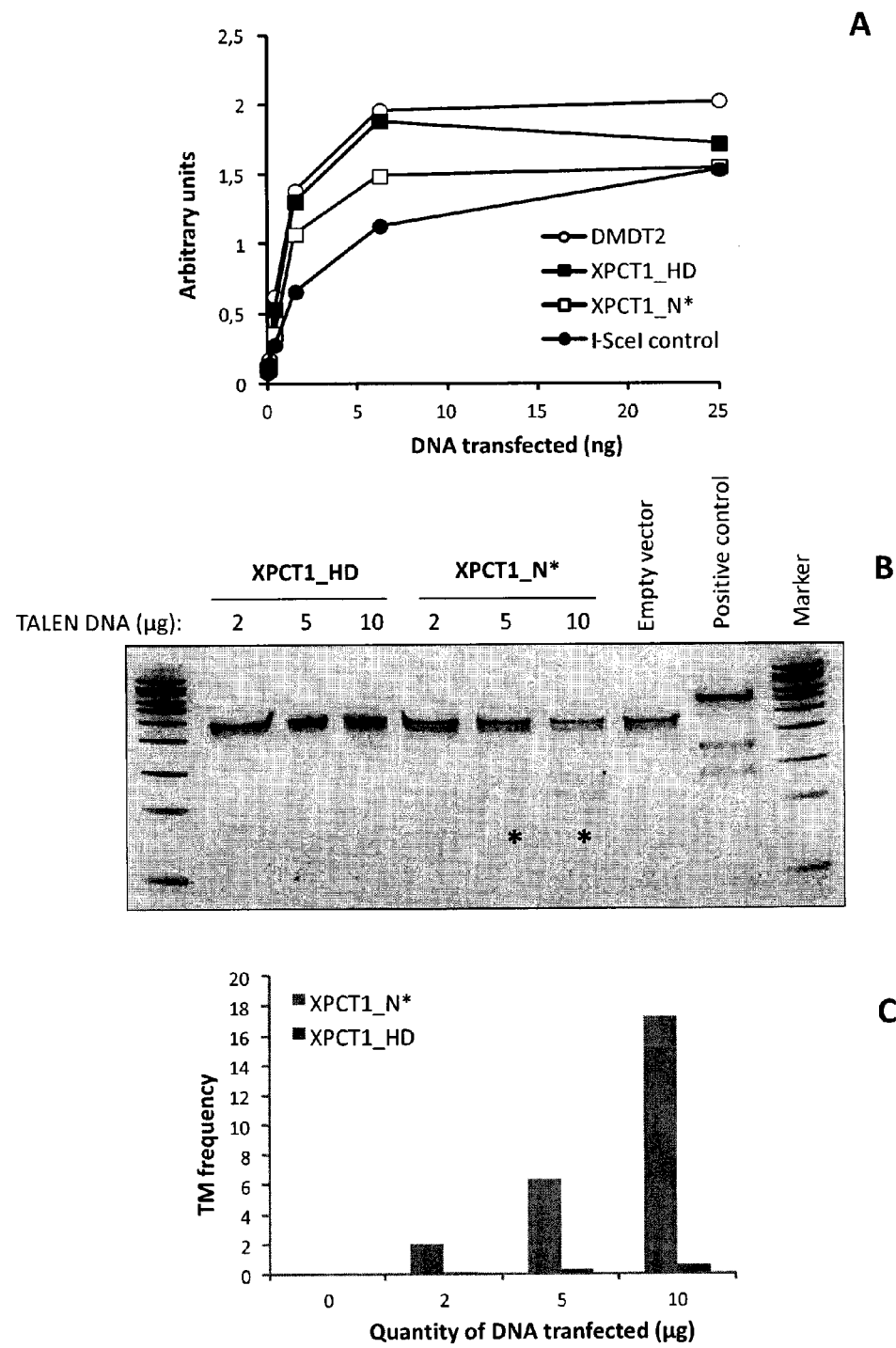

FIG. 5: Nuclease activity of XPCT1_HD or XPCT1_N* TALE-nucleases toward the unmethylated extrachromosomal DNA target and toward the methylated endogenous xpc1 locus. A. Increasing amounts of DNA coding for both TALE-nucleases were transfected in CHO KI and processed according to the protocol described in Material and Methods section. Nuclease activities of XPCT1 TALE-nucleases toward their extrachromosomal unmethylated targets are displayed. B. and C. Increasing amounts of DNA coding for both TALE-nucleases were transfected in 293H cells and three days post transfection, genomic DNA was extracted, xpc1 locus was amplified and amplicons were either analyzed by deep sequencing or used to perform a T7 nuclease assay according to the protocol described by Miller et al (6). B. Results obtained from the T7 nuclease assay. C. Results obtained from deep sequencing analysis.

Figure 6:
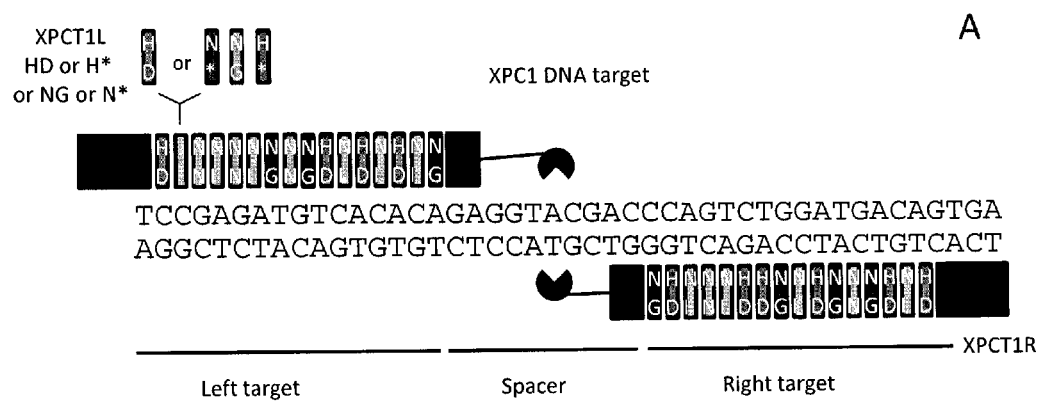
Figure 6:
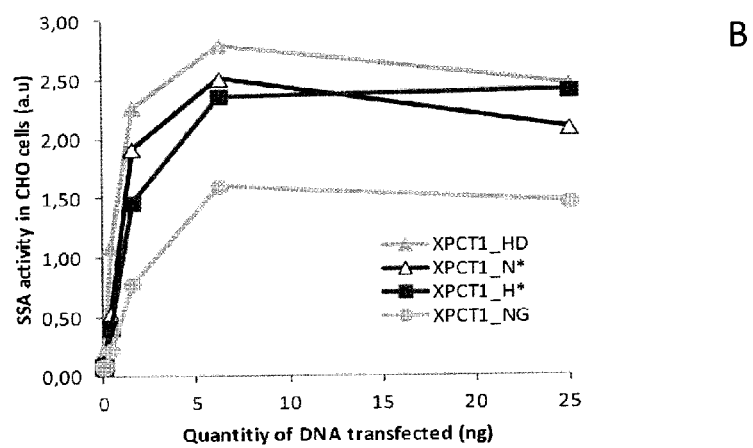
Figure 6:
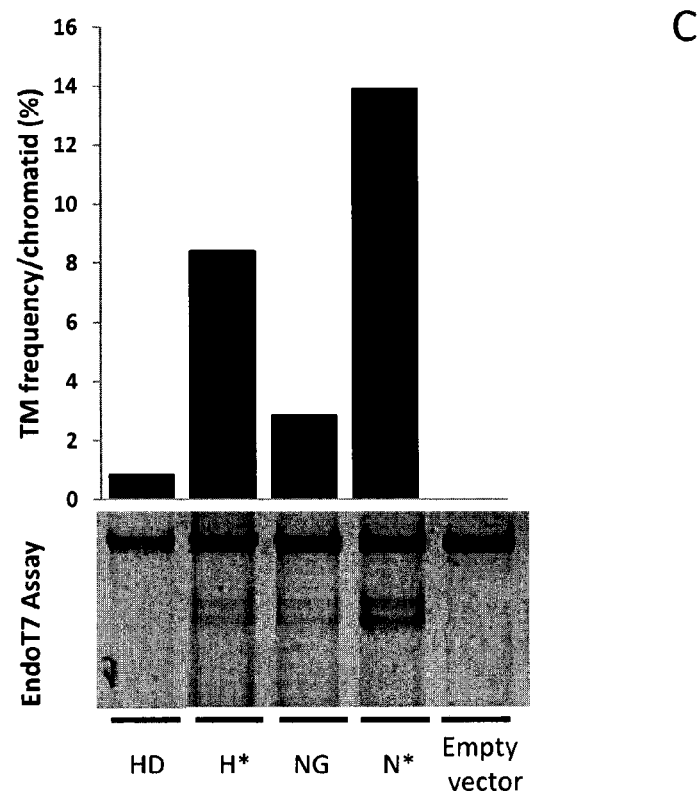
Figure 6:
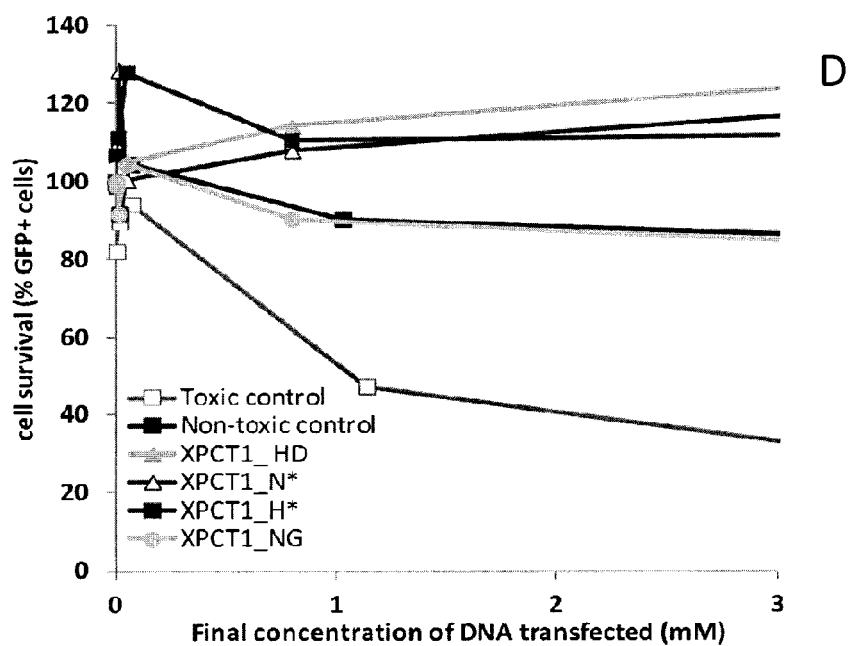

FIG. 6: Ability of naturally occurring TAL repeats H* and NG to overcome XPCT1 TALE-nuclease sensitivity to 5-methyl-cytosine. A. Schematic representation of the XPCT1 TALE-nuclease model used to investigate the influence of TAL repeat H* and NG on TAL DNA binding domain sensitivity to 5-methyl-cytosine. B. Targeted mutagenesis (TM) of endogenous methylated XPC1 target, induced by 5 µg of XPCT1-HD, N*, H* or NG TALE-nucleases encoding plasmids in 293H cells, determined by deep sequencing and C. determined by EndoT7 assay. D. Toxicity assay results obtained with XPCT1 TALE-nucleases bearing either HD, N*, H* or NG at position +2 of its Left TAL DNA binding domain. Increasing amounts of XPCT1 TALE-nucleases were transfected in CHO KI cells with a constant amount of GFP-encoding plasmid. GFP intensity levels were monitored by flow cytometry 1 and 6 days post-transfection. Cell survival was calculated as a ratio (TALE-nuclease-transfected cells expressing GFP at Day 6/control transfected cells expressing GFP at Day 6) (19).

Figure 7:
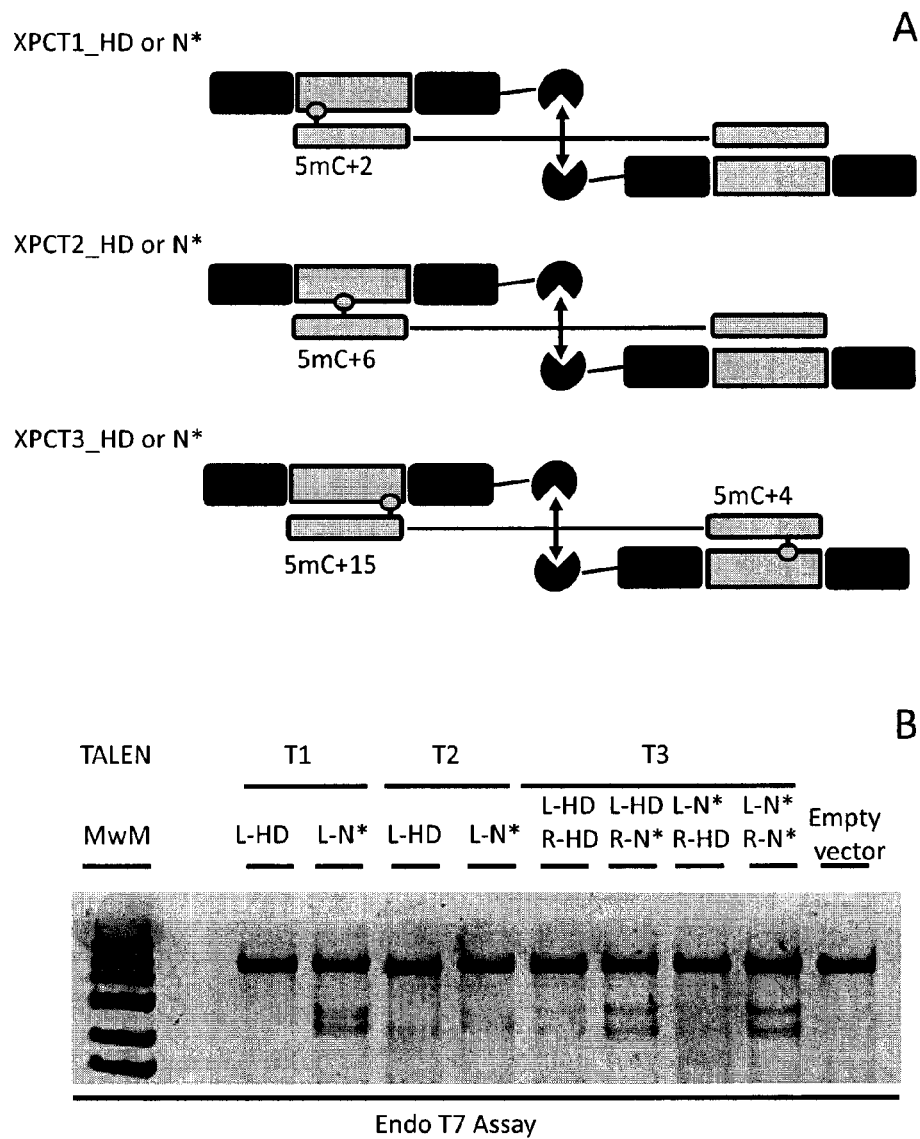
Figure 7:
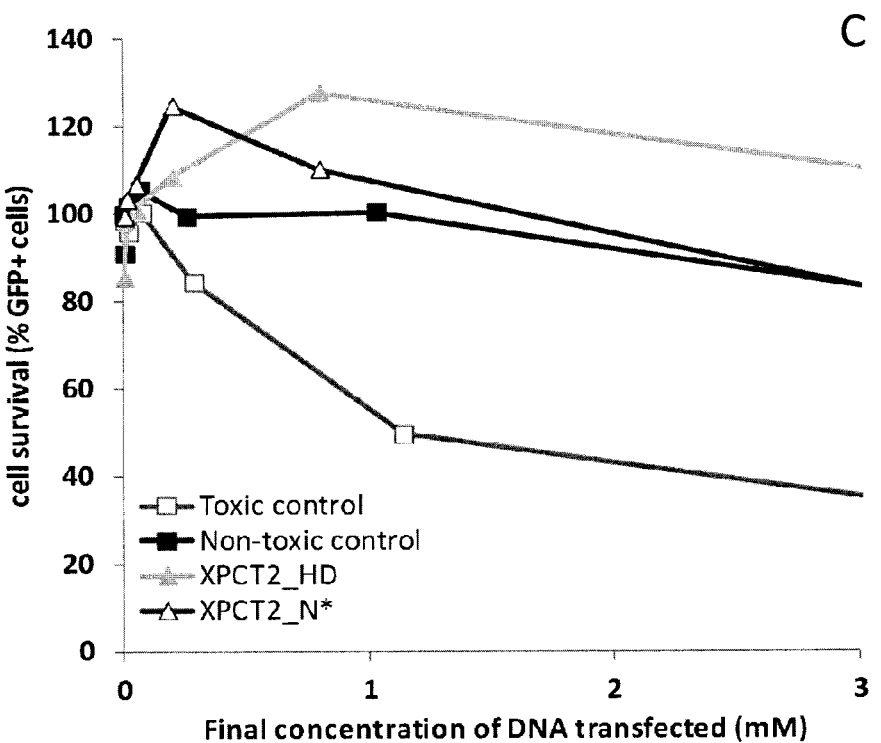
Figure 7:
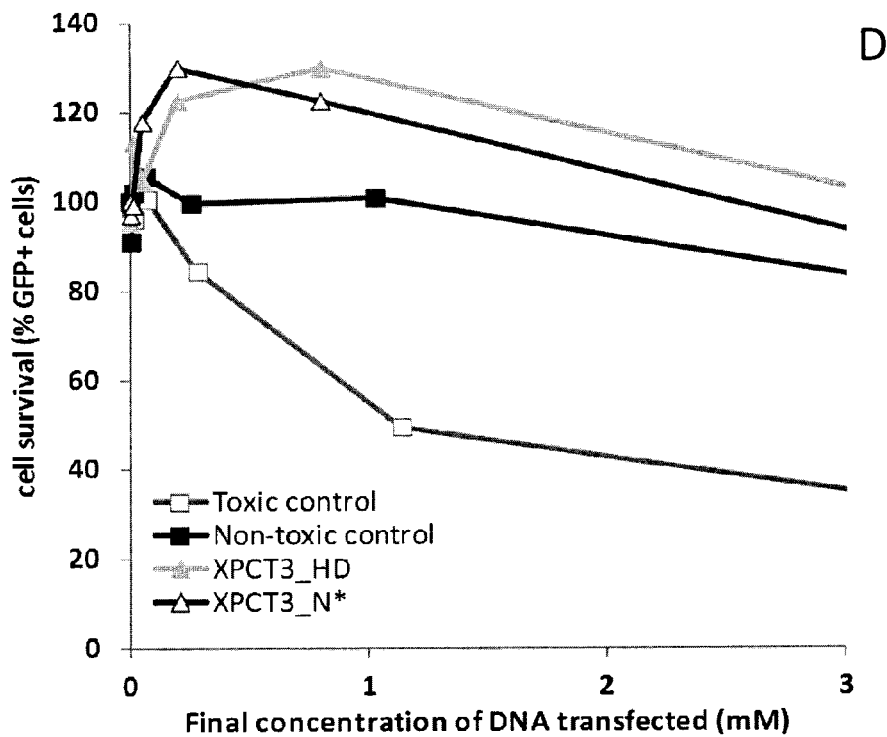

FIG. 7: TAL repeat N*, a universal 5-methyl-cytosine binding module. A. Schematic representation of the XPCT1, T2 and T3 TALE-nucleases used to challenge the ability of TAL repeat N* to overcome TAL DNA binding domain sensitivity to 5-methyl-cytosine. XPC1, XPC2 and XPC3 DNA targets are colored in blue and the position of 5-methyl-cytosines (5mC) are indicated by dots. TAL DNA binding domains are colored in grey and N-term, C-term and FokI domains are colored in black. B. Targeted mutagenesis (TM) of endogenous methylated XPC1, XPC2 and XPC3 targets induced by their respective TALE-nucleases, determined by EndoT7 assay. TALE-nucleases containing different combinations of TAL repeats HD or N* on their right (R) and left (L) DNA binding domains were assayed. As an example for the sake of clarity, XPCT3 bearing TAL repeat HD and N* on its right and left DNA binding domains respectively, is indicated as XPCT3 R-HD, L-N*. C. Toxicity assay results obtained with XPCT2 and XPCT3 TALE-nucleases bearing either HD or N* at different positions of their left and right TAL DNA binding domains (XPCT3-HD stands for XPCT3 bearing TAL repeats HD on its left and right DNA binding domains and XPCT3-N* stands for XPCT3 bearing TAL repeats N* on its left and right DNA binding domains).

Figure 8:
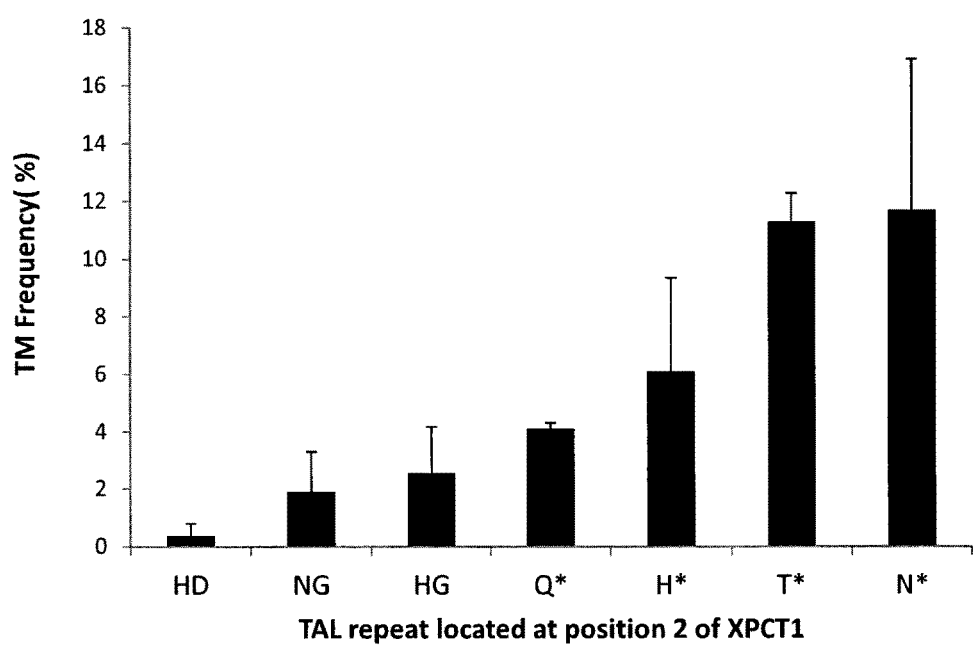

FIG. 8: Ability engineered TAL repeats T* and Q* to overcome TAL DNA binding domain sensitivity to 5-methylated Cytosine. Frequency of Targeted mutagenesis (TM) of endogenous methylated XPC1 target, induced by 10 µg of XPCT1-HD, NG, HG, N*, H*, Q* and T* TALE-nuclease encoding plasmids in 293H cells, determined by deep sequencing. The results shown in this figure were obtained from a number of experiments ≥2.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Transcription activator like effector derived protein has recently emerged as a new tool for genome engineering. However, relevant chemical modification in the genome such as DNA methylation as non limiting example interferes with TALE gene targeting. In the present study, the inventors showed that RVD "stars" are capable of targeting chemically modified nucleic acid base.

In a general aspect, the present invention relates to Transcription Activator-Like Effector derived proteins that allow to efficiently target and/or process chemically modified nucleic acids. More particularly the present invention relates to repeat modules or sequences comprising Repeat Variable-Diresidue (RVD) that allow to efficiently detect, target and/or process nucleic acids with chemical modifications such as alkylation as a non-limiting example. The present invention reports the characterization of TALE derived protein sensitivity to chemical nucleic acid base modifications such as cytosine methylation and presents an efficient method to overcome such sensitivity. This method relies on the utilization of RVDs X* or ** as an entity capable of efficient binding of chemically modified base, wherein X represents one amino acid residue selected from the group of A, G, V, L, I, M, S, T, C, P, D, E, F, Y, W, Q, N, H, R and K and * represents a gap in one position of the RVD.

Recently, applicant has discovered a new class of modular base per base nucleic acid binding domains (MBBBD) in the genome of an endosymbiont species *Burkholderia rhizoxinica* displaying some similarities with TALEs from *Xanthomonas*. These new modular proteins and their use for targeting nucleic acid sequences into a genome are the subject-matter of an application filed on Jul. 6, 2012 under U.S. 61/668,721 and U.S. 61/675,160. Although the modules from such proteins are very different and share less than 50% homology with TALE repeats, while displaying much more inter-variability, their specificity with respect to nucleic acid bases is apparently similarly driven by amino acids in $12^{th}$ and $13^{th}$ positions (RVD-like). Position $13^{th}$ in MBBBDs could determine the specificity of the nucleic acid base by itself. However, it has been observed in these modules that position $13^{th}$ can be absent and thus be "star" as in the present invention. Given this fact, it is considered the teaching of the present invention is applicable to such new MBBBD domains, as well as other proteins bearing RVD-like structures. The present invention thus extends to the introduction of "*" in RVD-like structures in order to target methylated nucleic acid sequences without being limited to the RVDs found in *Xanthomonas* TALEs.

I. TALE-Derived Protein Capable of Binding Chemically Modified Base.

The present invention relates to a Repeat Variable Diresidue (RVD) X* or **, preferably N*, Q*, T* or H* that is capable of efficient binding chemically modified base, wherein X represents one amino acid residue selected from the group of A, G, V, L, I, M, S, T, C, P, D, E, F, Y, W, Q, N, H, R and K and * represents a gap in one position of the RVD.

Repeat Variable Diresidue (RVD) is included in one repeat module or sequence responsible for the binding of a nucleic acid base in a nucleic acid target sequence at the level of variable amino acids located at positions 12 and 13 (i.e. Repeat Variable Di residues, RVD).

In the present invention, said RVD region responsible for the binding of a nucleic acid base comprises any known amino acid residues in positions 12 and 13. In a preferred embodiment, RVDs comprise one amino acid residue from the group consisting of A, G, V, L, I, M, S, T, C, P, D, E, F, Y, W, Q, N, H, R and K in position 12 according to amino acid one-letter code. In another preferred embodiment, RVDs comprise one amino acid residue from the group consisting of A, G, V, L, I, M, S, T, C, P, D, E, F, Y, W, Q, N, H, R and K in position 13 according to amino acid one-letter code. In another embodiment, RVDs comprise a combination of amino acid residues A, G, V, L, I, M, S, T, C, P, D, E, F, Y, W, Q, N, H, R and K according to amino acid one-letter code in positions 12 and 13 for recognizing one nucleic acid base in nucleic acid target sequence. In a preferred embodiment, RVDs responsible for the binding of a modified nucleic acid base comprise a gap in position 12 and/or 13, more particularly RVDs are X* or **, preferably N*, Q*, T* or H* and are capable of efficient binding of chemically modified base, wherein X represents one amino acid residue selected from the group of A, G, V, L, I, M, S, T, C, P, D, E, F, Y, W, Q, N, H, R and K and * represents a gap in one position of the RVD.

Said RVD of the present invention is capable of binding a modified nucleotide comprises a base different from the classical purine and pyrimidine bases, i.e. respectively Adenine, Guanine and Cytosine, Uracil and Thymine. In another aspect, said chemically modified nucleic acid base recognized by the RVD of the present invention is a nucleotide comprising one or several additional chemical groups such as alkyl or hydroxyl as non-limiting example. Said additional group may be a methyl group which refers to the transfer of one carbon group on a nucleotide. Alkylation refers to the transfer of a long chain carbon group. In another embodiment, said chemically modified nucleotide comprises a 5-methyl cytosine base. In another embodiment, said modified nucleic acid base comprises a base selected from the group consisting of 5-hydroxymethylcytosine, 5-formylcytosine and 5-carboxylcytosine. In another embodiment, said RVD of the present invention is capable of binding DNA sequences comprising molecular lesions such as a non-limiting example pyrimidine dimers formed from cytosine or thymine bases via photochemical reactions.

The present invention also relates to a repeat sequence or repeat module of a Transcription Activator-Like Effector (TALE) comprising a RVD responsible for the binding of a modified nucleic acid base in a nucleic acid target sequence. In addition to the different aspects listed above for variable residues in positions 12 and 13, said repeat sequence named TALE like repeat sequence of the invention can comprise one or several additional mutations in one or several of the 30 to 42 amino acids constituting said RVD, more preferably 33 to 35 amino acids, again more preferably 33 or 34 amino acids. By mutations are encompassed substitutions toward any natural amino acids from the group consisting of A, G, V, L, I, M, S, T, C, P, D, E, F, Y, W, Q, N, H, R and K according to amino acid one-letter code, but also insertions and deletions of one or several amino acid residues.

In other words, the scope of the present invention encompasses one repeat module or sequence responsible for the binding of a modified nucleic acid base in a nucleic acid target sequence at the level of variable amino acids located at positions 12 and 13 (i.e. Repeat Variable Di residues, RVD). In particular, the repeat sequence or module of a TALE comprises a RVD selected from the group consisting of X* and **, preferably N*, Q*, T* or H* for binding chemical modified base nucleic acid wherein X represents one amino acid residue selected from the group of A, G, V, L, I, M, S, T, C, P, D, E, F, Y, W, Q, N, H, R and K and * represents a gap in one position of the RVD.

The present invention also relates to a TALE binding domain specific for a nucleic acid target sequence comprising a plurality of TALE repeat sequences comprising each one a Repeat Variable Diresidue region (RVD) which is responsible for the binding of one specific nucleic acid base in said nucleic acid target sequence and wherein said TALE DNA binding domain comprises one or more RVD selected from the group consisting of X* and **, preferably N*, Q*, T* or H* for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD. In a preferred embodiment, said repeat domain comprises between 8 and 30 repeat sequences derived from a TALE, more preferably between 8 and 20, again more preferably 5, 6, 7, 8, 9, 10, 11, 12, 13, 14, 15, 16, 17, 18, 19, 20 repeat sequences.

II. TALE Chimeric Protein Capable of Processing Chemically Modified Base

The present invention also relates to a chimeric protein derived from a TALE corresponding to a fusion between a TALE DNA binding domain as mentioned above and an additional protein domain to process the DNA within or adjacent to the specific nucleic acid target sequence. In other words, said polypeptide of the present invention is a chimeric protein derived from a TALE comprising:

(a) A TALE DNA binding domain specific for a nucleic acid target sequence comprising a plurality of TALE repeat sequences containing each one a Repeat Variable Diresidue region (RVD) which is responsible for the binding of one specific nucleic acid base in said nucleic acid target sequence wherein said TALE DNA binding domain comprises one or more RVD selected from the group consisting of X* and **, preferably N*, Q*, T* or H* for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD, (b) An additional protein domain to process the DNA within or adjacent to the specific nucleic acid target sequence In particular embodiment, said chimeric protein according to the present invention can comprise at least one peptidic linker to fuse said TALE DNA binding domain and said additional protein domain processing the DNA. In a preferred embodiment, said peptidic linker is flexible. In another preferred embodiment, said peptidic linker is structured.

In a particular embodiment, the additional protein domain of the chimeric protein may be a transcription activator or repressor (i.e. a transcription regulator), or a protein that interacts with or modifies other proteins implicated in DNA processing. Non-limiting examples of DNA processing activities of said chimeric protein of the present invention include, for example, creating or modifying epigenetic regulatory elements, making site-specific insertions, deletions, or repairs in DNA, controlling gene expression, and modifying chromatin structure.

The additional protein domain fused to the TALE DNA binding domain may have a catalytical activity selected from the group consisting of nuclease activity, polymerase activity, kinase activity, phosphatase activity, methylase activity, topoisomerase activity, integrase activity, transposase activity, ligase activity, helicase activity, recombinase activity. In a preferred embodiment, said protein domain is an endonuclease; in another preferred embodiment, said protein domain is an exonuclease.

When comprising an endonuclease, said chimeric protein of the present invention derived from a TALE is a TALE-nuclease; in other words, in the scope of the present invention is a TALE-nuclease comprising:

(a) A Transcription Activator-Like Effector (TALE) DNA binding domain specific for a nucleic acid target sequence comprising a plurality of TALE repeat sequences containing each one a Repeat Variable Diresidue region (RVD) which is responsible for the binding of one specific nucleic acid base pair in said nucleic acid target sequence and wherein said TALE DNA binding domain comprises one or more RVD selected from the group consisting of X* and **, preferably N*, Q*, T* or H* for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD;

(b) An endonuclease domain to process the DNA within or adjacent to the specific nucleic acid target sequence.

Depending on the endonuclease domain that constitutes said TALE nuclease, cleavage in the nucleic acid target sequence corresponds to either a double-stranded break or a single-stranded break.

As non limiting example, said endonuclease can be a type IIS FokI endonuclease domain or functional variant thereof which functions independently of the DNA binding domain and induces nucleic acid double-stranded cleavage as a dimer (Li, Wu et al. 1992; Kim, Cha et al. 1996). Amino acid sequence of FokI variants can be prepared by mutations in the DNA, which encodes the catalytic domain. Such variants include, for example, deletions from, or insertions or substitutions of, residues within the amino acid sequence. Any combination of deletion, insertion, and substitution may also be made to arrive at the final construct, provided that the final construct possesses the desired activity. Said nuclease domain of FokI variant according to the present invention comprises a fragment of a protein sequence having at least 80%, more preferably 90%, again more preferably 95% amino acid sequence identity with the protein sequence of FokI. In particular embodiment, a first and a second chimeric proteins can function respectively as monomer to act together as a dimer to process the nucleic acid within or adjacent to a specific nucleic acid target. As a non-limiting example, the two monomers can recognize different adjacent nucleic acid target sequences and the two protein domains constituting each chimeric protein derived from a TALE, function as subdomains that need to interact in order to process the nucleic acid within or adjacent to said specific nucleic acid target sequence.

In another particular embodiment, said chimeric protein is a monomeric TALE-nuclease that does not require dimerization for specific recognition and cleavage. As non limiting example, such monomeric TALE-nuclease comprises a TALE DNA binding domain fused to the catalytic domain of I-TevI or a variant thereof.

In a preferred embodiment, said TALE-nuclease according to the present invention can comprise at least one peptidic linker to fuse said TALE DNA binding domain and said endonuclease domain. In a preferred embodiment, said peptidic linker is flexible or structured.

In a more specific embodiment, the invention relates to a TALE-nuclease comprising amino acid sequence selected from the group consisting of SEQ ID NO: 38 to SEQ ID NO: 49

In a more preferred embodiment, the DNA binding domain of the TALE-nuclease according to the present invention comprises one or more Repeat Variable Diresidue region (RVD) which is responsible for the binding of one chemically modified nucleic acid base in a nucleic acid target sequence. RVDs of said TALE-nuclease can take one or several of the different aspects statements previously listed for RVDs and repeat sequences of a TALE.

It is understood that RVDs, DNA binding domains, TALE-nucleases, chimeric protein according to the present invention can also comprise single or plural additional amino acid substitutions or amino acid insertion or amino acid deletion introduced by mutagenesis process well known in the art. Is also encompassed in the scope of the present invention variants, functional mutants and derivatives from RVDs, DNA binding domains, TALE-nucleases, chimeric protein and polypeptides according to the present invention. Are also encompassed in the scope of the present invention RVDs, DNA binding domains, TALE-nucleases, chimeric proteins and polypeptides which present a sequence with high percentage of identity or high percentage of homology with sequences of RVDs, DNA binding domains, TALE-nucleases, chimeric proteins and polypeptides according to the present invention, at nucleotidic or polypeptidic levels. By high percentage of identity or high percentage of homology it is intended 70%, more preferably 75%, more preferably 80%, more preferably 85%, more preferably 90%, more preferably 95, more preferably 97%, more preferably 99% or any integer comprised between 70% and 99%.

In another aspect of the present invention are polynucleotides encoding for or comprising a coding sequence for the polypeptides, TALE DNA binding domain, chimeric protein derived from a TALE and TALE-nuclease according to the present invention. Are also encompassed vectors comprising such polynucleotides.

Is also encompassed in the scope of the present invention a host cell which comprises a vector and/or a recombinant polynucleotide encoding for or comprising a coding sequence for the polypeptides, TALE DNA binding domain, chimeric protein derived from a TALE and TALE-nuclease according to the present invention.

Is also encompassed in the scope of the present invention a non-human transgenic animal comprising a vector and/or a recombinant polynucleotide encoding for or comprising a coding sequence for the polypeptides, TALE DNA binding domain, chimeric protein derived from a TALE and TALE-nuclease according to the present invention. Is also encompassed in the scope of the present invention a transgenic plant comprising a vector and/or a recombinant polynucleotide encoding for or comprising a coding sequence for the polypeptides, TALE DNA binding domain, chimeric protein derived from a TALE and TALE-nuclease according to the present invention.

The present invention also relates to a kit comprising at least a polypeptide or a TALE DNA binding domain or a chimeric protein derived from a TALE or a TALE-nuclease according to the present invention or a vector and/or a recombinant polynucleotide encoding for or comprising a coding sequence for such recombinant molecules and instructions for use said kit.

The present invention also relates to a composition comprising at least a polypeptide or a TALE DNA binding domain or a chimeric protein derived from a TALE or a TALE-nuclease according to the present invention or a vector and/or a recombinant polynucleotide encoding for or comprising a coding sequence for such recombinant molecules and a carrier. More preferably, is a pharmaceutical composition comprising such recombinant molecules and a pharmaceutically active carrier. For purposes of therapy, the chimeric protein according to the present invention and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of the targeted disease and in a genome correction of the lesion or abnormality.

III. Methods

1. Method for Synthesizing a TALE Derived Protein Capable of Binding Chemically Modified Nucleic Acid Base In another aspect, the present invention also relates to methods for synthesizing polynucleotides encoding TALE DNA binding domains (also named TALE arrays), TALE derived protein, TALE-nucleases and chimeric proteins according to the present invention for various applications ranging from targeted DNA cleavage to targeted gene regulation.

One aspect of the invention is a method for synthesizing a transcription activator-like effector (TALE) protein to nucleic acid target sequence comprising a chemically modified nucleic acid base. Said method comprises assembling a plurality of TALE-like repeat sequences, each of said sequences comprising a repeat variable-diresidue (RVD) specific to each nucleic acid base of said sequence. RVD(s) that specifically targets the chemically modified nucleic acid base included in the nucleic acid target sequence are selected from X* or **, wherein X represents one amino acid residue selected from the group of A, G, V, L, I, M, S, T, C, P, D, E, F, Y, W, Q, N, H, R and K and * represents a gap in one position of the RVD, in order to accommodate said chemically modified nucleic acid base.

In a preferred embodiment, said method comprises at least one of the following steps:

(a) determining a nucleic acid target sequence comprising chemically modified nucleic acid base in the genome of a cell;

(b) assembling TALE-like repeat polynucleotide sequences, each repeat being specific to each nucleic acid base of said nucleic acid target sequence by encoding a repeat variable-diresidue (RVD) comprising at least one RVD selected from the group consisting of:
HD for recognizing C;
NG for recognizing T;
NI for recognizing A;
NN for recognizing G or A;
NS for recognizing A or C or G or T;
HG for recognizing T;
IG for recognizing T;
NK for recognizing G;
HA for recognizing C;
ND for recognizing C;
HI for recognizing C;
HN for recognizing G;
NA for recognizing G;
SN for recognizing G or A; and
YG for recognizing T;
wherein the RVD(s) specifically targeting the chemically modified nucleic acid base(s) in the nucleic target sequence are selected from the RVDs X* and **, where
X represents one amino acid residue selected from the group of A, G, V, L, I, M, S, T, C, P, D, E, F, Y, W, Q, N, H, R and K, and * represents a gap in one position of the RVD, (c) expressing said polynucleotide sequence assembled in step (b) in said cell.

In a more preferred embodiment, said chemically modified base corresponds to modified nucleic acid base as described above and preferably is a methylated base, in particular a 5-methyl cytosine.

The present invention also relates to a method to synthesize a chimeric protein as described above to process nucleic acid at a locus defined by a nucleic acid target sequence that comprises a chemically modified base, said method comprising:

(a) synthesizing a polynucleotide sequence comprising a fusion of:
(i) a first polynucleotide encoding a transcription activator-like effector (TALE) protein comprising a plurality of TALE-like repeat sequences, each repeat comprising a repeat variable-diresidue (RVD) specific to each nucleic acid base of said nucleic acid target sequence, wherein the RVD(s) that specifically targets the chemically modified nucleic acid base within said nucleic acid target sequence are selected from X* or **, wherein X represents one amino acid residue selected from the group of A, G, V, L, I, M, S, T, C, P, D, E, F, Y, W, Q, N, H, R and K and * represents a gap in one position of the RVD;
(ii) a second polynucleotide encoding an additional protein domain to process nucleic acid within or adjacent to said nucleic acid target sequence that comprises a chemically modified base;
(b) expressing said polynucleotide sequence of step a) into a host cell.

In another preferred embodiment, said RVD specifically targeting the chemically modified base(s) are preferentially selected from RVD N*, T*, Q* and H*. In another particular embodiment, said RVD specifically targeting the chemically modified base(s) are preferentially selected from RVD NG and HG.

In a preferred embodiment, said additional protein domain has a catalytical activity selected from the group consisting of nuclease activity, polymerase activity, kinase activity, phosphatase activity, methylase activity, topoisomerase activity, integrase activity, transposase activity, ligase activity, helicase activity, recombinase activity. In another preferred embodiment, the protein domain of the chimeric protein can be a transcription activator that can potentially allows site specific activation of methylated promoters responsible for gene silencing. In a more preferred embodiment, said additional protein domain is an endonuclease and thus the chimeric protein is a TALE-nuclease.

As non limiting example, each TALE-like repeat can be assembled together using a solid support method composed of consecutive restriction, ligation, washing step as shown in FIG. 4 then can be further in a vector. Other methods such as Golden Gate cloning methods and variants or FLASH assembly method may be used as non limiting example (5, 21, 23, 24).

As used herein, the term "expressed" refers to generation of a polynucleotide (transcript) or a polypeptide product. The methods of the invention involve introducing polynucleotide into a cell. The TALE derived protein or chimeric protein may be synthesized in situ in the cell as a result of the introduction of polynucleotide encoding polypeptide into the cell. Alternatively, the TALE derived protein or chimeric protein could be produced outside the cell and then introduced thereto. Methods for introducing a polynucleotide construct into bacteria, plants, fungi and animals are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposomes and the like. For example, transient transformation methods include for example microinjection, electroporation or particle bombardment. Said polynucleotides may be included in vectors, more particularly plasmids or virus, in view of being expressed in prokaryotic or eukaryotic cells. Alternatively, polynucleotide transcript may be introduced into the cell.

More particularly, the present invention relates to a method to generate a nucleic acid encoding a TALE DNA binding domain insensitive to cytosine methylation comprising the steps of:
(a) determining a DNA target sequence in the genome of a cell,
(b) synthesizing a nucleic acid encoding a TALE DNA binding domain specific for said DNA target sequence comprising a plurality of TALE repeat sequences containing each one a Repeat Variable Diresidue region (RVD) which is responsible for the binding of one specific nucleotide in said DNA target sequence wherein said TALE DNA binding domain comprises one or more RVD selected from the group consisting of X* and ** for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD;
(c) introducing said nucleic acid into said cell,
thereby obtaining a nucleic acid encoding a TALE DNA binding domain which binds said DNA target sequence independently of its cytosine methylation status when expressed in appropriate conditions.

In a particular embodiment, said TALE DNA binding domain which binds the DNA target sequence promotes transcription activation around said DNA target sequence independently of chemically modification, when expressed in appropriate conditions.

In another embodiment, the present invention relates to a method to generate a nucleic acid encoding a TALE-nuclease insensitive to cytosine methylation comprising the steps of:
(a) determining a DNA target sequence in the genome of a cell,
(b) synthesizing a nucleic acid encoding (i) a TALE DNA binding domain specific for said DNA target sequence comprising a plurality of TALE repeat sequences containing each one a Repeat Variable Diresidue region (RVD) which is responsible for the binding of one specific nucleotide in said DNA target sequence wherein said TALE DNA binding domain comprises one or more RVD selected from the group consisting of X* and ** for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD,
(ii) an endonuclease domain to process the DNA within or adjacent to the specific DNA target sequence,
(c) introducing said nucleic acid into said cell,
thereby obtaining a nucleic acid encoding a TALE-nuclease wherein said TALE-nuclease process the DNA within or adjacent to the specific DNA target sequence independently of its cytosine methylation status, when expressed in appropriate conditions.

In a preferred embodiment, said TALE-nuclease according to the present invention can comprise at least one peptide linker to fuse said TALE DNA binding domain and said endonuclease domain. In a preferred embodiment, said peptidic linker is flexible. In another preferred embodiment, said peptidic linker is structured.

More particularly, the present invention encompasses a chimeric protein obtainable by a method comprising at least the steps of:
(a) Determining a DNA target sequence of interest;
(b) Synthesizing a repeat sequence domain specific for said DNA target sequence comprising a plurality of TALE repeat sequences containing each one a Repeat Variable Diresidue region (RVD) which is responsible for the binding of one specific nucleotide pair in said DNA target sequence and wherein said TALE DNA binding domain comprises one or more RVD selected from the group consisting of X* and ** for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD;
(c) Providing a protein domain to process the DNA within or adjacent to the specific DNA target sequence;
(d) Optionally designing a peptidic linker to link polypeptides obtained in b) and c);
(e) Assembling said chimeric protein;
(f) Testing the activity of said chimeric protein.

In a further embodiment, synthesis step b) can be done using a solid support method composed of consecutive restriction/ligation/washing steps as shown in FIG. 4 and examples section; step c) can be done by cloning said protein domain of interest into a plasmidic vector; in the case where said chimeric protein according to the invention is a TALE-nuclease, as non-limiting example, said protein domain can be cloned together in a same vector with chosen peptidic linker and eventual additional N and C terminal backbones for a RVD. Assembling step e) can be done by cloning repeat sequence domain of step b) in the vector resulting from step e). Testing step f) can be done, in the case where said chimeric protein is a TALE-nuclease as a non-limiting example, in yeast by using a yeast target reporter plasmid containing the DNA target sequence as previously described (International PCT Applications WO 2004/067736 and in [Epinat, Arnould et al. 2003 (13); Chames, Epinat et al. 2005 (17); Arnould, Chames et al. 2006 (14); Smith, Grizot et al. 2006 (18)]. The activity of said TALE-nuclease can be tested at 30° C. and 37° C. in a yeast SSA assay previously described (International PCT Applications WO 2004/067736 and in [Epinat, Arnould et al. 2003 (13); Chames, Epinat et al. 2005 (17); Arnould, Chames et al. 2006 (14); Smith, Grizot et al. 2006 (18)].

2. Method for Processing Target Nucleic Acid Sequence Comprising Chemically Modified Nucleic Acid Base In another aspect, the present invention also relates to methods for use of protein comprising TALE domain according to the present invention for various applications ranging from targeted nucleic acid cleavage to targeted gene regulation.

In a particular embodiment, the present invention relates to a method for binding a nucleic acid target sequence comprising at least one chemically modified nucleic acid base, said method comprising contacting: (i) a nucleic acid target sequence comprising chemically modified nucleic acid base and (ii) a TALE protein comprising a repeat variable-diresidue (RVD) specific to each nucleotide base of said nucleic acid target sequence, wherein the RVD(s) that specifically targets the chemically modified nucleic acid base within said nucleic acid target sequence are selected from X* or **, preferably N*, Q*, T* or H*, wherein X represents one amino acid residue selected from the group of A, G, V, L, I, M, S, T, C, P, D, E, F, Y, W, Q, N, H, R and K and * represents a gap in one position of the RVD.

More particularly, the present invention relates to a method to bind a nucleic acid target sequence comprising at least one chemically modified nucleic acid base, said method comprising:
(a) providing a cell containing a nucleic acid target sequence that comprises a chemically modified base,
(b) synthesizing within said cell a TALE protein directed to said nucleic acid target sequence as described above and,
(c) testing the binding affinity of said TALE protein with said nucleic acid target sequence that comprises said chemically modified base.

In a preferred embodiment, said specific DNA sequence comprising at least one chemically modified dinucleotide selected from the group consisting of CpG, CpA, CpT, CpC.

In another aspect, the present invention relates to a method to process a nucleic acid target sequence comprising at least one chemically modified nucleic acid base by using a chimeric protein as previously defined. Said method preferably comprises the following steps of:
(a) providing a cell containing a nucleic acid target sequence that comprises a chemically modified nucleic acid base;
(b) synthesizing within said cell a chimeric protein directed to said nucleic acid target sequence, so that said chimeric protein process the nucleic acid within or adjacent to said nucleic acid target sequence independently of chemical modification and,
(c) testing the nucleic acid processing at the locus of said nucleic acid target sequence.

In general, the chimeric protein of the present invention can have a catalytical activity selected from the group consisting of nuclease activity, polymerase activity, kinase activity, phosphatase activity, methylase activity, topoisomerase activity, integrase activity, transposase activity, ligase activity, helicase activity, recombinase activity. In another preferred embodiment, the protein domain of the chimeric protein can be a transcription activator that can potentially allows site specific activation of methylated promoters responsible for gene silencing. In another preferred embodiment, the protein domain can also be a transcription repressor.

Any nucleic acid target sequence can be processed by the present methods. For example, the nucleic acid target sequence can be chromosomal, organelle sequences such as mitochondrial or choloroplast sequences, or the nucleic acid target sequence can be a plasmid or viral sequence. The term "processing" as used herein means that the sequence is considered modified simply by the binding of the polypeptide. The term "processing" as used herein means for example promoting transcription activation around said nucleic acid target sequence. For example, said chimeric protein can comprise a TALE domain according to the present invention fused to a transcription activator such as VP16. Said method is particularly well-suited to reactivate genes in cells wherein their promoters have been silenced by methylation. In other words, the present invention relates to a method to activate transcription of genes in cells where their transcription is normally silenced by methylation. In a preferred embodiment, said cells are eukaryotic cells or primary cells, stem cells, induced Pluripotent Stem (iPS) cells or cells lines derived from any previous types of cells.

As non limiting example, the binding affinity can be tested by detecting signal of reporter proteins such as fluorescent proteins fused to said TALE proteins, or by detecting the presence of the TALE protein with for example antibodies. In a preferred embodiment, the binding affinity, particularly the nucleic acid processing may be tested by a nuclease activity or transcriptional activity. For example, in the case where said chimeric protein is a TALE-nuclease, nucleic acid processing can be tested in yeast by using a yeast target reporter plasmid containing the nucleic acid target sequence as previously described (International PCT Applications WO 2004/067736 and in [Epinat, Arnould et al. 2003 (13); Chames, Epinat et al. 2005 (17); Arnould, Chames et al. 2006 (14); Smith, Grizot et al. 2006 (18)]. The activity of said TALE-nuclease can be tested at 30° C. and 37° C. in a yeast SSA assay previously described (International PCT Applications WO 2004/067736 and in [Epinat, Arnould et al. 2003 (13); Chames, Epinat et al. 2005 (17); Arnould, Chames et al. 2006 (14); Smith, Grizot et al. 2006 (18)

In a particular embodiment, said additional protein domain is a catalytic domain which has nuclease activity, more preferably, endonuclease activity and the present invention more particularly relates to a method for modifying the genetic material of a cell within or adjacent to a nucleic acid target sequence.

The double strand breaks caused by endonucleases are commonly repaired through non-homologous end joining (NHEJ). NHEJ comprises at least two different processes. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. The present invention relates to a method for processing the genetic material in a cell within or adjacent to a nucleic acid target sequence by using chimeric protein, preferably A TALE-nuclease according to the present invention that allows nucleic acid cleavage that will lead to the loss of genetic information and any NHEJ pathway will produce targeted mutagenesis. In a preferred embodiment, the present invention related to a method for modifying the genetic material of a cell within or adjacent to a nucleic acid target sequence by generating at least one nucleic acid cleavage and a loss of genetic information around said nucleic acid target sequence thus preventing any scarless re-ligation by NHEJ. Said modification may be a deletion of the genetic material, insertion of nucleotides in the genetic material or a combination of both deletion and insertion of nucleotides.

The present invention also relates to a method for modifying nucleic acid target sequence further comprising the step of expressing an additional catalytic domain into a host cell. In a more preferred embodiment, the present invention relates to a method to increase mutagenesis wherein said additional catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain has TREX exonuclease activity, more preferably TREX2 activity. In another preferred embodiment, said catalytic domain is encoded by a single chain TREX polypeptide. Said additional catalytic domain may be fused to the chimeric protein according to the invention optionally by a peptide linker.

Endonucleolytic breaks are known to stimulate the rate of homologous recombination. Therefore, in another preferred embodiment, when a chimeric protein with nuclease activity, such as a TALE-nuclease, is used the present invention relates to a method for inducing homologous gene targeting in the nucleic acid target sequence further comprising providing to the cell an exogeneous nucleic acid comprising at least a sequence homologous to a portion of the nucleic acid target sequence, such that homologous recombination occurs between the nucleic acid target sequence and the exogeneous nucleic acid. Following cleavage of the nucleic acid target sequence, a homologous recombination event is stimulated between the genome containing the nucleic acid target sequence and the exogenous nucleic acid. Preferably, homologous sequences of at least 50 bp, preferably more than 100 bp and more preferably more than 200 bp are used within said exogenous nucleic acid. Therefore, the exogenous nucleic acid is preferably from 200 bp to 6000 bp, more preferably from 1000 bp to 2000 bp. Indeed, shared nucleic acid homologies are located in regions flanking upstream and downstream the site of the cleavage and the nucleic acid sequence to be introduced should be located between the two arms.

In another embodiment, said exogenous nucleic acid comprises two sequences homologous to portions or adjacent portions of said nucleic acid target sequence flanking a sequence to introduce in the nucleic acid target sequence. Particularly, said exogenous nucleic acid comprises first and second portions which are homologous to region 5' and 3' of the nucleic acid target, respectively. Said exogenous nucleic acid in these embodiments can also comprise a third portion positioned between the first and the second portion which comprises no homology with the regions 5' and 3' of the nucleic acid target sequence. In this case, said exogenous sequence allows introducing new genetic material into a cell. Said new genetic material introduced into a cell can confer a selective or a commercial advantage to said cell. In another embodiment, said exogenous sequence allows to replace genetic material into a cell. In another embodiment, said exogenous sequence allows to repair genetic material into a cell.

In particular embodiments, said exogenous nucleic acid can comprise a positive selection marker between the two homology arms and eventually a negative selection marker upstream of the first homology arm or downstream of the second homology arm. The marker(s) allow(s) the selection of the cells having inserted the sequence of interest by homologous recombination at the target site. Depending on the location of the targeted genome sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement.

Cells in which a homologous recombination event has occurred can be selected by methods well-known in the art.

As a non-limiting example, PCR analysis using one oligonucleotide matching within the exogenous nucleic acid sequence and one oligonucleotide matching the genomic nucleic acid of cells outside said exogenous nucleic acid but close to the targeted locus can be performed. Therefore, cells in which methods of the invention allowed a mutagenesis event or a homologous recombination event to occur, can be selected.

In another embodiment, said exogenous sequence to be introduced into a cell can be optimized in order to be not cleavable by the protein used to generate the initial double-stranded break. In other words, in the case where a nucleic acid target sequence has to be corrected by replacement consecutively to a double-stranded break generated by a protein or a chimeric protein according to the present invention, exogenous replacement sequence can be modified in order to be not cleavable again by the original protein or chimeric protein. Said modifications include as non-limiting example silent mutations when targeted sequence is in a coding sequence of a gene or mutations when targeted sequence is in a non-coding sequence of a gene.

In other word, the present invention relates to a method to overcome nucleotide chemical modification sensitivity of a TALE array for binding a DNA target sequence comprising the steps of:
(a) determining a DNA target sequence in the genome of a cell, wherein said DNA target sequence comprises at least one chemically modified nucleic acid base,
(b) synthesizing a nucleic acid encoding a TALE DNA binding domain specific for said
DNA target sequence comprising a plurality of TALE repeat sequences containing each one a Repeat Variable Diresidue region (RVD) which is responsible for the binding of one specific nucleotide in said DNA target sequence wherein said TALE DNA binding domain comprises one or more RVD selected from the group consisting of X* and ** for binding chemically modified nucleic acid base wherein X represents one amino acid residue selected from the group of A, G, V, L, I, M, S, T, C, P, D, E, F, Y, W, Q, N, H, R and K and * represents a gap in one position of the RVD,
(c) introducing said nucleic acid into said cell,
thereby obtaining a nucleic acid encoding a TALE DNA binding domain which binds said DNA target sequence independently of its cytosine methylation status, when expressed in appropriate conditions.

More particularly, the present invention relates to a method for targeting a genetic material in a cell comprising:
(a) Providing a cell containing a target DNA sequence, wherein said DNA target sequence comprises at least one CpG sequence,
(b) Introducing a protein comprising at least one (i) Transcription Activator-Like Effector (TALE) domain wherein said TALE domain comprises a plurality of TALE repeat sequences containing each one a Repeat Variable Diresidue region (RVD) which is responsible for the binding of one specific nucleotide pair in the target DNA sequence wherein said TALE DNA binding domain comprises one or more RVD selected from the group consisting of X* and ** for binding cytosine or 5-methyl-cytosine wherein X represents one amino acid residue selected from the group of A, G, V, L, I, M, S, T, C, P, D, E, F, Y, W, Q, N, H, R and K and * represents a gap in one position of the RVD, (ii) an additional protein domain to process the DNA within or adjacent to the specific DNA target sequence,
such that the TALE domain binds said target DNA sequence independently of its cytosine methylation status, when expressed in appropriate conditions.

As non-limiting example, said protein or chimeric protein can be introduced as a transgene encoded by a plasmidic vector; said plasmidic vector may contain a selection marker which allows to identify and/or select cells which received said vector by method well-known in the art. Said protein expression can be induced in selected cells and said TALE domain of the protein binds target DNA sequence in selected cells, thereby obtaining cells in which TALE domain binds a specific target DNA sequence. In another embodiment, said protein or chimeric protein comprising TALE domain can be directly introduced in cells as a protein by well-known method of the art.

In a preferred embodiment, the present invention relates to a method for modifying the genetic material of a cell comprising:
(a) Providing a cell containing a target DNA sequence, wherein said DNA target sequence comprises at least one CpG sequence,
(b) Introducing a protein comprising at least:
(i) A Transcription Activator-Like Effector (TALE) DNA binding domain specific for a DNA target sequence comprising a plurality of TALE repeat sequences containing each one a Repeat Variable Diresidue region (RVD) which is responsible for the binding of one specific nucleotide pair in said DNA target sequence wherein said TALE DNA binding domain comprises one or more RVD selected from the group consisting of X* and ** for binding cytosine or 5-methyl-cytosine wherein X represents one amino acid residue selected from the group of A, G, V, L, I, M, S, T, C, P, D, E, F, Y, W, Q, N, H, R and K and * represents a gap in one position of the RVD,
(ii) An endonuclease,
such that the TALE DNA binding domain binds said target DNA sequence and the endonuclease generates a double-stranded break within or adjacent to the specific DNA target sequence independently of its cytosine methylation status, when expressed in appropriate conditions.

In a preferred embodiment, the present invention relates to a method for modifying the genetic material of a cell comprising:
(a) Providing a cell containing a target DNA sequence, wherein said DNA target sequence comprises at least one CpG sequence,
(b) Introducing a protein comprising at least:
(i) A Transcription Activator-Like Effector (TALE) DNA binding domain specific for a DNA target sequence comprising a plurality of TALE repeat sequences containing each one a Repeat Variable Diresidue region (RVD) which is responsible for the binding of one specific nucleotide pair in said DNA target sequence wherein said TALE DNA binding domain comprises one or more RVD selected from the group consisting of X*and ** for binding cytosine or 5-methyl-cytosine wherein X represents one amino acid residue selected from the group of A, G, V, L, I, M, S, T, C, P, D, E, F, Y, W, N, H, R and K and * represents a gap in one position of the RVD,
(ii) An endonuclease,
(c) Inducing the expression of the protein of (b);
(d) Selecting the cells in which a double-stranded break within or adjacent to the specific DNA target sequence has occurred.

As a non-limiting example, said protein comprising at least a TALE DNA binding domain fused to an endonuclease can be introduced as a transgene encoded by a plasmidic vector in said provided cell containing a DNA target sequence; said plasmidic vector contains a selection marker which allows to identify and/or select cells which received said vector. Said protein expression can be induced in selected cells and said TALE domain of the protein can bind target DNA sequence in selected cells and fused endonuclease can generate a double-stranded break within or adjacent to the specific DNA target sequence; thereby obtaining cells in which protein comprising at least a TALE DNA binding domain fused to an endonuclease has generated a targeted double-stranded break. Cells in which said protein has been introduced is selected by a selection method well-known in the art.

Cells in which a cleavage-induced mutagenesis event, i.e. a mutagenesis event consecutive to an NHEJ event, has occurred can be identified and/or selected by well-known method in the art. As a non-limiting example, deep-sequencing analysis can be generated from the targeted cell genome around the targeted locus. Insertion/deletion events (mutagenesis events) can be therefore detected. As another non-limiting example, assays based on T7 endonuclease that recognizes non-perfectly matched DNA can be used, to quantify from a locus specific PCR on genomic DNA from provided cells, mismatches between reannealed DNA strands coming from cleaved/non-cleaved DNA molecules.

3. Method to Detect Chemically Modified Base(s)

In another embodiment, the present invention relates to methods to detect the presence of chemically modified nucleic acid base in a nucleic acid target sequence in the genome of a cell.

According to a further aspect, the present invention relates to a method to detect at least one chemically modified nucleic acid base in a nucleic acid target sequence comprising:
(a) binding said nucleic acid target sequence with a transcription activator-like effector (TALE) protein comprising a plurality of TALE-like repeat sequences, each of said sequences comprising a repeat variable-diresidue (RVD) specific to each nucleic acid base of said nucleic acid target sequence wherein at least one RVD is selected from the group consisting of:
HD for recognizing C;
NG for recognizing T;
NI for recognizing A;
NN for recognizing G or A;
NS for recognizing A or C or G or T;
HG for recognizing T;
IG for recognizing T;
NK for recognizing G;
HA for recognizing C;
ND for recognizing C;
HI for recognizing C;
HN for recognizing G;
NA for recognizing G;
SN for recognizing G or A; and
YG for recognizing T;
(b) binding the same nucleic acid target sequence with another transcription activator-like effector (TALE) protein comprising a plurality of TALE-like repeat sequences, similar to that used in step a), wherein at least one RVD has been replaced by a RVD consisting of X* or **, preferably H*, T*, Q* or N*, wherein X represents one amino acid residue selected from the group of A, G, V, L, I, M, S, T, C, P, D, E, F, Y, W, Q, N, H, R and K,
and * represents a gap in one position of the RVD,
(c) determining the binding affinity with said nucleic acid sequence under a) and b),
(d) calculating the ratio of binding activities determined under c), wherein said ratio, when close to 0, indicates the presence of chemically modified nucleic acid base(s) in said nucleic acid target sequence and, when close to 1, the absence of chemically modified nucleic acid base(s) in said nucleic acid target sequence.

In another embodiment, the invention relates to said method wherein the binding affinity is measured (or tested) by a nuclease activity or transcriptional activity. In a preferred embodiment, the invention relates to said method wherein binding affinity is measured by detecting signal of reporter proteins such as fluorescent proteins, fused to said TALE proteins (a) and (b). Said reporter proteins can be luciferase, β-galactosidase, and β-lactamase as non-limiting examples or other reporter proteins which are usable in systems such as split systems known in the art.

More particularly, the present invention also relates to a method to detect the presence of 5-methyl-cytosine in a DNA target sequence in the genome of a cell comprising at least one of the steps of:
(a) determining a first DNA target sequence in the genome of a cell, wherein said first DNA target sequence comprises at least one CpG sequence,
(b) synthesizing a first nucleic acid encoding (i) a TALE array specific for said first DNA target sequence comprising a plurality of TALE repeat sequences containing each one a Repeat Variable Diresidue region (RVD) which is responsible for the binding of one specific nucleotide in said first DNA target sequence wherein said TALE DNA binding domain comprises one or more RVD selected from the group consisting of X* and ** for binding cytosine or 5-methyl-cytosine wherein X represents one amino acid residue selected from the group of A, G, V, L, I, M, S, T, C, P, D, E, F, Y, W, Q, N, H, R and K and * represents a gap in one position of the RVD, (ii) a first subdomain of two of a reporter protein wherein said reporter protein is only active when said first and second subdomains interact,
(c) synthesizing a second nucleic acid encoding (i) a TALE array specific for said first DNA target sequence comprising a plurality of TALE repeat sequences containing each one a Repeat Variable Diresidue region (RVD) which is responsible for the binding of one specific nucleotide in said first DNA target sequence wherein said TALE DNA binding domain comprises one or more RVD HD for binding cytosine, (ii) a first subdomain of two of a reporter protein wherein said reporter protein is only active when said first and second subdomains interact,
(d) synthesizing a third nucleic acid encoding (i) a TALE array specific for a second DNA target sequence adjacent to said first DNA target sequence comprising a plurality of TALE repeat sequences containing each one a Repeat Variable Diresidue region (RVD) which is responsible for the binding of one specific nucleotide in said DNA target sequence, (ii) a second subdomain of two of a reporter protein wherein said reporter protein is only active when said first and second subdomains interact,
(e) introducing said first and third nucleic acids into said cell, thereby obtaining a first and a third nucleic acids encoding TALE arrays which bind said first and second DNA target sequences when expressed in appropriate conditions and transmits a reporter protein signal independently of the cytosine methylation status of said first DNA target, (f) introducing said second and third nucleic acids into said cell, thereby obtaining a second and a third nucleic acids encoding TALE arrays which bind said first and second DNA target sequences when expressed in appropriate conditions and transmits a reporter protein signal when 5-methyl-cytosine is absent of said first DNA target, (g) determining a ratio: reporter protein signal of (f)/reporter protein signal of (e), wherein said ratio, when close to 0, indicates the presence of 5-methyl cytosine in said first DNA target sequence and wherein said ratio, when close to 1, indicates the absence of 5-methyl cytosine in said first DNA target sequence, thereby obtaining the methylation status of the at least one CpG sequence comprised in said first DNA target sequence.

In another embodiment, when two CpGs are present in said first and second DNA target sequences, respectively, in the genome of a cell, the present invention relates to a method to detect the methylation status of each CpGs comprising at least one of the steps of:

(a) synthesizing a first nucleic acid encoding (i) a TALE array specific for said first DNA target sequence comprising a plurality of TALE repeat sequences containing each one a Repeat Variable Diresidue region (RVD) which is responsible for the binding of one specific nucleotide in said first DNA target sequence wherein said TALE DNA binding domain comprises one or more RVD selected from the group consisting of X* and ** for binding cytosine or 5-methyl-cytosine wherein X represents one amino acid residue selected from the group of A, G, V, L, I, M, S, T, C, P, D, E, F, Y, W, Q, N, H, R and K and * represents a gap in one position of the RVD, (ii) a first subdomain of two of a reporter protein wherein said reporter protein is only active when said first and second subdomains interact, (b) synthesizing a second nucleic acid encoding (i) a TALE array specific for said first DNA target sequence comprising a plurality of TALE repeat sequences containing each one a Repeat Variable Diresidue region (RVD) which is responsible for the binding of one specific nucleotide in said first DNA target sequence wherein said TALE DNA binding domain comprises one or more RVD HD for binding cytosine, (ii) a first subdomain of two of a reporter protein wherein said reporter protein is only active when said first and second subdomains interact, (c) synthesizing a third nucleic acid encoding (i) a TALE array specific for said second DNA target sequence comprising a plurality of TALE repeat sequences containing each one a Repeat Variable Diresidue region (RVD) which is responsible for the binding of one specific nucleotide in said second DNA target sequence wherein said TALE DNA binding domain comprises one or more RVD selected from the group consisting of X* and ** for binding cytosine or 5-methyl-cytosine wherein X represents one amino acid residue selected from the group of A, G, V, L, I, M, S, T, C, P, D, E, F, Y, W, Q, N, H, R and K and * represents a gap in one position of the RVD, (ii) a second subdomain of two of a reporter protein wherein said reporter protein is only active when said first and second subdomains interact, (d) synthesizing a fourth nucleic acid encoding (i) a TALE array specific for said second DNA target sequence comprising a plurality of TALE repeat sequences containing each one a Repeat Variable Diresidue region (RVD) which is responsible for the binding of one specific nucleotide in said second DNA target sequence wherein said TALE DNA binding domain comprises one or more RVD HD for binding cytosine, (ii) a second subdomain of two of a reporter protein wherein said reporter protein is only active when said first and second subdomains interact, (e) introducing said first and third nucleic acids into said cell, thereby obtaining a first and a third nucleic acids encoding TALE arrays which bind said first and second DNA target sequences when expressed in appropriate conditions and transmits a reporter protein signal independently of the cytosine methylation status of said first DNA target, (f) introducing said second and third nucleic acids into said cell, thereby obtaining a second and a third nucleic acids encoding TALE arrays which bind said first and second DNA target sequences when expressed in appropriate conditions and transmits a reporter protein signal when 5-methyl-cytosine is absent of said first DNA target, (g) introducing said first and fourth nucleic acids into said cell, thereby obtaining a first and a fourth nucleic acids encoding TALE arrays which bind said first and second DNA target sequences when expressed in appropriate conditions and transmits a reporter protein signal when 5-methyl-cytosine is absent of said second DNA target, (h) determining a ratio: reporter protein signal of (f)/reporter protein signal of (e), wherein said ratio, when close to 0, indicates the presence of 5-methyl cytosine in said first DNA target sequence and wherein said ratio, when close to 1, indicates the absence of 5-methyl cytosine in said first DNA target sequence.

(i) determining a ratio: reporter protein signal of (g)/reporter protein signal of (e), wherein said ratio, when close to 0, indicates the presence of 5-methyl cytosine in said second DNA target sequence and wherein said ratio, when close to 1, indicates the absence of 5-methyl cytosine in said second DNA target sequence, thereby obtaining the methylation status of the two CpG sequences comprised in said first and second DNA target sequences, respectively.

In another embodiment, said first and second subdomains of a reporter protein according to the present invention can be subdomains of fluorescent proteins, luciferase, β-galactosidase, and β-lactamase as non-limiting examples or other reporter proteins which are usable in systems such as split systems known in the art.

In another embodiment, the cell targeted or modified by the methods of the present invention is a eukaryotic cell preferably a mammalian cell or a plant cell. In another embodiment, the cell targeted or modified by the methods of the present invention is an algae cell.

In another embodiment, the DNA sequence targeted or modified by the methods of the present invention is a chromosomal sequence or an episomal sequence. In another embodiment, said sequence is an organelle sequence.

In another embodiment, said methods of the present invention can be used to generate animals or plants wherein a targeted double-stranded break occurred.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

DNA or nucleic acid processing activity refers to a particular/given enzymatic activity of a protein domain comprised in a chimeric protein or a polypeptide according to the invention such as in the expression "a protein domain to process the nucleic acid within or adjacent to the nucleic acid target sequence". Said DNA or nucleic acid processing activity can refer to a cleavage activity, either a cleavase activity either a nickase activity, more broadly a nuclease activity but also a polymerase activity, a kinase activity, a phosphatase activity, a methylase activity, a topoisomerase activity, an integrase activity, a transposase activity, a ligase, a helicase or recombinase activity as non-limiting examples.

Nucleotides or nucleic acid base are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "peptide linker" or "peptidic linker" it is intended to mean a peptide sequence which allows the connection of different monomers or different parts comprised in a fusion protein such as between a TALE DNA binding domain and a protein domain in a chimeric protein or a polypeptide according to the present invention and which allows the adoption of a correct conformation for said chimeric protein activity and/or specificity. Peptide linkers can be of various sizes, from 3 amino acids to 50 amino acids as a non limiting indicative range. Peptide linkers can also be qualified as structured or unstructured. Peptide linkers can be qualified as active linkers when they comprise active domains that are able to change their structural conformation under appropriate stimulation.

by "subdomain" it is intended a protein subdomain or a protein part that interacts with another protein subdomain or protein part to form an active entity and/or a catalytic active entity bearing nucleic acid or DNA processing activity of said chimeric protein or polypeptide according to the invention.

by "DNA target", "DNA target sequence", "target DNA sequence", "nucleic acid target sequence", "target sequence", or "processing site" is intended a polynucleotide sequence that can be bound and/or processed by a TALE derived protein or chimeric protein according to the present invention. These terms refer to a specific nucleic acid location, preferably a genomic location in a cell, but also a portion of genetic material that can exist independently to the main body of genetic material such as plasmids, episomes, virus, transposons or in organelles such as mitochondria or chloroplasts as non-limiting examples. The nucleic acid target sequence is defined by the 5' to 3' sequence of one strand of said target.

Adjacent is used to qualify the second nucleic acid sequence recognized and bound by a set of specific RVDs comprised in the TALE DNA binding domain of a polypeptide or a chimeric protein according to the present invention, compared to a first nucleic acid sequence recognized and bound by another set of specific RVDs comprised in the TALE DNA binding domain of a polypeptide or a chimeric protein according to the present invention, both sequences possibly surrounds a spacer sequence wherein a protein domain of a chimeric protein according to the present invention, process the targeted DNA spacer. Said nucleic acid sequences can be adjacent and located on a different DNA strand.

By "delivery vector" or "delivery vectors" is intended any delivery vector which can be used in the present invention to put into cell contact (i.e. "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

By "integrative lentiviral vectors (or LV)", is meant such vectors as non limiting example, that are able to integrate the genome of a target cell.

At the opposite by "non integrative lentiviral vectors (or NILV)" is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in Potenza C et al. 2004, In vitro Cell Dev Biol 40:1-22). Inducible promoter may be induced by chemicals (reviewed in (Moore, Samalova et al. 2006); (Padidam 2003); (Wang, Zhou et al. 2003); (Zuo and Chua 2000).

Delivery vectors and vectors can be associated or combined with any cellular permeabilization techniques such as sonoporation or electroporation or derivatives of these techniques.

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*.

More preferably the plant is of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata*.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans*.

In the present invention, the cell can be a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells. Are also encompassed in the scope of the present invention stem cells and induced Pluripotent Stem cells (iPS).

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

In the frame of the present invention, the expression "double-strand break-induced mutagenesis" (DSB-induced mutagenesis) refers to a mutagenesis event consecutive to an NHEJ event following an endonuclease-induced DSB, leading to insertion/deletion at the cleavage site of an endonuclease.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" usually refers to the specific physical location of a polypeptide or chimeric protein's nucleic target sequence on a chromosome. Such a locus can comprise a target sequence that is recognized and/or cleaved by a polypeptide or a chimeric protein according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria or chloroplasts as non-limiting examples.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

By "chimeric protein" according to the present invention is meant any fusion protein comprising at least one RVD to bind a nucleic acid sequence and one protein domain to process a nucleic acid target sequence within or adjacent to said bound nucleic acid sequence.

By "protein domain" is meant the nucleic acid target sequence processing part of said chimeric protein according to the present invention. Said protein domain can provide any catalytical activity as classified and named according to the reaction they catalyze [Enzyme Commission number (EC number) at http://www.chem.qmul.ac.uk/iubmb/enzyme/)]. Said protein domain can be a catalytically active entity by itself. Said protein domain can be a protein subdomain that needs to interact with another protein subdomain to form a dimeric protein domain active entity.

By a "TALE-nuclease" (TALEN) is intended a fusion protein consisting of a DNA-binding domain derived from a Transcription Activator Like Effector (TALE) and one nuclease catalytic domain to cleave a nucleic acid target sequence. Said TALE-nuclease is a subclass of chimeric protein according to the present invention.

by "variant(s)", it is intended a RVD variant, a chimeric protein variant, a DNA binding variant, a TALE-nuclease variant, a polypeptide variant obtained by replacement of at least one residue in the amino acid sequence of the parent molecule.

by "functional mutant" is intended a catalytically active mutant of a protein or a protein domain; such mutant can have the same activity compared to its parent protein or protein domain or additional properties. This definition applies to chimeric proteins or protein domains that constitute chimeric proteins according to the present invention. Are also encompassed in the scope of this definition "derivatives" of these proteins or protein domains that comprise the entirety or part of these proteins or protein domains fused to other proteic or chemical parts such as tags, antibodies, polyethylene glycol as non-limiting examples.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

To investigate the sensitivity of TAL repeats domain to CpG methylation an engineered TAL nuclease model named XPCT1 (or XPC4T3) was specifically designed to bind and cleave xpc1 locus (also named xpc4) (SEQ ID NO: 1) containing one methylated CpG. XPCT1 TALE-nuclease was composed of two independent entities XPCT1L (XPCT4T3.3) and XPCT1R (XPC4T3.4), each containing a TALE-derived DNA binding domain fused to the catalytic domain of the FokI restriction enzyme. XPCT1L and XPCT1R were engineered to bind to two DNA target sequences (Left and Right targets respectively) separated by a 11 bp spacer sequence (xpc1 locus, FIGS. 3A and B). Binding of XPCT1L and XPCT1 R to xpc1 locus was expected to allow FokI to dimerize and create a double-strand break within the spacer.

The abilities of RVD HD and N* to bind to 5-methyl-cytosine located at position +2 of the Left target (FIG. 3A in red) were compared by engineering two variants of XPCT1L containing either RVD HD or RVD N* in position +2 of the TALE repeat stretch (FIG. 3B). Each of these two variants were coupled with their counterpart XPCT1R and the nuclease activity of the resulting TALE-nucleases named XPCT1_HD (XPC4T3_HD) or XPCT1_N* (XPC4T3_N*) was determined according to four different protocols (see Material and Methods section for details).

Briefly, the first and second protocols consisted in determining the nuclease activities of XPCT1_HD and XPCT1_N* in yeast and mammalian cells according to the protocol described respectively in Epinat et al. 2003 and Arnould et al. 2006, using an extrachromosomal target containing the unmethylated xpc1 locus whereas, the third and fourth protocols consisted in determining and comparing their nuclease activities toward the methylated endogenous xpc1 locus in mammalian cells. Nuclease activities were assessed by T7 nuclease assay (6) or by deep sequencing.

Material and Methods

Tal Repeats Array Assembly and Subcloning into Yeast and Mammalian Expression Plasmids The TAL repeats arrays XPCT1L_HD, XPCT1L_N* and XPCT1R (SEQ ID NO: 2, SEQ ID NO: 3 and SEQ ID NO: 4, respectively, encoding SEQ ID NO: 14, SEQ ID NO: 15 and SEQ ID NO: 16) were synthesized using a solid support method consisting in a sequential assembly of TAL repeats through consecutive restriction/ligation/washing steps as shown in FIG. 4. Briefly, as an example, to assemble XPCT1L_HD repeats array, the first TAL repeat (SEQ ID NO: 5 encoding SEQ ID NO: 17) was immobilized on a solid support through biotin/streptavidin interaction, digested by SfaNI type IIS restriction endonuclease and then ligated to a second TAL repeat (SEQ ID NO: 5 encoding SEQ ID NO: 17) harboring SfaNI compatible overhangs at its 5' end (FIG. 4B). The resulting TAL repeats array (i.e. containing TAL repeats 1 and 2) was then used as template for subsequent additions of the appropriate TAL repeats (SEQ ID NO: 6-9, encoding SEQ ID NO: 18-21 for NI, NN, respectively targeting nucleotides A, G and HD, N* respectively targeting nucleotides C) to generate the complete TAL repeats arrays XPCT1L_HD or N* according to the same protocol (FIG. 4C). The complete TAL repeats array was finally digested by SfaNI to generate SfaNI overhangs at its 3' end (FIG. 4D) and then striped of the solid support using BbvI type IIS restriction endonuclease (FIG. 4E). The digested TAL repeats array was recovered and subcloned into yeast or mammalian expression plasmids harboring the Nterminal domain of AvrBs3 TAL effector and the eleven first amino acids of its Cterminal domain fused to FokI type IIS restriction endonuclease (pCLS 7802 and pCLS 11170, i.e. SEQ ID NO: 10 and SEQ ID NO: 11 respectively encoding SEQ ID NO: 22 and SEQ ID NO: 23, FIG. 4F). pCLS7802 was derived from pCLS0542 (SEQ ID NO: 24) using NcoI and XhoI restriction sites and pCLS11170 was derived from pCLS8391 (SEQ ID NO: 25) using NcoI and EagI restriction sites.

Cells Culture and Transfections

Human 293H cells (Life Technologies, Carlsbad, Calif.) and hamster CHO-KI cells (ATCC) were cultured at 37° C. with 5% CO2 in complete medium DMEM or F12-K respectively, supplemented with 2 mM L-glutamine, 100 IU/ml penicillin, 100 µg/ml streptomycin, 0.25 µg/ml amphotericin B (Fongizone, Life Technologies,) and 10% FBS. Concerning the extrachromosomal assays, CHO-KI cells were plated at 2500 cells per well in 96 wells plate. The next day, cells were transfected with an increasing amount of DNA (from 0.04 to 50 ng total) using Polyfect transfection reagent (Qiagen) according to the manufacturer's protocol. Concerning the mutagenesis assays, 293H cells were plated at a density of $1.2 \times 10^6$ cells per 10 cm dish. The next day, cells were transfected with 2, 5 or 10 µg of DNA using Lipofectamine 2000 transfection reagent (Life Technologies) according to the manufacturer's protocol.

Monitoring TALE-Nuclease Extrachromosomal SSA Activity

CHO-KI cells were plated at 2500 cells per well in 96 wells plate. The next day, cells were cotransfected by increasing amounts of DNA encoding XPC TALE-nuclease (from 0 to 25 ng each) and a constant amount of XPC extrachromosomal unmethylated target (75 ng) using polyfect transfection reagent (Qiagen) according to the manufacturer's protocol. TALE-nucleases single strand annealing (SSA) activities were determined according to the protocol described in (19,20).

Monitoring of Targeted Modification Induced by XPCT1 TALE-Nucleases Via Deep Sequencing or T7 Nuclease Assay To evaluate the ability of different XPC TALE-nucleases to induce Targeted Mutagenesis (TM) at their endogenous loci, 293H cells were first plated at a density of $1.2 \times 10^6$ cells per 10 cm dish. The next day, cells were transfected with a total amount of 2, 5 or 10 µg of TALE-nuclease expressing vector or empty vector using Lipofectamine 2000 transfection reagent (Life Technologies) according to the manufacturer's protocol. Two or three days post-transfection, genomic DNA was extracted and the loci of interest were amplified with locus specific primers (respectively XPCMID1_F, SEQ ID NO: 12 and XPC_R, SEQ ID NO: 13) linked to adaptor sequences needed for deep sequencing method. Amplicons were analyzed either by EndoT7 assay according to the protocol described in (21) or by deep sequencing using the 454 system (Life Sciences, an average of 5000 sequences per sample were analyzed).

Results

Our results showed that XPCT1_HD or XPCT1_N* TALE-nucleases displayed similar nuclease activities toward an XPC1 unmethylated extrachromosomal DNA target in yeast and mammalian cells with a slight advantage for XPCT1_HD TALE-nuclease (data not shown and FIG. 5A). In stark contrast, when the two TALE-nucleases were assayed at the endogenous methylated locus, XPCT1_N* was the only one showing detectable nuclease activity as seen by the presence of T7 nuclease digestion band (FIG. 5B, red stars). Accordingly, the frequency of targeted modification (TM) induced by XPCT1_N* was much higher than the one induced by XPCT1_HD TALE-nuclease which was almost undetectable under our best experimental conditions (17.2% and 0.8% respectively, FIG. 5C). Differences of nuclease activity observed between the two TALE-nucleases were not due to variation of transfection efficiency from one TALE-nuclease to another (data not shown). Taken together, our results showed that TAL DNA binding domain using RVD HD to target cytosine are sensitive to cytosine methylation and that such sensitivity can be overcome by substituting RVD HD by RVD N*.

Example 2: Ability of Naturally Occurring TAL Repeats H* and NG to Overcome TAL DNA Binding Domain Sensitivity to 5-Methyl-Cytosine We hypothesized that naturally occurring TAL repeats, other than TAL repeat N*, either lacking the glycine 13 or harboring small side chain residues at the same position, could efficiently bind 5-methyl-cytosine. To confirm this, we assessed the ability of TAL repeats H* and NG to substitute HD in position +2 of XPCT1 TAL DNA binding domain (FIG. 6A) and rescue its activity toward its endogenous methylated locus in 293H cells (SEQ ID NO: 1).
Material and Methods
  Materials
  TALE-nucleases XPCT1L-HD, XPCT1L-N*, XPCT1L-NG, XPCT1L-H* and XPCT1R (SEQ ID NO: 26-30 respectively encoding SEQ ID NO: 38-42) were obtained according to the method described in earlier examples. Active TALE-nucleases were formed by a combination of one "TALE-nuclease L" (XPCT1L-HD, XPCT1L-N*, XPCT1L-NG or XPCT1L-H*) and one "TALE-nuclease R" (XPCT1 R).
  See example 1 for monitoring TALE-nuclease extrachromosomal SSA activity and monitoring of TALE-nuclease-induced Targeted Mutagenesis methods
  Toxicity Assay
  The CHO-KI cell line was transfected in 96 wells plate as described above, with increasing amounts of TALE-nuclease expression vectors and a constant amount of GFP-encoding plasmid. GFP levels were monitored by flow cytometry (Guava EasyCyte, Guava Technologies) 1 and 6 days post-transfection. Cell survival was calculated as a ratio (TALE-nuclease-transfected cells expressing GFP at Day 6/control transfected cells expressing GFP at Day 6). Ratios were corrected for the transfection efficiency determined at Day 1 and plotted as a function of final concentration of DNA transfected. Toxic and non-toxic controls were used in each experiment (19).
Results
  To first control whether substitution of HD to H* and NG affected the intrinsic nuclease activity of XPCT1, we performed a single strand annealing (SSA) assay in Chinese Hamster Ovary (CHO) cells (19), using an unmethylated extrachromosomal XPC1 target (SEQ ID NO: 1) and XPCT1-HD and N* as controls (FIG. 6B). Our results showed that the XPCT1-N* and H* TALE-nucleases (SEQ ID NO: 39 with SEQ ID NO: 42 and SEQ ID NO: 41 with SEQ ID NO: 42) displayed similar SSA activities and was slightly less active than XPCT1-HD (SEQ ID NO: 38 with SEQ ID NO: 42, FIG. 6B). On another hand, XPCT1-NG (SEQ ID NO: 40 with SEQ ID NO: 42) displayed a marked decrease of activity with respect to XPCT1-HD, consistent with the poor ability of NG to recognize cytosine (3,4). We then assessed the ability of these TALE-nucleases to disrupt the endogenous methylated XPC1 target in 293H cells by targeted mutagenesis (TM). TALE-nuclease-induced TM, consisting of small insertion or deletion of nucleotide generated via imprecise non-homologous end joining, was determined by an endoT7 assay and by deep sequencing as described previously (21,22). Our results showed that both TAL repeats H* and NG could rescue XPCT1 activity, with a clear advantage for H*, which was almost as efficient as N* (FIG. 6C). We thus conclude that although small amino acids in position 13 can accommodate 5-methyl-cytosine, complete absence of such amino acids, the hallmark of the TAL repeat "*", leads to more proficient 5-methyl-cytosine recognition.
  We verified that HD to N*, HD to H* or HD to NG substitutions within TAL DNA binding domains of XPCT1L, did not increase TALE-nuclease-induced toxicity in CHO cells using the protocol described by Grizot & al. (19). For all TALE-nucleases tested, we found that the presence of TAL repeats N*, H* or NG in position 2 of the TAL DNA binding domain of XPCT1L, did not influence its toxicity as seen by similar cell survival patterns obtained between HD, N*, H* and NG variants (FIG. 6D)

Example 3: TAL Repeat N*, a Universal 5-Methyl-Cytosine Binding Module

To evaluate the ability of TAL repeat N* to overcome TAL DNA binding domain sensitivity to 5-methyl-cytosine in different contexts (i.e. at other endogenous methylated targets), we engineered two other TALE-nucleases, XPCT2 and XPCT3, specifically designed to process the methylated endogenous XPC targets called XPC2 and XPC3 (SEQ ID NO: 50 and SEQ ID NO: 51). These targets contained respectively one and two 5-methyl-cytosine located at different positions (FIG. 7A), making it possible to evaluate the influence of the number and position of N* repeats in a TAL DNA binding domain.
Material and Methods
  See examples 1 and 2 for methods
  Materials
  TALE-nucleases XPCT2L-HD, XPCT2L-N*, XPCT2R, XPCT3L-HD, XPCT3L-N*, XPCT3R-HD and XPCT3R-N* (SEQ ID NO 31-37 respectively encoding SEQ ID NO: 43-49) were obtained according to the method described in earlier examples. Active TALE-nucleases were formed by a combination of one "TALE-nuclease L" and one "TALE-nuclease R" as described in example 1.
Results
  TALE-nuclease activities of XPCT2-N* and XPCT3-N* (FIG. 7) were determined in 293H cells according to the protocol described in example 1, and then compared to their HD counterparts (FIG. 7B). XPCT1-HD and N* (see example 2) was used as a control in the experiment described below. Our EndoT7 assays showed that N* variants were always the most active, indicating that TAL repeat N* is able to successfully bind 5-methyl-cytosine in different contexts. Interestingly, the basal activities of TALE-nucleases-HD and the fold induction achieved by HD/N* substitution, were different form one TALE-nuclease to another, suggesting that the binding penalty induced by 5-methyl-cytosine depends on its position within TAL DNA binding site.

We verified that HD/N* substitution within TAL DNA binding domains, did not increase TALE-nuclease-induced toxicity in CHO cells using the protocol described by Grizot & al (19). For all TALE-nucleases tested, we found that the presence of single or multiple TAL N* repeats did not influence TALE-nuclease-induced toxicity as seen by similar cell survival patterns obtained between HD and N* variants of XPCT2 and T3 (FIGS. 7C and 7D respectively). In full agreement with their lack of toxicity, TALE-nucleases-N* displayed similar TM frequencies in 293H cells, 3 or 7 days post transfection (data not shown). Consistent with this absence of toxicity, naturally occurring TAL effectors were reported to bear up to 20% of TAL repeat N*50 within their DNA binding domain while retaining high specificity. Therefore, taken together, our results showed that the TAL repeat N* could be used as a universal 5-methyl-cytosine binding module without affecting toxicity of engineered TAL DNA binding domains.

In summary, our work unraveled the hidden cipher governing 5-methyl-cytosine recognition by TAL repeats N*, H* and NG. Based on this finding, we present a simple, efficient and universal method to overcome TALE DNA binding domain sensitivity to cytosine methylation. Such method presents three major advantages. First, it allows one to bypass the need for chemical demethylation of endogenous targets which is unsuitable for cell engineering and therapeutic applications. Second, it is readily applicable to all TAL derived proteins, and in particular, to engineered transcription activators, thus potentially enabling site specific activation of methylated promoters responsible for genes silencing. Third, it is transposable to the broad range of cellular systems including ES, iPS mammalian cells and plant cells that have already been shown to be engineerable with TALE-nuclease technology.

Example 4: Ability of Engineered TAL Repeats T*, Q* and Natural TAL Repeat HG to Overcome TAL DNA Binding Domain Sensitivity to 5-mC We hypothesized that engineered TAL repeats "*", namely T* and Q* and natural TAL repeat HG could efficiently bind 5mC. To confirm this, we assessed the ability of TAL repeats T*, Q* and HG to substitute HD in position +2 of XPCT1 TAL DNA binding domain and to rescue its activity toward its endogenous methylated locus in 293H cells.

Material and Methods

See examples 1 to 3 for methods

TALE-nucleases XPCT1L-T*, XPCT1L-Q*, XPCT1L-HG and XPCT1R (SEQ ID NO: 52, 53, 54, and 30 respectively encoding SEQ ID NO: 55, 56, 57 and 42) were obtained according to the method described in earlier examples or else, by de novo gene synthesis. Active TALE-nucleases were formed by a combination of one "TALE-nuclease L" (XPCT1L-T*, XPCT1L-Q* or XPCT1L-HG) and one "TALE-nuclease R" (XPCT1 R). The nuclease activity of TALE-nucleases XPCT1L-HD, N*, NG, and H* (SEQ ID NO: 26-29 respectively encoding SEQ ID NO: 38-41) were also determined and used here as control experiments See example 1 for a comprehensive description of the monitoring of TALE-nuclease-induced Targeted Mutagenesis.

Results

TALE-nuclease activities of XPCT1L-T*, XPCT1L-Q* and XPCT1L-HG were determined in 293H cells according to the protocol described in example 1, and then compared to their HD counterparts (FIG. 8). XPCT1L-HD, N*, NG, and H* (SEQ ID NO: 26-29 respectively encoding SEQ ID NO: 38-41, see example 2) were used as controls in the experiment described below. Our Deep sequencing results showed that T*, and Q* variants were more active than the HD variant, indicating that TAL repeat T*, Q* and HG can bind 5-methyl-Cytosine more efficiently than does HD. Thus, TAL repeat T*, Q* and HG could be potentially used to design TALE-nuclease targeting methylated endogenous loci.

LIST OF CITED REFERENCES

1. Baker, M. Gene-editing nucleases. Nat Methods 9, 23-6 (2012)
2. Bogdanove, A. J. & Voytas, D. F. TAL effectors: customizable proteins for DNA targeting. Science 333, 1843-6 (2011).
3. Boch, J. et al. Breaking the code of DNA binding specificity of TAL-type III effectors. Science 326, 1509-12 (2009).
4. Moscou, M. J. & Bogdanove, A. J. A simple cipher governs DNA recognition by TAL effectors. Science 326, 1501 (2009).
5. Zhang, F. et al. Efficient construction of sequence-specific TAL effectors for modulating mammalian transcription. Nat Biotechnol 29, 149-53 (2011).
6. Miller, J. C. et al. A TALE nuclease architecture for efficient genome editing. Nat Biotechnol 29, 143-8 (2011).
7. Huang, P. et al. Heritable gene targeting in zebrafish using customized TALENs. Nat Biotechnol 29, 699-700 (2011).
8. Sander, J. D. et al. Targeted gene disruption in somatic zebrafish cells using engineered TALENs. Nat Biotechnol 29, 697-8 (2011).
9. Li, T. et al. Modularly assembled designer TAL effector nucleases for targeted gene knockout and gene replacement in eukaryotes. Nucleic Acids Res 39, 6315-25 (2011).
10. Jaenisch, R. & Bird, A. Epigenetic regulation of gene expression: how the genome integrates intrinsic and environmental signals. Nat Genet 33 Suppl, 245-54 (2003).
11. Ziller, M. J. et al. Genomic distribution and inter-sample variation of non-CpG methylation across human cell types. Plos Genet 7(12):e1002389 (2011)
12. Mak, A. N., Bradley, P., Cernadas, R. A., Bogdanove, A. J. & Stoddard, B. L. The crystal structure of TAL effector PthXo1 bound to its DNA target. Science 335, 716-9 (2012).
13. Epinat, J. C. et al. A novel engineered meganuclease induces homologous recombination in yeast and mammalian cells. Nucleic Acids Res 31(11): 2952-62 (2003).
14. Arnould, S. et al. Engineering of large numbers of highly specific homing endonucleases that induce recombination on novel DNA targets. J Mol Biol 355(3): 443-58 (2006).
15. Grizot, S. et al. Generation of redesigned homing endonucleases comprising DNA-binding domains derived from two different scaffolds. Nucleic Acids Res 38(6): 2006-18 (2009).
16. Bogdanove, A. J., S. Schornack, et al. TAL effectors: finding plant genes for disease and defense. Curr Opin Plant Biol 13(4): 394-401 (2010).
17. Chames, P., J. C. Epinat, et al. In vivo selection of engineered homing endonucleases using double-strand break induced homologous recombination. Nucleic Acids Res 33(20): e178 (2005).
18. Smith, J., S. Grizot, et al. A combinatorial approach to create artificial homing endonucleases cleaving chosen sequences. Nucleic Acids Res (2006).

19. Grizot, S., Smith, J. et al. Efficient targeting of a SCID gene by an engineered single-chain homing endonuclease. Nucleic Acids Res 37(16): 5405-19 (2009)
20. Daboussi, F., Zaslayskiy, M. et al. Chromosomal context and epigenetic mechanisms control the efficacy of genome editing by rare-cutting designer endonucleases. Nucleic Acids Res, Epub ahead of print (2012)
21. Reyon, D., Tsai, S. Q. et al. FLASH assembly of TALENs for high-throughput genome editing. Nat Biotechnol 30(5): 460-5 (2012)
22. Mussolino, C., Morbitzer, R. et al. A novel TALE nuclease scaffold enables high genome editing activity in combination with low toxicity. Nucleic Acids Res 39(21): 9283-93 (2011)
23. Weber, E., Gruetzner, R. et al. Assembly of designer TAL effectors by Golden Gate cloning. Plos One 6, e19722 (2011).
24. Morbitzer, R. Elsaesser, J. et al. Assembly of custom ALE-type DNA binding domains by modular cloning. Nucleic Acids Res 39, 5790-5799 (2011)

The invention claimed is:

1. A method to process a nucleic acid target sequence comprising a 5-methyl-cytosine comprising:
   (a) providing cells containing a nucleic acid target sequence that comprises a 5-methyl-cytosine;
   (b) introducing into said cell a polynucleotide comprising:
      (i) a first polynucleotide encoding a transcription activator-like effector (TALE) protein comprising a plurality of TALE-like repeat sequences, each repeat comprising a repeat variable-diresidue (RVD) specific to each nucleic acid base of said nucleic acid target sequence, wherein the RVD that specifically targets the 5-methyl-cytosine within said nucleic acid target sequence is selected from N*, T*, Q* and H*, wherein * represents a gap in one position of the RVD; and
      (ii) a second polynucleotide encoding an additional protein domain that has a nuclease activity, polymerase activity, kinase activity, phosphatase activity, methylase activity, topoisomerase activity, integrase activity, transposase activity, ligase activity, helicase activity or a recombinase activity;
   (c) expressing said polynucleotide to form a chimeric protein that binds said nucleic acid target sequence and processes the nucleic acid within or adjacent to said nucleic acid target sequence and,
   (d) selecting the cells in which said TALE protein has processed said nucleic acid target sequence within or adjacent to said nucleic acid target sequence;
   wherein the TALE protein comprising an RVD N*, T*, Q* or H* that specifically targets the 5-methyl-cytosine can bind said nucleic acid target sequence more efficiently than a variant TALE protein having the RVD NG at the same position.

2. The method according to claim 1, wherein said nucleic acid target sequence comprises at least one methylated CpG dinucleotide.

3. The method according to claim 1, wherein said nucleic acid target sequence comprises at least one methylated CpA dinucleotide.

4. The method according to claim 1, wherein said nucleic acid target sequence comprises at least one methylated CpT dinucleotide.

5. The method according to claim 1, wherein said nucleic acid target sequence comprises at least one methylated CpC dinucleotide.

6. The method according to claim 1, wherein the RVD that specifically targets the 5-methyl-cytosine within said nucleic acid target sequence is N*.

7. The method according to claim 1, wherein the RVD that specifically targets the 5-methyl-cytosine within said nucleic acid target sequence is T*.

8. The method according to claim 1, wherein the RVD that specifically targets the 5-methyl-cytosine within said nucleic acid target sequence is Q*.

9. The method according to claim 1, wherein the RVD that specifically targets the 5-methyl-cytosine within said nucleic acid target sequence is H*.

10. The method according to claim 1, wherein said nucleic acid target sequence is a methylated promoter sequence.

11. The method according to claim 6, wherein said additional protein domain is an endonuclease.

12. The method according to claim 7, wherein said additional protein domain is an endonuclease.

13. The method according to claim 8, wherein said additional protein domain is an endonuclease.

14. The method according to claim 9, wherein said additional protein domain is an endonuclease.

15. The method according to claim 1, further comprising providing to the cell an exogenous nucleic acid comprising a sequence homologous to at least a portion of the nucleic acid target sequence, such that homologous recombination occurs between the nucleic acid target sequence and the exogenous nucleic acid.

16. The method according to claim 1, wherein said chimeric protein is a TALE-nuclease that comprises an amino acid sequence selected from the group consisting of SEQ ID NO: 39, 41, 44, 47, and 49.

* * * * *

SEQUENCE LISTING

```
<160> NUMBER OF SEQ ID NOS: 57

<210> SEQ ID NO 1
<211> LENGTH: 45
<212> TYPE: DNA
<213> ORGANISM: artificial sequence
<220> FEATURE:
<223> OTHER INFORMATION: xpc1 locus

<400> SEQUENCE: 1
tccgagatgt cacacagagg tacgacccag tctggatgac agtga            45

<210> SEQ ID NO 2
<211> LENGTH: 1590
<212> TYPE: DNA
<213> ORGANISM: artificial sequence
<220> FEATURE:
<223> OTHER INFORMATION: XPCT1L_HD

<400> SEQUENCE: 2
ttgaccccgg agcaggtggt ggccatcgcc agccacgatg gcggcaagca ggcgctggag      60
acggtccagc ggctgttgcc ggtgctgtgc caggcccacg gcttgacccc ggagcaggtg     120
gtggccatcg ccagccacga tggcggcaag caggcgctgg agacggtcca gcggctgttg     180
ccggtgctgt gccaggccca cggcttgacc ccccagcagg tggtggccat cgccagcaat     240
aatggtggca agcaggcgct ggagacggtc cagcggctgt tgccggtgct gtgccaggcc     300
cacggcttga ccccggagca ggtggtggcc atcgccagca atattggtgg caagcaggcg     360
ctggagacgg tgcaggcgct gttgccggtg ctgtgccagg cccacggctt gaccccccag     420
caggtggtgg ccatcgccag caataatggt ggcaagcagg cgctggagac ggtccagcgg     480
ctgttgccgg tgctgtgcca ggcccacggc ttgaccccgg agcaggtggt ggccatcgcc     540
agcaatattg tggcaagca ggcgctggag acggtgcagg cgctgttgcc ggtgctgtgc      600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat aatggtggca agcaggcgct ggagacggtc     780
cagcggctgt tgccggtgct gtgccaggcc cacggcttga ccccccagca ggtggtggcc     840
atcgccagca atggcggtgg caagcaggcg ctggagacgg tccagcggct gttgccggtg     900
ctgtgccagg cccacggctt gaccccggag caggtggtgg ccatcgccag ccacgatggc     960
ggcaagcagg cgctggagac ggtccagcgg ctgttgccgg tgctgtgcca ggcccacggc    1020
ttgaccccgg agcaggtggt ggccatcgcc agcaatattg tggcaagca ggcgctggag     1080 acggtgcagg cgctgttgcc ggtgctgtgc caggcccacg gcttgacccc ggagcaggtg    1140
gtggccatcg ccagccacga tggcggcaag caggcgctgg agacggtcca gcggctgttg    1200
ccggtgctgt gccaggccca cggcttgacc ccggagcagg tggtggccat cgccagcaat    1260
```

| | |
|---|---:|
| attggtggca agcaggcgct ggagacggtg caggcgctgt tgccggtgct gtgccaggcc | 1320 |
| cacggcttga ccccggagca ggtggtggcc atcgccagcc acgatggcgg caagcaggcg | 1380 |
| ctggagacgg tccagcggct gttgccggtg ctgtgccagg cccacggctt gaccccggag | 1440 |
| caggtggtgg ccatcgccag caatattggt ggcaagcagg cgctggagac ggtgcaggcg | 1500 |
| ctgttgccgg tgctgtgcca ggcccacggc ttgacccctc agcaggtggt ggccatcgcc | 1560 |
| agcaatggcg gcggcaggcc ggcgctggag | 1590 |

```
<210> SEQ ID NO 3
<211> LENGTH: 1587
<212> TYPE: DNA
<213> ORGANISM: artificial sequence
<220> FEATURE:
<223> OTHER INFORMATION: XPCT1L_N*

<400> SEQUENCE: 3
```

| | |
|---|---:|
| ttgaccccgg agcaggtggt ggccatcgcc agccacgatg gcggcaagca ggcgctggag | 60 |
| acggtccagc ggctgttgcc ggtgctgtgc caggcccacg gcttgacccc ggagcaggtg | 120 |
| gtggccatcg ccagcaatgg tggcaagcag gcgctggaga cggtccagcg gctgttgccg | 180 |
| gtgctgtgcc aggcccacgg cttgaccccc agcaggtgg tggccatcgc cagcaataat | 240 |
| ggtggcaagc aggcgctgga cggtccag cggctgttgc cggtgctgtg ccaggcccac | 300 |
| ggcttgaccc cggagcaggt ggtggccatc gccagcaata ttggtggcaa gcaggcgctg | 360 |
| gagacggtgc aggcgctgtt gccggtgctg tgccaggccc acggcttgac ccccagcag | 420 |
| gtggtggcca tcgccagcaa taatggtggc aagcaggcgc tggagacggt ccagcggctg | 480 |
| ttgccggtgc tgtgccaggc ccacggcttg accccggagc aggtggtggc catcgccagc | 540 |
| aatattggtg gcaagcaggc gctggagacg gtgcaggcgc tgttgccggt gctgtgccag | 600 |
| gcccacggct tgacccccca gcaggtggtg gccatcgcca gcaatggcgg tggcaagcag | 660 |
| gcgctggaga cggtccagcg gctgttgccg gtgctgtgcc aggcccacgg cttgaccccc | 720 |
| cagcaggtgg tggccatcgc cagcaataat ggtggcaagc aggcgctgga cggtccag | 780 |
| cggctgttgc cggtgctgtg ccaggcccac ggcttgaccc ccagcaggt ggtggccatc | 840 |
| gccagcaatg gcggtggcaa gcaggcgctg gagacggtcc agcggctgtt gccggtgctg | 900 |
| tgccaggccc acggcttgac cccggagcag gtggtggcca tcgccagcca cgatggcggc | 960 |
| aagcaggcgc tggagacggt ccagcggctg ttgccggtgc tgtgccaggc ccacggcttg | 1020 |
| accccggagc aggtggtggc catcgccagc aatattggtg gcaagcaggc gctggagacg | 1080 |
| gtgcaggcgc tgttgccggt gctgtgccag gcccacggct tgaccccgga gcaggtggtg | 1140 |
| gccatcgcca gccacgatgg cggcaagcag gcgctggaga cggtccagcg gctgttgccg | 1200 |
| gtgctgtgcc aggcccacgg cttgaccccg agcaggtgg tggccatcgc cagcaatatt | 1260 |
| ggtggcaagc aggcgctgga cggtcag gcgctgttgc cggtgctgtg ccaggcccac | 1320 |
| ggcttgaccc cggagcaggt ggtggccatc gccagccacg atggcggcaa gcaggcgctg | 1380 |
| gagacggtcc agcggctgtt gccggtgctg tgccaggccc acggcttgac cccggagcag | 1440 |
| gtggtggcca tcgccagcaa tattggtggc aagcaggcgc tggagacggt gcaggcgctg | 1500 |
| ttgccggtgc tgtgccaggc ccacggcttg acccctcagc aggtggtggc catcgccagc | 1560 |
| aatggcggcg caggccggc gctggag | 1587 |

```
<210> SEQ ID NO 4
<211> LENGTH: 1590
```

<212> TYPE: DNA
<213> ORGANISM: artificial sequence
<220> FEATURE:
<223> OTHER INFORMATION: XPCT1R

<400> SEQUENCE: 4

```
ttgaccccgg agcaggtggt ggccatcgcc agccacgatg cggcaagca ggcgctggag      60
acggtccagc ggctgttgcc ggtgctgtgc caggcccacg gcttgacccc ggagcaggtg     120
gtggccatcg ccagcaatat tggtggcaag caggcgctgg agacggtgca ggcgctgttg     180
ccggtgctgt gccaggccca cggcttgacc ccggagcagg tggtggccat cgccagccac     240
gatggcggca agcaggcgct ggagacggtc agcggctgt tgccggtgct gtgccaggcc     300
cacggcttga ccccccagca ggtggtggcc atcgccagca atggcggtgg caagcaggcg     360
ctggagacgg tccagcggct gttgccggtg ctgtgccagg cccacggctt gaccccccag     420
caggtggtgg ccatcgccag caataatggt ggcaagcagg cgctggagac ggtccagcgg     480
ctgttgccgg tgctgtgcca ggcccacggc ttgaccccc agcaggtggt ggccatcgcc     540
agcaatggcg gtggcaagca ggcgctggag acggtccagc ggctgttgcc ggtgctgtgc     600
caggcccacg gcttgacccc ggagcaggtg gtggccatcg ccagccacga tgcggcaag     660
caggcgctgg agacggtcca gcggctgttg ccggtgctgt gccaggccca cggcttgacc     720
ccggagcagg tggtggccat cgccagcaat attggtggca agcaggcgct ggagacggtg     780
caggcgctgt tgccggtgct gtgccaggcc cacggcttga ccccccagca ggtggtggcc     840
atcgccagca atggcggtgg caagcaggcg ctggagacgg tccagcggct gttgccggtg     900
ctgtgccagg cccacggctt gaccccggag caggtggtgg ccatcgccag ccacgatggc     960
ggcaagcagg cgctggagac ggtccagcgg ctgttgccgg tgctgtgcca ggcccacggc    1020
ttgaccccgg agcaggtggt ggccatcgcc agccacgatg cggcaagca ggcgctggag    1080
acggtccagc ggctgttgcc ggtgctgtgc caggcccacg gcttgacccc ggagcaggtg    1140
gtggccatcg ccagcaatat tggtggcaag caggcgctgg agacggtgca ggcgctgttg    1200
ccggtgctgt gccaggccca cggcttgacc cccagcagg tggtggccat cgccagcaat    1260
aatggtggca agcaggcgct ggagacggtc agcggctgt tgccggtgct gtgccaggcc    1320
cacggcttga ccccggagca ggtggtggcc atcgccagca atattggtgg caagcaggcg    1380
ctggagacgg tgcaggcgct gttgccggtg ctgtgccagg cccacggctt gaccccggag    1440
caggtggtgg ccatcgccag ccacgatggc ggcaagcagg cgctggagac ggtccagcgg    1500
ctgttgccgg tgctgtgcca ggcccacggc ttgaccctc agcaggtggt ggccatcgcc    1560
agcaatggcg gcggcaggcc ggcgctggag                                     1590
```

<210> SEQ ID NO 5
<211> LENGTH: 170
<212> TYPE: DNA
<213> ORGANISM: artificial sequence
<220> FEATURE:
<223> OTHER INFORMATION: TALE Repeat HD

<400> SEQUENCE: 5

```
ggccggacgg gccgacgtcc gcagcgacat gttgaccccg agcaggtgg tggccatcgc      60
cagccacgat ggcggcaagc aggcgctgga gacggtccag cggctgttgc cggtgctgtg     120
ccaggcccac ggcttgaccc tcgagatgcg gtaccggggc cactgggcc                 170
```

<210> SEQ ID NO 6

```
<211> LENGTH: 170
<212> TYPE: DNA
<213> ORGANISM: artificial sequence
<220> FEATURE:
<223> OTHER INFORMATION: TALE Repeat NI

<400> SEQUENCE: 6
ggccggacgg gccgacgtcc gcagcgacat gttgaccccg gagcaggtgg tggccatcgc    60
cagcaatatt ggtggcaagc aggcgctgga gacggtgcag gcgctgttgc cggtgctgtg   120
ccaggcccac ggcttgaccc tcgagatgcg gtaccggggc cactggggcc                170

<210> SEQ ID NO 7
<211> LENGTH: 170
<212> TYPE: DNA
<213> ORGANISM: artificial sequence
<220> FEATURE:
<223> OTHER INFORMATION: TALE Repeat NN

<400> SEQUENCE: 7
ggccggacgg gccgacgtcc gcagcgacat gttgaccccc cagcaggtgg tggccatcgc    60
cagcaataat ggtggcaagc aggcgctgga gacggtccag cggctgttgc cggtgctgtg   120
ccaggcccac ggcttgaccc tcgagatgcg gtaccggggc cactggggcc                170

<210> SEQ ID NO 8
<211> LENGTH: 170
<212> TYPE: DNA
<213> ORGANISM: artificial sequence
<220> FEATURE:
<223> OTHER INFORMATION: TALE Repeat HG

<400> SEQUENCE: 8
ggccggacgg gccgacgtcc gcagcgacat gttgaccccg gagcaggtgg tggccatcgc    60
cagccacggc ggcggcaagc aggcgctgga gacggtccag cggctgttgc cggtgctgtg   120
ccaggcccac ggcttgaccc tcgagatgcg gtaccggggc cactggggcc                170

<210> SEQ ID NO 9
<211> LENGTH: 167
<212> TYPE: DNA
<213> ORGANISM: artificial sequence
<220> FEATURE:
<223> OTHER INFORMATION: TALE Repeat N*

<400> SEQUENCE: 9
ggccggacgg gccgacgtcc gcagcgacat gttgaccccg gagcaggtgg tggccatcgc    60
cagcaatggt ggcaagcagg cgctggagac ggtccagcgg ctgttgccgg tgctgtgcca   120
ggcccacggc ttgaccctcg agatgcggta ccggggccac tggggcc                  167

<210> SEQ ID NO 10
<211> LENGTH: 1584
<212> TYPE: DNA
<213> ORGANISM: artificial sequence
<220> FEATURE:
<223> OTHER INFORMATION: pCLS7802

<400> SEQUENCE: 10
atggccgacc ccattcgttc gcgcacacca gtcctgcccg cgagcttct gcccggaccc     60 caacccgatg gggttcagcc gactgcagat cgtggggtgt ctccgcctgc cggcggcccc   120
ctggatggct tgccggctcg gcggacgatg tcccggaccc ggctgccatc tcccctgcc    180 ccctcacctg cgttctcggc gggcagcttc agtgacctgt tacgtcagtt cgatccgtca   240
```

```
cttttaata catcgctttt tgattcattg cctcccttcg gcgctcacca tacagaggct      300
gccacaggcg agtgggatga ggtgcaatcg ggtctgcggg cagccgacgc ccccccaccc      360
accatgcgcg tggctgtcac tgccgcgcgg ccccgcgcg ccaagccggc gccgcgacga      420
cgtgctgcgc aaccctccga cgcttcgccg gcggcgcagg tggatctacg cacgctcggc      480
tacagccagc agcaacagga gaagatcaaa ccgaaggttc gttcgacagt ggcgcagcac      540
cacgaggcac tggtcggcca cgggtttaca cacgcgcaca tcgttgcgtt aagccaacac      600
ccggcagcgt tagggaccgt cgctgtcaag tatcaggaca tgatcgcagc gttgccagag      660
gcgacacacg aagcgatcgt tggcgtcggc aaacagtggt ccggcgcacg cgctctggag      720
gccttgctca cggtggcggg agagttgaga ggtccaccgt tacagttgga cacaggccaa      780
cttctcaaga ttgcaaaacg tggcggcgtg accgcagtgg aggcagtgca tgcatggcgc      840
aatgcactga cgggtgcccc gctcaacttg accggagacg cccggggat caggtcacgt      900 gcgtctcgga gcattgttgc ccagttatct cgccctgatc cgagtggcag cggaagtggc      960
ggggatccta tcagccgttc ccagctggtg aagtccgagc tggaggagaa gaaatccgag     1020
ttgaggcaca agctgaagta cgtgccccac gagtacatcg agctgatcga gatcgcccgg     1080
aacagcaccc aggaccgtat cctggagatg aaggtgatgg agttcttcat gaaggtgtac     1140
ggctacaggg gcaagcacct gggcggctcc aggaagcccg acggcgccat ctacaccgtg     1200
ggctccccca tcgactacgg cgtgatcgtg gacaccaagg cctactccgg cggctacaac     1260
ctgcccatcg gccaggccga cgaaatgcag aggtacgtgg aggagaacca gaccaggaac     1320
aagcacatca ccccaacga gtggtggaag gtgtaccccc tccagcgtga ccgagttcaag     1380 ttcctgttcg tgtccggcca cttcaagggc aactacaagg cccagctgac caggctgaac     1440
cacatcacca actgcaacgg cgccgtgctg tccgtggagg agctcctgat cggcggcgag     1500
atgatcaagg ccggcacccct gaccctggag gaggtgagga ggaagttcaa caacggcgag     1560
atcaacttcg cggccgactg ataa                                             1584
```

<210> SEQ ID NO 11
<211> LENGTH: 1653
<212> TYPE: DNA
<213> ORGANISM: artificial sequence
<220> FEATURE:
<223> OTHER INFORMATION: pCLS11170

<400> SEQUENCE: 11

```
atgggcgatc ctaaaaagaa acgtaaggtc atcgattacc catacgatgt tccagattac       60
gctatcgata tcgccgaccc cattcgttcg cgcacaccaa gtcctgcccg cgagcttctg      120
cccggacccc aacccgatgg ggttcagccg actgcagatc gtggggtgtc tccgcctgcc      180
ggcggccccc tggatggctt gccggctcgg cggacgatgt cccggacccg gctgccatct      240 cccccctgccc cctcacctgc gttctcggcg ggcagcttca gtgacctgtt acgtcagttc      300
gatccgtcac ttttaatac atcgcttttt gattcattgc ctcccttcgg cgctcaccat       360
acagaggctg ccacaggcga gtgggatgag gtgcaatcgg gtctgcgggc agccgacgcc      420
cccccaccca ccatgcgcgt ggctgtcact gccgcgcggc cccgcgcgc caagccggcg      480 ccgcgacgac gtgctgcgca accctccgac gcttcgccgg cggcgcaggt ggatctacgc      540
acgctcggct acagccagca gcaacaggag aagatcaaac cgaaggttcg ttcgacagtg      600
gcgcagcacc acgaggcact ggtcggccac gggtttacac acgcgcacat cgttgcgtta      660
```

```
agccaacacc cggcagcgtt agggaccgtc gctgtcaagt atcaggacat gatcgcagcg    720
ttgccagagg cgacacacga agcgatcgtt ggcgtcggca aacagtggtc ggcgcacgc    780 gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga ccggagacgc ccggggatc    960 aggtcacgtg cgtctcggag cattgttgcc cagttatctc gccctgatcc gagtggcagc   1020
ggaagtggcg gggatcctat cagccgttcc cagctggtga agtccgagct ggaggagaag   1080
aaatccgagt tgaggcacaa gctgaagtac gtgccccacg agtacatcga gctgatcgag   1140
atcgcccgga acagcaccca ggaccgtatc ctggagatga aggtgatgga gttcttcatg   1200
aaggtgtacg gctacagggg caagcacctg ggcggctcca ggaagcccga cggcgccatc   1260
tacaccgtgg gctcccccat cgactacggc gtgatcgtgg acaccaaggc ctactccggc   1320
ggctacaacc tgcccatcgg ccaggccgac gaaatgcaga ggtacgtgga ggagaaccag   1380
accaggaaca agcacatcaa ccccaacgag tggtggaagg tgtacccctc cagcgtgacc   1440
gagttcaagt cctgttcgt gtccggccac ttcaagggca actacaaggc ccagctgacc   1500
aggctgaacc acatcaccaa ctgcaacggc gccgtgctgt ccgtggagga gctcctgatc   1560
ggcggcgaga tgatcaaggc cggcaccctg accctggagg aggtgaggag gaagttcaac   1620
aacggcgaga tcaacttcgc ggccgactga taa                                1653

<210> SEQ ID NO 12
<211> LENGTH: 62
<212> TYPE: DNA
<213> ORGANISM: artificial sequence
<220> FEATURE:
<223> OTHER INFORMATION: XPCMID1_F

<400> SEQUENCE: 12
ccatctcatc cctgcgtgtc tccgactcag acgagtgcgt aagaggcaag aaaatgtgca    60
gc                                                                   62

<210> SEQ ID NO 13
<211> LENGTH: 54
<212> TYPE: DNA
<213> ORGANISM: artificial sequence
<220> FEATURE:
<223> OTHER INFORMATION: XPC_R

<400> SEQUENCE: 13
cctatcccct gtgtgccttg gcagtctcag gctgggcata tataaggtgc tcaa          54

<210> SEQ ID NO 14
<211> LENGTH: 530
<212> TYPE: PRT
<213> ORGANISM: artificial sequence
<220> FEATURE:
<223> OTHER INFORMATION: XPCT1L_HD

<400> SEQUENCE: 14

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45
```

-continued

```
Gly Lys Gln Ala Leu Glu Thr Val Gln Arg Leu Leu Pro Val Leu Cys
 50                  55                  60
Gln Ala His Gly Leu Thr Pro Gln Gln Val Val Ala Ile Ala Ser Asn
 65                  70                  75                  80
Asn Gly Gly Lys Gln Ala Leu Glu Thr Val Gln Arg Leu Leu Pro Val
                 85                  90                  95
Leu Cys Gln Ala His Gly Leu Thr Pro Glu Gln Val Val Ala Ile Ala
            100                 105                 110
Ser Asn Ile Gly Gly Lys Gln Ala Leu Glu Thr Val Gln Ala Leu Leu
        115                 120                 125
Pro Val Leu Cys Gln Ala His Gly Leu Thr Pro Gln Gln Val Val Ala
130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser Asn Ile Gly Gly Lys Gln Ala Leu Glu Thr Val
            180                 185                 190
Gln Ala Leu Leu Pro Val Leu Cys Gln Ala His Gly Leu Thr Pro Gln
        195                 200                 205
Gln Val Val Ala Ile Ala Ser Asn Gly Gly Gly Lys Gln Ala Leu Glu
210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Gly Gly Gly Lys
        275                 280                 285
Gln Ala Leu Glu Thr Val Gln Arg Leu Leu Pro Val Leu Cys Gln Ala
290                 295                 300
His Gly Leu Thr Pro Glu Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
450                 455                 460
Gln Arg Leu Leu Pro Val Leu Cys Gln Ala His Gly Leu Thr Pro Glu
```

```
                465                 470                 475                 480
Gln Val Val Ala Ile Ala Ser Asn Ile Gly Gly Lys Gln Ala Leu Glu
                    485                 490                 495

Thr Val Gln Ala Leu Leu Pro Val Leu Cys Gln Ala His Gly Leu Thr
                500                 505                 510

Pro Gln Gln Val Val Ala Ile Ala Ser Asn Gly Gly Arg Pro Ala
            515                 520                 525

Leu Glu
    530

<210> SEQ ID NO 15
<211> LENGTH: 529
<212> TYPE: PRT
<213> ORGANISM: artificial sequence
<220> FEATURE:
<223> OTHER INFORMATION: XPCT1L_N*

<400> SEQUENCE: 15

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Gly Gly
        35                  40                  45

Lys Gln Ala Leu Glu Thr Val Gln Arg Leu Leu Pro Val Leu Cys Gln
    50                  55                  60

Ala His Gly Leu Thr Pro Gln Gln Val Val Ala Ile Ala Ser Asn Asn
65                  70                  75                  80

Gly Gly Lys Gln Ala Leu Glu Thr Val Gln Arg Leu Leu Pro Val Leu
                85                  90                  95

Cys Gln Ala His Gly Leu Thr Pro Glu Gln Val Val Ala Ile Ala Ser
            100                 105                 110

Asn Ile Gly Gly Lys Gln Ala Leu Glu Thr Val Gln Ala Leu Leu Pro
        115                 120                 125

Val Leu Cys Gln Ala His Gly Leu Thr Pro Gln Gln Val Val Ala Ile
130                 135                 140

Ala Ser Asn Asn Gly Gly Lys Gln Ala Leu Glu Thr Val Gln Arg Leu
145                 150                 155                 160

Leu Pro Val Leu Cys Gln Ala His Gly Leu Thr Pro Glu Gln Val Val
                165                 170                 175

Ala Ile Ala Ser Asn Ile Gly Gly Lys Gln Ala Leu Glu Thr Val Gln
            180                 185                 190

Ala Leu Leu Pro Val Leu Cys Gln Ala His Gly Leu Thr Pro Gln Gln
        195                 200                 205

Val Val Ala Ile Ala Ser Asn Gly Gly Gly Lys Gln Ala Leu Glu Thr
    210                 215                 220

Val Gln Arg Leu Leu Pro Val Leu Cys Gln Ala His Gly Leu Thr Pro
225                 230                 235                 240

Gln Gln Val Val Ala Ile Ala Ser Asn Asn Gly Gly Lys Gln Ala Leu
                245                 250                 255

Glu Thr Val Gln Arg Leu Leu Pro Val Leu Cys Gln Ala His Gly Leu
            260                 265                 270

Thr Pro Gln Gln Val Val Ala Ile Ala Ser Asn Gly Gly Gly Lys Gln
        275                 280                 285

Ala Leu Glu Thr Val Gln Arg Leu Leu Pro Val Leu Cys Gln Ala His
```

-continued

```
            290                 295                 300
Gly Leu Thr Pro Glu Gln Val Ala Ile Ala Ser His Asp Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Glu Gln Val Val Ala Ile Ala Ser Asn Ile
                340                 345                 350

Gly Gly Lys Gln Ala Leu Glu Thr Val Gln Ala Leu Leu Pro Val Leu
                355                 360                 365

Cys Gln Ala His Gly Leu Thr Pro Glu Gln Val Val Ala Ile Ala Ser
        370                 375                 380

His Asp Gly Gly Lys Gln Ala Leu Glu Thr Val Gln Arg Leu Leu Pro
385                 390                 395                 400

Val Leu Cys Gln Ala His Gly Leu Thr Pro Glu Gln Val Val Ala Ile
                405                 410                 415

Ala Ser Asn Ile Gly Gly Lys Gln Ala Leu Glu Thr Val Gln Ala Leu
                420                 425                 430

Leu Pro Val Leu Cys Gln Ala His Gly Leu Thr Pro Glu Gln Val Val
                435                 440                 445

Ala Ile Ala Ser His Asp Gly Gly Lys Gln Ala Leu Glu Thr Val Gln
        450                 455                 460

Arg Leu Leu Pro Val Leu Cys Gln Ala His Gly Leu Thr Pro Glu Gln
465                 470                 475                 480

Val Val Ala Ile Ala Ser Asn Ile Gly Gly Lys Gln Ala Leu Glu Thr
                485                 490                 495

Val Gln Ala Leu Leu Pro Val Leu Cys Gln Ala His Gly Leu Thr Pro
                500                 505                 510

Gln Gln Val Val Ala Ile Ala Ser Asn Gly Gly Gly Arg Pro Ala Leu
                515                 520                 525

Glu

<210> SEQ ID NO 16
<211> LENGTH: 530
<212> TYPE: PRT
<213> ORGANISM: artificial sequence
<220> FEATURE:
<223> OTHER INFORMATION: XPCT1R

<400> SEQUENCE: 16

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
                115                 120                 125
```

```
Pro Val Leu Cys Gln Ala His Gly Leu Thr Pro Gln Gln Val Val Ala
    130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Gln Gln Val
                165                 170                 175
Val Ala Ile Ala Ser Asn Gly Gly Lys Gln Ala Leu Glu Thr Val
            180                 185                 190
Gln Arg Leu Leu Pro Val Leu Cys Gln Ala His Gly Leu Thr Pro Glu
        195                 200                 205
Gln Val Val Ala Ile Ala Ser His Asp Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Glu Gln Val Val Ala Ile Ala Ser Asn Ile Gly Gly Lys Gln Ala
                245                 250                 255
Leu Glu Thr Val Gln Ala Leu Leu Pro Val Leu Cys Gln Ala His Gly
                260                 265                 270
Leu Thr Pro Gln Gln Val Val Ala Ile Ala Ser Asn Gly Gly Gly Lys
            275                 280                 285
Gln Ala Leu Glu Thr Val Gln Arg Leu Leu Pro Val Leu Cys Gln Ala
    290                 295                 300
His Gly Leu Thr Pro Glu Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser His
                340                 345                 350
Asp Gly Gly Lys Gln Ala Leu Glu Thr Val Gln Arg Leu Leu Pro Val
            355                 360                 365
Leu Cys Gln Ala His Gly Leu Thr Pro Glu Gln Val Val Ala Ile Ala
    370                 375                 380
Ser Asn Ile Gly Gly Lys Gln Ala Leu Glu Thr Val Gln Ala Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
                420                 425                 430
Leu Leu Pro Val Leu Cys Gln Ala His Gly Leu Thr Pro Glu Gln Val
            435                 440                 445
Val Ala Ile Ala Ser Asn Ile Gly Gly Lys Gln Ala Leu Glu Thr Val
    450                 455                 460
Gln Ala Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Gly Arg Pro Ala
            515                 520                 525
Leu Glu
    530
```

<210> SEQ ID NO 17
<211> LENGTH: 34
<212> TYPE: PRT
<213> ORGANISM: artificial sequence
<220> FEATURE:
<223> OTHER INFORMATION: TALE Repeat HD

<400> SEQUENCE: 17

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 18
<211> LENGTH: 34
<212> TYPE: PRT
<213> ORGANISM: artificial sequence
<220> FEATURE:
<223> OTHER INFORMATION: TALE Repeat NI

<400> SEQUENCE: 18

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly

<210> SEQ ID NO 19
<211> LENGTH: 34
<212> TYPE: PRT
<213> ORGANISM: artificial sequence
<220> FEATURE:
<223> OTHER INFORMATION: TALE Repeat NN

<400> SEQUENCE: 19

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 20
<211> LENGTH: 34
<212> TYPE: PRT
<213> ORGANISM: artificial sequence
<220> FEATURE:
<223> OTHER INFORMATION: TALE Repeat HG

<400> SEQUENCE: 20

Leu Thr Pro Glu Gln Val Val Ala Ile Ala Ser His Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 21
<211> LENGTH: 33
<212> TYPE: PRT
<213> ORGANISM: artificial sequence
<220> FEATURE:
<223> OTHER INFORMATION: TALE Repeat N*

<400> SEQUENCE: 21

Leu Thr Pro Glu Gln Val Val Ala Ile Ala Ser Asn Gly Gly Lys Gln
1               5                   10                  15

Ala Leu Glu Thr Val Gln Arg Leu Leu Pro Val Leu Cys Gln Ala His
            20                  25                  30

Gly

<210> SEQ ID NO 22
<211> LENGTH: 526
<212> TYPE: PRT
<213> ORGANISM: artificial sequence
<220> FEATURE:
<223> OTHER INFORMATION: pCLS7802

<400> SEQUENCE: 22

Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
            20                  25                  30

Val Ser Pro Pro Ala Gly Gly Pro Leu Asp Gly Leu Pro Ala Arg Arg
        35                  40                  45

Thr Met Ser Arg Thr Arg Leu Pro Ser Pro Pro Ala Pro Ser Pro Ala
    50                  55                  60

Phe Ser Ala Gly Ser Phe Ser Asp Leu Leu Arg Gln Phe Asp Pro Ser
65                  70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Thr Met Arg Val Ala Val Thr Ala
        115                 120                 125

Ala Arg Pro Pro Arg Ala Lys Pro Ala Pro Arg Arg Arg Ala Ala Gln
    130                 135                 140

Pro Ser Asp Ala Ser Pro Ala Ala Gln Val Asp Leu Arg Thr Leu Gly
145                 150                 155                 160

Tyr Ser Gln Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190

His Ile Val Ala Leu Ser Gln His Pro Ala Ala Leu Gly Thr Val Ala
        195                 200                 205

Val Lys Tyr Gln Asp Met Ile Ala Ala Leu Pro Glu Ala Thr His Glu
    210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
                245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
        275                 280                 285

Asn Leu Thr Gly Asp Ala Arg Gly Ile Arg Ser Arg Ala Ser Arg Ser
    290                 295                 300

Ile Val Ala Gln Leu Ser Arg Pro Asp Pro Ser Gly Ser Gly Ser Gly

```
            305                 310                 315                 320
Gly Asp Pro Ile Ser Arg Ser Gln Leu Val Lys Ser Glu Leu Glu Glu
                    325                 330                 335
Lys Lys Ser Glu Leu Arg His Lys Leu Lys Tyr Val Pro His Glu Tyr
            340                 345                 350
Ile Glu Leu Ile Glu Ile Ala Arg Asn Ser Thr Gln Asp Arg Ile Leu
        355                 360                 365
Glu Met Lys Val Met Glu Phe Phe Met Lys Val Tyr Gly Tyr Arg Gly
370                 375                 380
Lys His Leu Gly Gly Ser Arg Lys Pro Asp Gly Ala Ile Tyr Thr Val
385                 390                 395                 400
Gly Ser Pro Ile Asp Tyr Gly Val Ile Val Asp Thr Lys Ala Tyr Ser
                    405                 410                 415
Gly Gly Tyr Asn Leu Pro Ile Gly Gln Ala Asp Glu Met Gln Arg Tyr
            420                 425                 430
Val Glu Glu Asn Gln Thr Arg Asn Lys His Ile Asn Pro Asn Glu Trp
        435                 440                 445
Trp Lys Val Tyr Pro Ser Ser Val Thr Glu Phe Lys Phe Leu Phe Val
450                 455                 460
Ser Gly His Phe Lys Gly Asn Tyr Lys Ala Gln Leu Thr Arg Leu Asn
465                 470                 475                 480
His Ile Thr Asn Cys Asn Gly Ala Val Leu Ser Val Glu Glu Leu Leu
                    485                 490                 495
Ile Gly Gly Glu Met Ile Lys Ala Gly Thr Leu Thr Leu Glu Glu Val
            500                 505                 510
Arg Arg Lys Phe Asn Asn Gly Glu Ile Asn Phe Ala Ala Asp
        515                 520                 525

<210> SEQ ID NO 23
<211> LENGTH: 549
<212> TYPE: PRT
<213> ORGANISM: artificial sequence
<220> FEATURE:
<223> OTHER INFORMATION: pCLS11170

<400> SEQUENCE: 23

Met Gly Asp Pro Lys Lys Lys Arg Lys Val Ile Asp Tyr Pro Tyr Asp
1               5                   10                  15
Val Pro Asp Tyr Ala Ile Asp Ile Ala Asp Pro Ile Arg Ser Arg Thr
            20                  25                  30
Pro Ser Pro Ala Arg Glu Leu Leu Pro Gly Pro Gln Pro Asp Gly Val
        35                  40                  45
Gln Pro Thr Ala Asp Arg Gly Val Ser Pro Pro Ala Gly Gly Pro Leu
    50                  55                  60
Asp Gly Leu Pro Ala Arg Arg Thr Met Ser Arg Thr Arg Leu Pro Ser
65                  70                  75                  80
Pro Pro Ala Pro Ser Pro Ala Phe Ser Ala Gly Ser Phe Ser Asp Leu
                85                  90                  95
Leu Arg Gln Phe Asp Pro Ser Leu Phe Asn Thr Ser Leu Phe Asp Ser
            100                 105                 110
Leu Pro Pro Phe Gly Ala His His Thr Glu Ala Ala Thr Gly Glu Trp
        115                 120                 125
Asp Glu Val Gln Ser Gly Leu Arg Ala Ala Asp Ala Pro Pro Pro Thr
    130                 135                 140
Met Arg Val Ala Val Thr Ala Ala Arg Pro Pro Arg Ala Lys Pro Ala
```

```
            145                 150                 155                 160
Pro Arg Arg Arg Ala Ala Gln Pro Ser Asp Ala Ser Pro Ala Ala Gln
                165                 170                 175
Val Asp Leu Arg Thr Leu Gly Tyr Ser Gln Gln Gln Glu Lys Ile
                180                 185                 190
Lys Pro Lys Val Arg Ser Thr Val Ala Gln His His Glu Ala Leu Val
                195                 200                 205
Gly His Gly Phe Thr His Ala His Ile Val Ala Leu Ser Gln His Pro
                210                 215                 220
Ala Ala Leu Gly Thr Val Ala Val Lys Tyr Gln Asp Met Ile Ala Ala
225                 230                 235                 240
Leu Pro Glu Ala Thr His Glu Ala Ile Val Gly Val Gly Lys Gln Trp
                245                 250                 255
Ser Gly Ala Arg Ala Leu Glu Ala Leu Leu Thr Val Ala Gly Glu Leu
                260                 265                 270
Arg Gly Pro Pro Leu Gln Leu Asp Thr Gly Gln Leu Leu Lys Ile Ala
                275                 280                 285
Lys Arg Gly Gly Val Thr Ala Val Glu Ala Val His Ala Trp Arg Asn
                290                 295                 300
Ala Leu Thr Gly Ala Pro Leu Asn Leu Thr Gly Asp Ala Arg Gly Ile
305                 310                 315                 320
Arg Ser Arg Ala Ser Arg Ser Ile Val Ala Gln Leu Ser Arg Pro Asp
                325                 330                 335
Pro Ser Gly Ser Gly Ser Gly Asp Pro Ile Ser Arg Ser Gln Leu
                340                 345                 350
Val Lys Ser Glu Leu Glu Glu Lys Ser Glu Leu Arg His Lys Leu
                355                 360                 365
Lys Tyr Val Pro His Glu Tyr Ile Glu Leu Ile Glu Ile Ala Arg Asn
                370                 375                 380
Ser Thr Gln Asp Arg Ile Leu Glu Met Lys Val Met Glu Phe Phe Met
385                 390                 395                 400
Lys Val Tyr Gly Tyr Arg Gly Lys His Leu Gly Gly Ser Arg Lys Pro
                405                 410                 415
Asp Gly Ala Ile Tyr Thr Val Gly Ser Pro Ile Asp Tyr Gly Val Ile
                420                 425                 430
Val Asp Thr Lys Ala Tyr Ser Gly Gly Tyr Asn Leu Pro Ile Gly Gln
                435                 440                 445
Ala Asp Glu Met Gln Arg Tyr Val Glu Glu Asn Gln Thr Arg Asn Lys
450                 455                 460
His Ile Asn Pro Asn Glu Trp Trp Lys Val Tyr Pro Ser Ser Val Thr
465                 470                 475                 480
Glu Phe Lys Phe Leu Phe Val Ser Gly His Phe Lys Gly Asn Tyr Lys
                485                 490                 495
Ala Gln Leu Thr Arg Leu Asn His Ile Thr Asn Cys Asn Gly Ala Val
                500                 505                 510
Leu Ser Val Glu Glu Leu Leu Ile Gly Gly Glu Met Ile Lys Ala Gly
                515                 520                 525
Thr Leu Thr Leu Glu Glu Val Arg Arg Lys Phe Asn Asn Gly Glu Ile
                530                 535                 540
Asn Phe Ala Ala Asp
545

<210> SEQ ID NO 24
```

<211> LENGTH: 8334
<212> TYPE: DNA
<213> ORGANISM: artificial sequence
<220> FEATURE:
<223> OTHER INFORMATION: pCLS0542

<400> SEQUENCE: 24

| | | | | | |
|---|---|---|---|---|---|
| tgtgtgcggc | cgactgataa | ctcgagcgat | cctctagacg | agctcctcga | gcctgcagca | 60 |
| gctgaagctt | tggacttctt | cgccagaggt | ttggtcaagt | ctccaatcaa | ggttgtcggc | 120 |
| ttgtctacct | tgccagaaat | ttacgaaaag | atggaaaagg | gtcaaatcgt | tggtagatac | 180 |
| gttgttgaca | cttctaaata | agcgaatttc | ttatgattta | tgattttat | tattaaataa | 240 |
| gttataaaaa | aaataagtgt | atacaaattt | taaagtgact | cttaggtttt | aaaacgaaaa | 300 |
| ttcttattct | tgagtaactc | tttcctgtag | gtcaggttgc | tttctcaggt | atagcatgag | 360 |
| gtcgctctta | ttgaccacac | ctctaccggc | atgcaagctt | ggcgtaatca | tggtcatagc | 420 |
| tgtttcctgt | gtgaaattgt | tatccgctca | caattccaca | caacatacga | gccggaagca | 480 |
| taaagtgtaa | agcctggggt | gcctaatgag | tgagctaact | cacattaatt | gcgttgcgct | 540 |
| cactgcccgc | tttccagtcg | ggaaacctgt | cgtgccagca | gatctattac | attatgggtg | 600 |
| gtatgttgga | ataaaaatca | actatcatct | actaactagt | atttacgtta | ctagtatatt | 660 |
| atcatatacg | gtgttagaag | atgacgcaaa | tgatgagaaa | tagtcatcta | aattagtgga | 720 |
| agctgaaacg | caaggattga | taatgtaata | ggatcaatga | atattaacat | ataaaatgat | 780 |
| gataataata | tttatagaat | tgtgtagaat | tgcagattcc | cttttatgga | ttcctaaatc | 840 |
| ctcgaggaga | acttctagta | tatctacata | cctaatatta | ttgccttatt | aaaaatggaa | 900 |
| tcccaacaat | tacatcaaaa | tccacattct | cttcaaaatc | aattgtcctg | tacttccttg | 960 |
| ttcatgtgtg | ttcaaaaacg | ttatatttat | aggataatta | tactctatt | ctcaacaagt | 1020 |
| aattggttgt | ttggccgagc | ggtctaaggc | gcctgattca | agaaatatct | tgaccgcagt | 1080 |
| taactgtggg | aatactcagg | tatcgtaaga | tgcaagagtt | cgaatctctt | agcaaccatt | 1140 |
| attttttttcc | tcaacataac | gagaacacac | aggggcgcta | tcgcacagaa | tcaaattcga | 1200 |
| tgactggaaa | ttttttgtta | atttcagagg | tcgcctgacg | catataacctt | tttcaactga | 1260 |
| aaaattggga | gaaaaaggaa | aggtgagagc | cgcggaaccg | gcttttcata | tagaatagag | 1320 |
| aagcgttcat | gactaaatgc | ttgcatcaca | atacttgaag | ttgacaatat | tatttaagga | 1380 |
| cctattgttt | tttccaatag | gtggttagca | atcgtcttac | tttctaactt | ttcttacctt | 1440 |
| ttacatttca | gcaatatata | tatatatatt | tcaaggatat | accattctaa | tgtctgcccc | 1500 |
| taagaagatc | gtcgttttgc | caggtgacca | cgttggtcaa | gaaatcacag | ccgaagccat | 1560 |
| taaggttctt | aaagctattt | ctgatgttcg | ttccaatgtc | aagttcgatt | tcgaaaatca | 1620 |
| tttaattggt | ggtgctgcta | tcgatgctac | aggtgtccca | cttccagatg | aggcgctgga | 1680 |
| agcctccaag | aaggttgatg | ccgttttgtt | aggtgctgtg | ggtggtccta | aatgggtac | 1740 |
| cggtagtgtt | agacctgaac | aaggtttact | aaaaatccgt | aaagaacttc | aattgtacgc | 1800 |
| caacttaaga | ccatgtaact | ttgcatccga | ctctcttta | gacttatctc | caatcaagcc | 1860 |
| acaatttgct | aaaggtactg | acttcgttgt | tgtcagagaa | ttagtgggag | gtatttactt | 1920 |
| tggtaagaga | aaggaagacg | atggtgatgg | tgtcgcttgg | gatagtgaac | aatacaccgt | 1980 |
| tccagaagtg | caaagaatca | caagaatggc | cgctttcatg | ccctacaac | atgagccacc | 2040 |
| attgcctatt | tggtccttgg | ataaagctaa | tgttttggcc | tcttcaagat | tatggagaaa | 2100 |
| aactgtggag | gaaaccatca | agaacgaatt | ccctacattg | aaggttcaac | atcaattgat | 2160 |

```
tgattctgcc gccatgatcc tagttaagaa cccaacccac ctaaatggta ttataatcac    2220
cagcaacatg tttggtgata tcatctccga tgaagcctcc gttatcccag gttccttggg    2280
tttgttgcca tctgcgtcct tggcctcttt gccagacaag aacaccgcat ttggtttgta    2340
cgaaccatgc cacggttctg ctccagattt gccaaagaat aaggtcaacc ctatcgccac    2400
tatcttgtct gctgcaatga tgttgaaatt gtcattgaac ttgcctgaag aaggtaaggc    2460
cattgaagat gcagttaaaa aggttttgga tgcaggtatc agaactggtg atttaggtgg    2520
ttccaacagt accacggaag tcggtgatgc tgtcgccgaa gaagttaaga aaatccttgc    2580
ttaaaaagat tctcttttttt tatgatattt gtacataaac tttataaatg aaattcataa    2640
tagaaacgac acgaaattac aaaatggaat atgttcatag ggtagacgaa actatatacg    2700
caatctacat acatttatca agaaggagaa aaggaggat gtaaaggaat acaggtaagc     2760
aaattgatac taatggctca acgtgataag gaaaagaat tgcactttaa cattaatatt     2820
gacaaggagg agggcaccac acaaaaagtt aggtgtaaca gaaaatcatg aaactatgat    2880
tcctaattta tatattggag gattttctct aaaaaaaaaa aaatacaaca aataaaaaac    2940
actcaatgac ctgaccattt gatggagttt aagtcaatac cttcttgaac catttcccat    3000
aatggtgaaa gttccctcaa gaattttact ctgtcagaaa cggccttaac gacgtagtcg    3060
acctcctctt cagtactaaa tctaccaata ccaaatctga tggaagaatg ggctaatgca    3120
tcatccttac ccagcgcatg taaaacataa gaaggttcta gggaagcaga tgtacaggct    3180
gaacccgagg ataatgcgat atcccttagt gccatcaata aagattctcc ttccacgtag    3240
gcgaaagaaa cgttaacaca ccctggataa cgatgatctg gagatccgtt caacgtggta    3300
tgttcagcgg ataatagacc tttgactaat ttatcggata gtcttttgat gtgagcttgg    3360
tcgttgtcaa attctttctt catcaatctc gcagcttcac caaatcccgc taccaatggg    3420
ggggccaaag taccagatct gctgcattaa tgaatcggcc aacgcgcggg gagaggcggt    3480
ttgcgtattg ggcgctcttc cgcttcctcg ctcactgact cgctgcgctc ggtcgttcgg    3540
ctgcggcgag cggtatcagc atcgatgaat tccacggact atagactata ctagtatact    3600
ccgtctactg tacgatacac ttccgctcag gtccttgtcc tttaacgagg ccttaccact    3660
cttttgttac tctattgatc cagctcagca aaggcagtgt gatctaagat tctatcttcg    3720
cgatgtagta aaactagcta gaccgagaaa gagactagaa atgcaaaagg cacttctaca    3780
atggctgcca tcattattat ccgatgtgac gctgcagctt ctcaatgata ttcgaatacg    3840 cttttgaggag atacagccta atatccgaca aactgtttta cagatttacg atcgtacttg    3900
ttacccatca ttgaattttg aacatccgaa cctgggagtt ttccctgaaa cagatagtat    3960
atttgaacct gtataataat atatagtcta gcgctttacg gaagacaatg tatgtatttc    4020
ggttcctgga gaaactattg catctattgc ataggtaatc ttgcacgtcg catccccggt    4080
tcattttctg cgtttccatc ttgcacttca atagcatatc tttgttaacg aagcatctgt    4140
gcttcatttt gtagaacaaa atgcaacgc gagagcgcta atttttcaaa caaagaatct     4200
gagctgcatt tttacagaac agaaatgcaa cgcgaaagcg ctattttacc aacgaagaat    4260
ctgtgcttca ttttttgtaaa acaaaaatgc aacgcgagag cgctaatttt tcaaacaaag    4320
aatctgagct gcattttttac agaacagaaa tgcaacgcga gagcgctatt ttaccaacaa    4380
agaatctata cttcttttttt gttctacaaa aatgcatccc gagagcgcta ttttttctaac    4440 aaagcatctt agattacttt ttttctcctt tgtgcgctct ataatgcagt ctcttgataa    4500
```

```
cttttttgcac tgtaggtccg ttaaggttag aagaaggcta ctttggtgtc tattttctct    4560
tccataaaaa aagcctgact ccacttcccg cgtttactga ttactagcga agctgcgggt    4620
gcattttttc aagataaagg catccccgat tatattctat accgatgtgg attgcgcata    4680
ctttgtgaac agaaagtgat agcgttgatg attcttcatt ggtcagaaaa ttatgaacgg    4740
tttcttctat tttgtctcta tatactacgt ataggaaatg tttacatttt cgtattgttt    4800
tcgattcact ctatgaatag ttcttactac aatttttttg tctaaagagt aatactagag    4860
ataaacataa aaaatgtaga ggtcgagttt agatgcaagt tcaaggagcg aaaggtggat    4920
gggtaggtta tagggata tagcacagag atatatagca aagagatact tttgagcaat    4980
gtttgtggaa gcggtattcg caatatttta gtagctcgtt acagtccggt gcgttttttgg    5040 ttttttgaaa gtgcgtcttc agagcgcttt tggttttcaa aagcgctctg aagttcctat    5100
actttctaga aataggaac ttcggaatag aacttcaaa gcgtttccga aaacgagcgc    5160
ttccgaaaat gcaacgcgag ctgcgcacat acagctcact gttcacgtcg cacctatatc    5220
tgcgtgttgc ctgtatatat atatacatga gaagaacggc atagtgcgtg tttatgctta    5280
aatgcgtact tatatgcgtc tatttatgta ggatgaaagg tagtctagta cctcctgtga    5340
tattatccca ttccatgcgg ggtatcgtat gcttccttca gcactaccct ttagctgttc    5400
tatatgctgc cactcctcaa ttggattagt ctcatccttc aatgctatca tttcctttga    5460
tattggatca tatgcatagt accgagaaac tagtgcgaag tagtgatcag gtattgctgt    5520
tatctgatga gtatacgttg tcctggccac ggcagaagca cgcttatcgc tccaatttcc    5580
cacaacatta gtcaactccg ttaggcccctt cattgaaaga aatgaggtca tcaaatgtct    5640
tccaatgtga gattttgggc cattttttat agcaaagatt gaataaggcg cattttttctt    5700 caaagcttta ttgtacgatc tgactaagtt atcttttaat aattggtatt cctgtttatt    5760
gcttgaagaa ttgccggtcc tatttactcg ttttaggact ggttcagaat tcatcgatgc    5820
tcactcaaag gtcggtaata cggttatcca cagaatcagg ggataacgca ggaaagaaca    5880
tgtgagcaaa aggccagcaa aaggccagga accgtaaaaa ggccgcgttg ctggcgtttt    5940
tccataggct ccgcccccct gacgagcatc acaaaaatcg acgctcaagt cagaggtggc    6000
gaaacccgac aggactataa agataccagg cgtttccccc tggaagctcc ctcgtgcgct    6060
ctcctgttcc gaccctgccg cttaccggat acctgtccgc cttctcccct tcgggaagcg    6120
tggcgctttc tcatagctca cgctgtaggt atctcagttc ggtgtaggtc gttcgctcca    6180
agctgggctg tgtgcacgaa ccccccgttc agcccgaccg ctgcgcctta tccggtaact    6240
atcgtcttga gtccaacccg gtaagacacg acttatcgcc actggcagca gccactggta    6300
acaggattag cagagcgagg tatgtaggcg gtgctacaga gttcttgaag tggtggccta    6360
actacggcta cactagaagg acagtatttg gtatctgcgc tctgctgaag ccagttacct    6420
tcggaaaaag agttggtagc tcttgatccg gcaaacaaac caccgctggt agcggtggtt    6480
tttttgtttg caagcagcag attacgcgca gaaaaaaagg atctcaagaa gatcctttga    6540
tcttttctac ggggtctgac gctcagtgga acgaaaactc acgttaaggg attttggtca    6600
tgagattatc aaaaaggatc ttcacctaga tccttttaaa ttaaaaatga agttttaaat    6660
caatctaaag tatatatgag taaacttggt ctgacagtta ccaatgctta atcagtgagg    6720
cacctatctc agcgatctgt ctatttcgtt catccatagt tgcctgactc cccgtcgtgt    6780
agataactac gatacgggag ggcttaccat ctggccccag tgctgcaatg ataccgcgag    6840
acccacgctc accggctcca gatttatcag caataaacca gccagccgga agggccgagc    6900
```

```
gcagaagtgg tcctgcaact ttatccgcct ccatccagtc tattaattgt tgccgggaag    6960
ctagagtaag tagttcgcca gttaatagtt tgcgcaacgt tgttgccatt gctacaggca    7020
tcgtggtgtc acgctcgtcg tttggtatgg cttcattcag ctccggttcc caacgatcaa    7080
ggcgagttac atgatccccc atgttgtgca aaaaagcggt tagctccttc ggtcctccga    7140
tcgttgtcag aagtaagttg gccgcagtgt tatcactcat ggttatggca gcactgcata    7200
attctcttac tgtcatgcca tccgtaagat gcttttctgt gactggtgag tactcaacca    7260
agtcattctg agaatagtgt atgcggcgac cgagttgctc ttgcccggcg tcaatacggg    7320
ataataccgc gccacatagc agaactttaa aagtgctcat cattggaaaa cgttcttcgg    7380
ggcgaaaact ctcaaggatc ttaccgctgt tgagatccag ttcgatgtaa cccactcgtg    7440
cacccaactg atcttcagca tcttttactt tcaccagcgt ttctgggtga gcaaaaacag    7500
gaaggcaaaa tgccgcaaaa aagggaataa gggcgacacg gaaatgttga atactcatac    7560
tcttcctttt tcaatattat tgaagcattt atcagggtta ttgtctcatg agcggataca    7620
tatttgaatg tatttagaaa aataaacaaa taggggttcc gcgcacattt ccccgaaaag    7680
tgccacctga cgtccgatca aaaatcatcg cttcgctgat taattacccc agaaataagg    7740
ctaaaaaact aatcgcatta tcatcctatg gttgttaatt tgattcgttc atttgaaggt    7800
ttgtggggcc aggttactgc caattttttcc tcttcataac cataaaagct agtattgtag    7860
aatctttatt gttcggagca gtgcggcgcg aggcacatct gcgtttcagg aacgcgaccg    7920
gtgaagacga ggacgcacgg aggagagtct ccttcggag gctgtcacc cgctcggcgg    7980 cttctaatcc gtacttcaat atagcaatga gcagttaagc gtattactga aagttccaaa    8040
gagaaggttt ttttaggcta atcgacctcg agcagatccg ccaggcgtgt atatagcgtg    8100
gatggccagg caactttagt gctgacacat acaggcatat atatatgtgt gcgacgacac    8160
atgatcatat ggcatgcatg tgctctgtat gtatataaaa ctcttgtttt cttcttttct    8220
ctaaatattc tttccttata cattaggtcc tttgtagcat aaattactat acttctatag    8280
acacgcaaac acaaatacac agcggccttg ccaccatggc cggcgcgccc acta         8334
```

<210> SEQ ID NO 25
<211> LENGTH: 4905
<212> TYPE: DNA
<213> ORGANISM: artificial sequence
<220> FEATURE:
<223> OTHER INFORMATION: pCLS8391

<400> SEQUENCE: 25

```
gtttgtttaa acttggtacc ataactagtt cggcgcgcca ctagcgctgt cacgcgtctc      60
catggacagc tagcaatgat atcttcttaa ttaagaccta ggaaagcggc cgcggagctc     120
caggaattct gcagatcgac tgtgccttct agttgccagc catctgttgt ttgcccctcc     180
cccgtgcctt ccttgaccct ggaaggtgcc actcccactg tcctttccta ataaaatgag    240
gaaattgcat cgcattgtct gagtaggtgt cattctattc tggggggtgg ggtggggcag    300
gacagcaagg gggaggattg gaagacaat agcaggcatg ctgggatgc ggtgggctct      360 atggatcctc tagagtcgac ctgcaggcat gcaagcttgg cgtaatcatg gtcatagctg    420
tttcctgtgt gaaattgtta tccgctcaca attccacaca acatacgagc cggaagcata    480
aagtgtaaag cctggggtgc ctaatgagtg agctaactca cattaattgc gttgcgctca    540
ctgcccgctt tccagtcggg aaacctgtcg tgccagctgc attaatgaat cggccaacgc    600
```

```
gcggggagag gcggtttgcg tattgggcgc tcttccgctt cctcgctcac tgactcgctg    660
cgctcggtcg ttcggctgcg gcgagcggta tcagctcact caaaggcggt aatacggtta    720
tccacagaat caggggataa cgcaggaaag aacatgtgag caaaaggcca gcaaaaggcc    780
aggaaccgta aaaaggccgc gttgctggcg tttttccata ggctccgccc ccctgacgag    840
catcacaaaa atcgacgctc aagtcagagg tggcgaaacc cgacaggact ataaagatac    900
caggcgtttc cccctggaag ctccctcgtg cgctctcctg ttccgaccct gccgcttacc    960
ggatacctgt ccgcctttct cccttcggga agcgtggcgc tttctcatag ctcacgctgt   1020
aggtatctca gttcggtgta ggtcgttcgc tccaagctgg gctgtgtgca cgaaccccc    1080
gttcagcccg accgctgcgc cttatccggt aactatcgtc ttgagtccaa cccggtaaga   1140
cacgacttat cgccactggc agcagccact ggtaacagga ttagcagagc gaggtatgta   1200
ggcggtgcta cagagttctt gaagtggtgg cctaactacg gctacactag aaggacagta   1260
tttggtatct gcgctctgct gaagccagtt accttcggaa aaagagttgg tagctcttga   1320
tccggcaaac aaaccaccgc tggtagcggt ggtttttttg tttgcaagca gcagattacg   1380
cgcagaaaaa aaggatctca agaagatcct ttgatctttt ctacggggtc tgacgctcag   1440
tggaacgaaa actcacgtta agggattttg gtcatgagat tatcaaaaag gatcttcacc   1500
tagatccttt taaattaaaa atgaagtttt aaatcaatct aaagtatata tgagtaaact   1560
tggtctgaca gttaccaatg cttaatcagt gaggcaccta tctcagcgat ctgtctattt   1620
cgttcatcca tagttgcctg actccccgtc gtgtagataa ctacgatacg ggagggctta   1680
ccatctggcc ccagtgctgc aatgataccg cgagacccac gctcaccggc tccagattta   1740
tcagcaataa accagccagc cggaagggcc gagcgcagaa gtggtcctgc aactttatcc   1800
gcctccatcc agtctattaa ttgttgccgg gaagctagag taagtagttc gccagttaat   1860
agtttgcgca acgttgttgc cattgctaca ggcatcgtgg tgtcacgctc gtcgtttggt   1920
atggcttcat tcagctccgg ttcccaacga tcaaggcgag ttacatgatc ccccatgttg   1980
tgcaaaaaag cggttagctc cttcggtcct ccgatcgttg tcagaagtaa gttggccgca   2040
gtgttatcac tcatggttat ggcagcactg cataattctc ttactgtcat gccatccgta   2100
agatgctttt ctgtgactgg tgagtactca accaagtcat tctgagaata gtgtatgcgg   2160
cgaccgagtt gctcttgccc ggcgtcaata cgggataata ccgcgccaca tagcagaact   2220
ttaaaagtgc tcatcattgg aaaacgttct tcggggcgaa aactctcaag gatcttaccg   2280
ctgttgagat ccagttcgat gtaacccact cgtgcaccca actgatcttc agcatctttt   2340
actttcacca gcgtttctgg gtgagcaaaa acaggaaggc aaaatgccgc aaaaaaggga   2400
ataagggcga cacggaaatg ttgaatactc atactcttcc tttttcaata ttattgaagc   2460
atttatcagg gttattgtct catgagcgga tacatatttg aatgtattta gaaaaataaa   2520
caaatagggg ttccgcgcac atttccccga aaagtgccac ctgacgtcta agaaaccatt   2580
attatcatga cattaaccta taaaaatagg cgtatcacga ggccctttcg tctcgcgcgt   2640
ttcggtgatg acggtgaaaa cctctgacac atgcagctcc cggagacggt cacagcttgt   2700
ctgtaagcgg atgccgggag cagacaagcc cgtcagggcg cgtcagcggg tgttggcggg   2760
tgtcggggct ggcttaacta tgcggcatca gagcagattg tactgagagt gcaccatatg   2820
cggtgtgaaa taccgcacag atgcgtaagg agaaaatacc gcatcaggcg ccattcgcca   2880
ttcaggctgc gcaactgttg ggaagggcga tcggtgcggg cctcttcgct attacgccag   2940
ctggcgaaag ggggatgtgc tgcaaggcga ttaagttggg taacgccagg gttttcccag   3000
```

```
tcacgacgtt gtaaaacgac ggccagtgaa ttcgcgccaa agctaactgt aggactgagt    3060
ctattctaaa ctgaaagcct ggacatctgg agtaccaggg ggagatgacg tgttacgggc    3120
ttccataaaa gcagctggct tgaatggaa ggagccaaga ggccagcaca ggagcggatt     3180
cgtcgctttc acggccatcg agccgaacct ctcgcaagtc cgtgagccgt taaggaggcc    3240
cccagtcccg acccttcgcc ccaagcccct cggggtcccc gggcctggta ctccttgcca    3300
cacgggaggg gcgcggaagc cggggcggag gaggagccaa ccccgggctg gctgagacc     3360 cgcagaggaa gacgctctag ggatttgtcc cggactagcg agatggcaag gctgaggacg    3420
ggaggctgat tgagaggcga aggtacaccc taatctcaat acaacctttg gagctaagcc    3480
agcaatggta gagggaagat tctgcacgtc ccttccaggc ggcctccccg tcaccacccc    3540
ccccaacccg ccccgaccgg agctgagagt aattcataca aaaggactcg cccctgcctt    3600
ggggaatccc agggaccgtc gttaaactcc cactaacgta gaacccagag atcgctgcgt    3660
tcccgccccc tcaccogccc gctctcgtca tcactgaggt ggagaagagc atgcgtgagg    3720
ctccggtgcc cgtcagtggg cagagcgcac atcgcccaca gtccccgaga agttgggggg    3780
aggggtcggc aattgaaccg gtgcctagag aaggtggcgc ggggtaaact gggaaagtga    3840
tgtcgtgtac tggctccgcc ttttcccga gggtggggga gaaccgtata taagtgcagt    3900
agtcgccgtg aacgttcttt tcgcaacgg gtttgccgcc agaacacagg taagtgccgt     3960
gtgtggttcc cgcgggcctg cctctttac gggttatggc ccttgcgtgc cttgaattac     4020
ttccacgccc ctggctgcag tacgtgattc ttgatcccga gcttcgggtt ggaagtgggt    4080
gggagagttc gaggccttgc gcttaaggag ccccttcgcc tcgtgcttga gttgaggcct    4140
ggcttgggcg ctggggccgc cgcgtgcgaa tctggtggca ccttcgcgcc tgtctcgctg    4200
ctttcgataa gtctctagcc atttaaaatt tttgatgacc tgctgcgacg ctttttttct    4260
ggcaagatag tcttgtaaat gcgggccaag atcgatctgc acactggtat ttcggttttt    4320
ggggccgcgg gcggcgacgg ggcccgtgcg tcccagcgca catgttcggc gaggcggggc    4380
ctgcgagcgc ggccaccgag aatcggacgg gggtagtctc aagctggccg gcctgctctg    4440
gtgcctggcc tcgcgccgcc gtgtatcgcc ccgccctggg cggcaaggct ggcccggtcg    4500
gcaccagttg cgtgagcgga aagatggccg cttccggcc ctgctgcagg gagctcaaaa     4560
tggaggacgc ggcgctcggg agagcgggcg ggtgagtcac ccacacaaag gaaagggcc    4620 tttccgtcct cagccgtcgc ttcatgtgac tccacggagt accgggcgcc gtccaggcac    4680
ctcgattagt tctcgagctt ttggagtacg tcgtctttag gttgggggga ggggttttat    4740
gcgatggagt ttccccacac tgagtgggtg gagactgaag ttaggccagc ttggcacttg    4800
atgtaattct ccttggaatt tgccctttt gagtttggat cttggttcat tctcaagcct     4860
cagacagtgg ttcaaagttt ttttcttcca tttcaggtgt cgtgg                    4905
```

<210> SEQ ID NO 26
<211> LENGTH: 3201
<212> TYPE: DNA
<213> ORGANISM: artificial sequence
<220> FEATURE:
<223> OTHER INFORMATION: TALEN XPCT1L-HD

<400> SEQUENCE: 26

```
atgggcgatc ctaaaaagaa acgtaaggtc atcgattacc catacgatgt tccagattac      60
gctatcgata tcgccgaccc cattcgttcg cgcacaccaa gtcctgcccg cgagcttctg    120
```

```
cccggacccc aacccgatgg ggttcagccg actgcagatc gtggggtgtc tccgcctgcc       180
ggcggccccc tggatggctt gccggctcgg cggacgatgt cccggacccg gctgccatct       240 cccctgccc cctcacctgc gttctcggcg ggcagcttca gtgacctgtt acgtcagttc        300
gatccgtcac tttttaatac atcgcttttt gattcattgc ctcccttcgg cgctcaccat       360
acagaggctg ccacaggcga gtgggatgag gtgcaatcgg gtctgcgggc agccgacgcc       420
cccccaccca ccatgcgcgt ggctgtcact gccgcgcggc cccgcgcgc caagccggcg        480 ccgcgacgac gtgctgcgca accctccgac gcttcgccgg cggcgcaggt ggatctacgc       540
acgctcggct acagccagca gcaacaggag aagatcaaac cgaaggttcg ttcgacagtg       600
gcgcagcacc acgaggcact ggtcggccac gggtttacac acgcgcacat cgttgcgtta       660
agccaacacc cggcagcgtt agggaccgtc gctgtcaagt atcaggacat gatcgcagcg       720
ttgccagagg cgacacacga agcgatcgtt ggcgtcggca acagtggtc cggcgcacgc        780 gctctggagg ccttgctcac ggtggcggga gagttgagag gtccaccgtt acagttggac       840
acaggccaac ttctcaagat tgcaaaacgt ggcggcgtga ccgcagtgga ggcagtgcat       900
gcatggcgca atgcactgac gggtgccccg ctcaacttga ccccggagca ggtggtggcc       960
atcgccagcc acgatggcgg caagcaggcg ctggagacgg tccagcggct gttgccggtg       1020
ctgtgccagg cccacggctt gaccccggag caggtggtgg ccatcgccag ccacgatggc      1080
ggcaagcagg cgctggagac ggtccagcgg ctgttgccgg tgctgtgcca ggcccacggc       1140 ttgaccccc agcaggtggt ggccatcgcc agcaataatg gtggcaagca ggcgctggag        1200
acggtccagc ggctgttgcc ggtgctgtgc caggcccacg gcttgacccc ggagcaggtg       1260
gtggccatcg ccagcaatat tggtggcaag caggcgctgg agacggtgca ggcgctgttg      1320
ccggtgctgt gccaggccca cggcttgacc cccagcagg tggtggccat cgccagcaat       1380
aatggtggca agcaggcgct ggagacggtc agcggctgt tgccggtgct gtgccaggcc       1440
cacggcttga ccccggagca ggtggtggcc atcgccagca atattggtgg caagcaggcg       1500
ctggagacgg tgcaggcgct gttgccggtg ctgtgccagg cccacggctt gaccccccag      1560
caggtggtgg ccatcgccag caatggcggt ggcaagcagg cgctggagac ggtccagcgg      1620
ctgttgccgg tgctgtgcca ggcccacggc ttgaccccc agcaggtggt ggccatcgcc        1680
agcaataatg gtggcaagca ggcgctggag acggtccagc ggctgttgcc ggtgctgtgc       1740
caggcccacg gcttgacccc ccagcaggtg gtggccatcg ccagcaatgg cggtggcaag      1800
caggcgctgg agacggtcca gcggctgttg ccggtgctgt gccaggccca cggcttgacc      1860
ccggagcagg tggtggccat cgccagccac gatggcggca agcaggcgct ggagacggtc       1920
cagcggctgt tgccggtgct gtgccaggcc cacggcttga ccccgagca ggtggtggcc        1980 atcgccagca atattggtgg caagcaggcg ctggagacgg tgcaggcgct gttgccggtg       2040
ctgtgccagg cccacggctt gaccccggag caggtggtgg ccatcgccag ccacgatggc      2100
ggcaagcagg cgctggagac ggtccagcgg ctgttgccgg tgctgtgcca ggcccacggc       2160
ttgaccccgg agcaggtggt ggccatcgcc agcaatattg gtggcaagca ggcgctggag      2220
acggtgcagg cgctgttgcc ggtgctgtgc caggcccacg gcttgacccc ggagcaggtg       2280
gtggccatcg ccagccacga tggcggcaag caggcgctgg agacggtcca gcggctgttg      2340
ccggtgctgt gccaggccca cggcttgacc ccggagcagg tggtggccat cgccagcaat      2400
attggtggca agcaggcgct ggagacggtg caggcgctgt tgccggtgct gtgccaggcc       2460
cacggcttga ccccctcagca ggtggtggcc atcgccagca atggcggcgg caggccggcg     2520
```

```
ctggagagca ttgttgccca gttatctcgc cctgatccga gtggcagcgg aagtggcggg    2580
gatcctatca gccgttccca gctggtgaag tccgagctgg aggagaagaa atccgagttg    2640
aggcacaagc tgaagtacgt gccccacgag tacatcgagc tgatcgagat cgcccggaac    2700
agcacccagg accgtatcct ggagatgaag gtgatggagt tcttcatgaa ggtgtacggc    2760
tacaggggca agcacctggg cggctccagg aagcccgacg gcgccatcta caccgtgggc    2820
tcccccatcg actacggcgt gatcgtggac accaaggcct actccggcgg ctacaacctg    2880
cccatcggcc aggccgacga aatgcagagg tacgtggagg agaaccagac caggaacaag    2940
cacatcaacc ccaacgagtg gtggaaggtg taccctcca gcgtgaccga gttcaagttc    3000
ctgttcgtgt ccggccactt caagggcaac tacaaggccc agctgaccag gctgaaccac    3060
atcaccaact gcaacggcgc cgtgctgtcc gtggaggagc tcctgatcgg cggcgagatg    3120
atcaaggccg gcaccctgac cctggaggag gtgaggagga agttcaacaa cggcgagatc    3180
aacttcgcgg ccgactgata a                                              3201

<210> SEQ ID NO 27
<211> LENGTH: 3198
<212> TYPE: DNA
<213> ORGANISM: artificial sequence
<220> FEATURE:
<223> OTHER INFORMATION: TALEN XPCT1L-N*

<400> SEQUENCE: 27
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtggggtgtc tccgcctgcc     180
ggcggccccc tggatggctt gccggctcgg cggacgatgt cccggacccg gctgccatct     240
cccccctgcc cctcacctgc gttctcggcg ggcagcttca gtgacctgtt acgtcagttc     300
gatccgtcac tttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc cccgcgcgc caagccggcg     480 ccgcgacgac gtgctgcgca accctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
agccaacacc cggcagcgtt agggaccgtc gctgtcaagt atcaggacat gatcgcagcg     720
ttgccagagg cgacacacga agcgatcgtt ggcgtcggca acagtggtc cggcgcacgc     780 gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga ccccgagcca ggtggtggcc    960
atcgccagcc acgatggcgg caagcaggcg ctggagacgg tccagcggct gttgccggtg   1020
ctgtgccagg cccacggctt gaccccggag caggtggtgg ccatcgccag caatggcggc   1080
aagcaggcgc tggagacggt ccagcggctg ttgccggtgt gtgccaggc ccacggcttg    1140 acccccagc aggtggtggc catcgccagc aataatggtg gcaagcaggc gctggagacg   1200
gtccagcggc tgttgccggt gctgtgccag gcccacggct tgaccccgga gcaggtggtg    1260
gccatcgcca gcaatattgg tggcaagcag gcgctggaga cggtgcaggc gctgttgccg   1320
```

| | |
|---|---:|
| gtgctgtgcc aggcccacgg cttgacccc cagcaggtgg tggccatcgc cagcaataat | 1380 |
| ggtggcaagc aggcgctgga gacggtccag cggctgttgc cggtgctgtg ccaggcccac | 1440 |
| ggcttgaccc cggagcaggt ggtggccatc gccagcaata ttggtggcaa gcaggcgctg | 1500 |
| gagacggtgc aggcgctgtt gccggtgctg tgccaggccc acggcttgac ccccagcag | 1560 |
| gtggtggcca tcgccagcaa tggcggtggc aagcaggcgc tggagacggt ccagcggctg | 1620 |
| ttgccggtgc tgtgccaggc ccacggcttg acccccagc aggtggtggc catcgccagc | 1680 |
| aataatggtg caagcaggc gctggagacg tccagcggc tgttgccggt gctgtgccag | 1740 |
| gcccacggct tgaccccca gcaggtggtg gccatcgcca gcaatggcgg tggcaagcag | 1800 |
| gcgctggaga cggtccagcg gctgttgccg gtgctgtgcc aggcccacgg cttgaccccg | 1860 |
| gagcaggtgg tggccatcgc cagccacgat ggcggcaagc aggcgctgga gacggtccag | 1920 |
| cggctgttgc cggtgctgtg ccaggcccac ggcttgaccc cggagcaggt ggtggccatc | 1980 |
| gccagcaata ttggtggcaa gcaggcgctg gagacggtgc aggcgctgtt gccggtgctg | 2040 |
| tgccaggccc acggcttgac cccggagcag gtggtggcca tcgccagcca cgatggcggc | 2100 |
| aagcaggcgc tggagacggt ccagcggctg ttgccggtgc tgtgccaggc ccacggcttg | 2160 |
| accccgagc aggtggtggc catcgccagc aatattggtg gcaagcaggc gctggagacg | 2220 |
| gtgcaggcgc tgttgccggt gctgtgccag gcccacggct tgaccccgga gcaggtggtg | 2280 |
| gccatcgcca gccacgatgg cggcaagcag gcgctggaga cggtccagcg gctgttgccg | 2340 |
| gtgctgtgcc aggcccacgg cttgaccccg gagcaggtgg tggccatcgc cagcaatatt | 2400 |
| ggtggcaagc aggcgctgga gacggtcag gcgctgttgc cggtgctgtg ccaggcccac | 2460 |
| ggcttgaccc ctcagcaggt ggtggccatc gccagcaatg gcggcggcag gccggcgctg | 2520 |
| gagagcattg ttgcccagtt atctcgccct gatccgagtg gcagcggaag tggcggggat | 2580 |
| cctatcagcc gttcccagct ggtgaagtcc gagctggagg agaagaaatc cgagttgagg | 2640 |
| cacaagctga gtacgtgcc ccacgagtac atcgagctga tcgagatcgc ccggaacagc | 2700 |
| acccaggacc gtatcctgga gatgaaggtg atggagttct tcatgaaggt gtacggctac | 2760 |
| aggggcaagc acctgggcgg ctccaggaag cccgacggcg ccatctacac cgtgggctcc | 2820 |
| cccatcgact acggcgtgat cgtggacacc aaggcctact ccggcggcta caacctgccc | 2880 |
| atcggccagg ccgacgaaat gcagaggtac gtggaggaga accagaccag gaacaagcac | 2940 |
| atcaaccca acgagtggtg aaggtgtac ccctccagcg tgaccgagtt caagttcctg | 3000 |
| ttcgtgtccg gccacttcaa gggcaactac aaggcccagc tgaccaggct gaaccacatc | 3060 |
| accaactgca acggcgccgt gctgtccgtg gaggagctcc tgatcggcgg cgagatgatc | 3120 |
| aaggccggca ccctgaccct ggaggaggtg aggaggaagt caacaacgg cgagatcaac | 3180 |
| ttcgcggccg actgataa | 3198 |

<210> SEQ ID NO 28
<211> LENGTH: 3201
<212> TYPE: DNA
<213> ORGANISM: artificial sequence
<220> FEATURE:
<223> OTHER INFORMATION: TALEN XPCT1L-NG

<400> SEQUENCE: 28

| | |
|---|---:|
| atgggcgatc ctaaaaagaa acgtaaggtc atcgattacc catacgatgt tccagattac | 60 |
| gctatcgata tcgccgaccc cattcgttcg cgcacaccaa gtcctgcccg cgagcttctg | 120 |
| cccggacccc aacccgatgg ggttcagccg actgcagatc gtggggtgtc tccgcctgcc | 180 |

```
ggcggccccc tggatggctt gccggctcgg cggacgatgt cccggacccg gctgccatct    240
cccccctgcc cctcacctgc gttctcggcg ggcagcttca gtgacctgtt acgtcagttc    300
gatccgtcac tttttaatac atcgcttttt gattcattgc ctcccttcgg cgctcaccat    360
acagaggctg ccacaggcga gtgggatgag gtgcaatcgg gtctgcgggc agccgacgcc    420
cccccaccca ccatgcgcgt ggctgtcact gccgcgcggc cccgcgcgc aagccggcg     480 ccgcgacgac gtgctgcgca accctccgac gcttcgccgg cggcgcaggt ggatctacgc    540
acgctcggct acagccagca gcaacaggag aagatcaaac cgaaggttcg ttcgacagtg    600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca acagtggtc cggcgcacgc     780 gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacctga ccccagaaca ggtggtggct    960
atcgcctcac acgatggggg aaaacaggcc ctggagacag tgcagcggct gctccctgtg    1020
ctttgccagg ctcacggact gaccccccgag caggtggtcg caatcgccag taacggggc    1080 ggaaaacaag ccctggaaac agtccagcgc ctcctgcctg tgctgtgtca ggcccacggc    1140
ttgaccccac agcaggtcgt cgccattgct ccaacaatg gcggaaagca ggctctggag    1200
actgtgcaga gactgctccc cgtgctgtgc caggcacacg ggctgacacc tgagcaagtg    1260
gtcgccatcg caagcaacat tggcggcaag caagcccttg agacagtcca agctctgctg    1320
ccagtgcttt gtcaggctca tgggctcacc ccccagcaag tcgtggccat tgcctctaac    1380
aacggcggga agcaggcctt ggagaccgtc cagagactcc tgcccgtgct ctgccaagca    1440
catgggttga ctccagaaca ggtggtcgca attgccagta acatcggcgg aagcaagcg     1500 ttggaaactg tgcaagctct cctccccgtg ctgtgtcagg cacacggcct cacacctcaa    1560
caagtcgtgg caatcgcctc caacgggggg gggaagcagg ccctggagac agtccagagg    1620
ttgctgcccg tcctttgcca ggcccacggc ctgaccccac aacaagtggt ggctatcgca    1680
agtaacaatg gcgggaaaca agccctcgag acagtgcagc ggctcttgcc tgtcttgtgt    1740
caagcccacg gactgactcc ccaacaggtc gtggccatcg cctctaacgg cgggggcaag    1800
caagcactcg agactgtcca gcgcctcctg cccgtgcttt gccaagctca cggccttacc    1860
cctgagcaag tggtcgctat tgccagccat gatggcggaa agcaagccct ggaaaccgtg    1920
cagaggctgc tgccagtgct gtgccaggct catgggctga cacccgagca ggtggtggcc    1980
attgcctcaa atattggagg gaaacaggcc ttggagactg tgcaggcact cctcccagtg    2040
ctgtgtcagg ctcatggcct gactcccgag caagtcgtgg ccatcgcaag ccacgacggg    2100
gggaagcaag cactggagac cgtccagaga ctgctgcccg tgctctgtca agctcacgga    2160
ctgacaccag aacaggtggt cgccattgct ccaacattg gcggcaagca agccctggag     2220
acagtgcaag ctctcctgcc tgtgttgtgc caggctcacg gcctgacccc tgagcaggtc    2280
gtggcaatcg cctcccatga cggggggaaaa caggccctcg agaccgtgca gaggctgctt    2340
cctgtccttt gccaggccca cggcctcaca cccgaacagg tcgtcgctat tgccagcaat    2400 atcggggca agcaggctct cgagacagtc caggccttgc tcccagtgct gtgccaagcc    2460
cacgggctta ctccacagca ggtggtggct atcgccagca acgggggagg gcggccagct    2520
```

| | |
|---|---|
| ctggagagca ttgttgccca gttatctcgc cctgatccga gtggcagcgg aagtggcggg | 2580 |
| gatcctatca gccgttccca gctggtgaag tccgagctgg aggagaagaa atccgagttg | 2640 |
| aggcacaagc tgaagtacgt gccccacgag tacatcgagc tgatcgagat cgcccggaac | 2700 |
| agcacccagg accgtatcct ggagatgaag gtgatggagt tcttcatgaa ggtgtacggc | 2760 |
| tacaggggca agcacctggg cggctccagg aagcccgacg cgccatcta caccgtgggc | 2820 |
| tcccccatcg actacggcgt gatcgtggac accaaggcct actccggcgg ctacaacctg | 2880 |
| cccatcggcc aggccgacga aatgcagagg tacgtggagg agaaccagac caggaacaag | 2940 |
| cacatcaacc ccaacgagtg gtggaaggtg tacccctcca gcgtgaccga gttcaagttc | 3000 |
| ctgttcgtgt ccggccactt caagggcaac tacaaggccc agctgaccag gctgaaccac | 3060 |
| atcaccaact gcaacggcgc cgtgctgtcc gtggaggagc cctgatcgg cggcgagatg | 3120 |
| atcaaggccg gcaccctgac cctggaggag gtgaggagga agttcaacaa cggcgagatc | 3180 |
| aacttcgcgg ccgactgata a | 3201 |

<210> SEQ ID NO 29
<211> LENGTH: 3198
<212> TYPE: DNA
<213> ORGANISM: artificial sequence
<220> FEATURE:
<223> OTHER INFORMATION: TALEN XPCT1L-H*

<400> SEQUENCE: 29

| | |
|---|---|
| atgggcgatc ctaaaaagaa acgtaaggtc atcgattacc catacgatgt tccagattac | 60 |
| gctatcgata tcgccgaccc cattcgttcg cgcacaccaa gtcctgcccg cgagcttctg | 120 |
| cccggacccc aacccgatgg ggttcagccg actgcagatc gtggggtgtc tccgcctgcc | 180 |
| ggcggccccc tggatggctt gccggctcgg cggacgatgt cccggacccg gctgccatct | 240 |
| cccctgccc cctcacctgc gttctcggcg ggcagcttca gtgacctgtt acgtcagttc | 300 |
| gatccgtcac tttttaatac atcgcttttt gattcattgc ctcccttcgg cgctcaccat | 360 |
| acagaggctg ccacaggcga gtgggatgag gtgcaatcgg gtctgcgggc agccgacgcc | 420 |
| cccccaccca ccatgcgcgt ggctgtcact gccgcgcggc cccgcgcgc caagccggcg | 480 |
| ccgcgacgac gtgctgcgca accctccgac gcttcgccgg cggcgcaggt ggatctacgc | 540 |
| acgtcggct acagccagca gcaacaggag aagatcaaac cgaaggttcg ttcgacagtg | 600 |
| gcgcagcacc acgaggcact ggtcggccac gggtttacac acgcgcacat cgttgcgtta | 660 |
| agccaacacc cggcagcgtt agggaccgtc gctgtcaagt atcaggacat gatcgcagcg | 720 |
| ttgccagagg cgacacacga agcgatcgtt ggcgtcggca acagtggtc cggcgcacgc | 780 |
| gctctgagg ccttgctcac ggtggcggga gagttgagag gtccaccgtt acagttggac | 840 |
| acaggccaac ttctcaagat tgcaaaacgt ggcggcgtga ccgcagtgga ggcagtgcat | 900 |
| gcatggcgca atgcactgac gggtgccccg ctcaacctga ccccagaaca ggtggtggct | 960 |
| atcgcctcac acgatggggg aaaacaggcc ctggagacag tgcagcggct gctccctgtg | 1020 |
| ctttgccagg ctcacggact gacccccgag caggtggtcg caatcgccag tcacggggc | 1080 |
| aaacaagccc tggaaacagt ccagcgcctc ctgcctgtgc tgtgtcaggc ccacggcttg | 1140 |
| accccacagc aggtcgtcgc cattgcttcc aacaatggcg gaaagcaggc tctggagact | 1200 |
| gtgcagagac tgctccccgt gctgtgccag gcacacggg tgacacctga gcaagtggtc | 1260 |
| gccatcgcaa gcaacattgg cggcaagcaa gcccttgaga cagtccaagc tctgctgcca | 1320 |
| gtgctttgtc aggctcatgg gctcaccccc cagcaagtcg tggccattgc ctctaacaac | 1380 |

```
ggcgggaagc aggccttgga gaccgtccag agactcctgc ccgtgctctg ccaagcacat   1440
gggttgactc cagaacaggt ggtcgcaatt gccagtaaca tcggcgggaa gcaagcgttg   1500
gaaactgtgc aagctctcct ccccgtgctg tgtcaggcac acggcctcac acctcaacaa   1560
gtcgtggcaa tcgcctccaa cggggggggg aagcaggccc tggagacagt ccagaggttg   1620
ctgcccgtcc tttgccaggc ccacggcctg accccacaac aagtggtggc tatcgcaagt   1680
aacaatggcg ggaaacaagc cctcgagaca gtgcagcggc tcttgcctgt cttgtgtcaa   1740
gcccacggac tgactcccca acaggtcgtg gccatcgcct ctaacggcgg gggcaagcaa   1800
gcactcgaga ctgtccagcg cctcctgccc gtgctttgcc aagctcacgg ccttacccct   1860
gagcaagtgg tcgctattgc cagccatgat ggcggaaagc aagccctgga aaccgtgcag   1920
aggctgctgc cagtgctgtg ccaggctcat ggctgacac ccgagcaggt ggtggccatt    1980
gcctcaaata ttggagggaa acaggccttg gagactgtgc aggcactcct cccagtgctg   2040
tgtcaggctc atggcctgac tcccgagcaa gtcgtggcca tcgcaagcca cgacgggggg   2100
aagcaagcac tggagaccgt ccagagactg ctgcccgtgc tctgtcaagc tcacggactg   2160
acaccagaac aggtggtcgc cattgcttcc aacattggcg gcaagcaagc cctggagaca   2220
gtgcaagctc tcctgcctgt gttgtgccag gctcacggcc tgaccctga gcaggtcgtg    2280 gcaatcgcct cccatgacgg ggaaaacag gccctcgaga ccgtgcagag gctgcttcct    2340
gtcctttgcc aggcccacgg cctcacaccc gaacaggtcg tcgctattgc cagcaatatc   2400
gggggcaagc aggctctcga cagtccag gccttgctcc cagtgctgtg ccaagcccac     2460
gggcttactc cacagcaggt ggtggctatc gccagcaacg ggggagggcg ccagctctg    2520 gagagcattg ttgcccagtt atctcgccct gatccgagtg gcagcggaag tggcggggat   2580
cctatcagcc gttcccagct ggtgaagtcc gagctggagg agaagaaatc cgagttgagg   2640
cacaagctga agtacgtgcc ccacgagtac atcgagctga tcgagatcgc ccggaacagc   2700
acccaggacc gtatcctgga gatgaaggtg atggagttct tcatgaaggt gtacggctac   2760
aggggcaagc acctgggcgg ctccaggaag cccgacggcg ccatctacac cgtgggctcc   2820
cccatcgact acggcgtgat cgtggacacc aaggcctact ccggcggcta caacctgccc   2880
atcggccagg ccgacgaaat gcagaggtac gtggaggaga accagaccag gaacaagcac   2940 atcaaccccca acgagtggtg gaaggtgtac ccctccagcg tgaccgagtt caagttcctg   3000
ttcgtgtccg ccacttcaa gggcaactac aaggcccagc tgaccaggct gaaccacatc    3060
accaactgca acggcgccgt gctgtccgtg gaggagctcc tgatcggcgg cgagatgatc   3120
aaggccggca ccctgacccct ggaggaggtg aggaggaagt caacaacgg cgagatcaac   3180 ttcgcggccg actgataa                                                 3198
```

<210> SEQ ID NO 30
<211> LENGTH: 3219
<212> TYPE: DNA
<213> ORGANISM: artificial sequence
<220> FEATURE:
<223> OTHER INFORMATION: TALEN XPCT1R

<400> SEQUENCE: 30

```
atgggcgatc ctaaaaagaa acgtaaggtc atcgataagg agaccgccgc tgccaagttc     60
gagagacagc acatggacag catcgatatc gccgaccccca ttcgttcgcg cacaccaagt   120
cctgcccgcg agcttctgcc cggacccccaa cccgatgggg ttcagccgac tgcagatcgt   180
```

```
ggggtgtctc cgcctgccgg cggccccctg gatggcttgc cggctcggcg gacgatgtcc    240
cggacccggc tgccatctcc ccctgccccc tcacctgcgt tctcggcggg cagcttcagt    300
gacctgttac gtcagttcga tccgtcactt tttaatacat cgcttttga ttcattgcct     360
cccttcggcg ctcaccatac agaggctgcc acaggcgagt gggatgaggt gcaatcgggt    420
ctgcgggcag ccgacgcccc cccacccacc atgcgcgtgg ctgtcactgc cgcgcggccc    480
ccgcgcgcca agccggcgcc gcgacgacgt gctgcgcaac cctccgacgc ttcgccggcg    540
gcgcaggtgg atctacgcac gctcggctac agccagcagc aacaggagaa gatcaaaccg    600
aaggttcgtt cgacagtggc gcagcaccac gaggcactgg tcggccacgg gtttacacac    660
gcgcacatcg ttgcgttaag ccaacacccg gcagcgttag ggaccgtcgc tgtcaagtat    720
caggacatga tcgcagcgtt gccagaggcg acacacgaag cgatcgttgg cgtcggcaaa    780
cagtggtccg gcgcacgcgc tctggaggcc ttgctcacgg tggcgggaga gttgagaggt    840
ccaccgttac agttggacac aggccaactt ctcaagattg caaaacgtgg cggcgtgacc    900
gcagtggagg cagtgcatgc atggcgcaat gcactgacgg gtgccccgct caacttgacc    960
ccggagcagg tggtggccat cgccagccac gatggcggca agcaggcgct ggagacggtc   1020
cagcggctgt tgccggtgct gtgccaggcc cacggcttga ccccggagca ggtggtggcc   1080
atcgccagca atattggtgg caagcaggcg ctggagacgg tgcaggcgct gttgccggtg   1140
ctgtgccagg cccacggctt gaccccggag caggtggtgg ccatcgccag ccacgatggc   1200
ggcaagcagg cgctggagac ggtccagcgg ctgttgccgg tgctgtgcca ggcccacggc   1260
ttgaccccc agcaggtggt ggccatcgcc agcaatggcg gtggcaagca ggcgctggag    1320
acggtccagc ggctgttgcc ggtgctgtgc caggcccacg gcttgacccc ccagcaggtg   1380
gtggccatcg ccagcaataa tggtggcaag caggcgctgg agacggtcca gcggctgttg   1440
ccggtgctgt gccaggccca cggcttgacc cccagcagg tggtggccat cgccagcaat    1500
ggcggtggca agcaggcgct ggagacggtc cagcggctgt tgccggtgct gtgccaggcc   1560
cacggcttga ccccggagca ggtggtggcc atcgccagcc acgatggcgg caagcaggcg   1620
ctggagacgg tccagcggct gttgccggtg ctgtgccagg cccacggctt gaccccggag   1680
caggtggtgg ccatcgccag caatattggt ggcaagcagg cgctggagac ggtgcaggcg   1740
ctgttgccgg tgctgtgcca ggcccacggc ttgaccccc agcaggtggt ggccatcgcc    1800
agcaatggcg gtggcaagca ggcgctggag acggtccagc ggctgttgcc ggtgctgtgc   1860
caggcccacg gcttgacccc ggagcaggtg gtggccatcg ccagccacga tggcggcaag   1920
caggcgctgg agacggtcca gcggctgttg ccggtgctgt gccaggccca cggcttgacc   1980
ccggagcagg tggtggccat cgccagccac gatggcggca agcaggcgct ggagacggtc   2040
cagcggctgt tgccggtgct gtgccaggcc cacggcttga ccccggagca ggtggtggcc   2100
atcgccagca atattggtgg caagcaggcg ctggagacgg tgcaggcgct gttgccggtg   2160
ctgtgccagg cccacggctt gacccccag caggtggtgg ccatcgccag caataatggt    2220
ggcaagcagg cgctggagac ggtccagcgg ctgttgccgg tgctgtgcca ggcccacggc   2280
ttgaccccgg agcaggtggt ggccatcgcc agcaatattg gtggcaagca ggcgctggag   2340
acggtgcagg cgctgttgcc ggtgctgtgc caggcccacg gcttgacccc ggagcaggtg   2400
gtggccatcg ccagccacga tggcggcaag caggcgctgg agacggtcca gcggctgttg   2460
ccggtgctgt gccaggccca cggcttgacc cctcagcagg tggtggccat cgccagcaat   2520
ggcggcggca ggccggcgct ggagagcatt gttgcccagt tatctcgccc tgatccgagt   2580
```

```
ggcagcggaa gtggcgggga tcctatcagc cgttcccagc tggtgaagtc cgagctggag    2640
gagaagaaat ccgagttgag gcacaagctg aagtacgtgc cccacgagta catcgagctg    2700
atcgagatcg cccggaacag cacccaggac cgtatcctgg agatgaaggt gatggagttc    2760
ttcatgaagg tgtacggcta caggggcaag cacctgggcg gctccaggaa gcccgacggc    2820
gccatctaca ccgtgggctc ccccatcgac tacggcgtga tcgtggacac caaggcctac    2880
tccggcggct acaacctgcc catcggccag gccgacgaaa tgcagaggta cgtggaggag    2940
aaccagacca ggaacaagca catcaacccc aacgagtggt ggaaggtgta cccctccagc    3000
gtgaccgagt tcaagttcct gttcgtgtcc ggccacttca agggcaacta caaggcccag    3060
ctgaccaggc tgaaccacat caccaactgc aacggcgccg tgctgtccgt ggaggagctc    3120
ctgatcggcg gcgagatgat caaggccggc accctgaccc tggaggaggt gaggaggaag    3180
ttcaacaacg gcgagatcaa cttcgcggcc gactgataa    3219
```

<210> SEQ ID NO 31
<211> LENGTH: 3201
<212> TYPE: DNA
<213> ORGANISM: artificial sequence
<220> FEATURE:
<223> OTHER INFORMATION: TALEN XPCT2L-HD

<400> SEQUENCE: 31

```
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtggggtgtc tccgcctgcc     180
ggcggccccc tggatggctt gccggctcgg cggacgatgt cccggacccg gctgccatct     240 cccctgccc cctcacctgc gttctcggcg ggcagcttca gtgacctgtt acgtcagttc     300
gatccgtcac tttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc cccgcgcgc caagccggcg     480 ccgcgacgac gtgctgcgca accctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
agccaacacc cggcagcgtt agggaccgtc gctgtcaagt atcaggacat gatcgcagcg     720
ttgccagagg cgacacacga agcgatcgtt ggcgtcggca aacagtggtc cggcgcacgc     780
gctctggagg ccttgctcac ggtggcggga gagttgagag gtccaccgtt acagttggac     840
acaggccaac ttctcaagat tgcaaaacgt ggcggcgtga ccgcagtgga ggcagtgcat    900
gcatggcgca atgcactgac gggtgccccg ctcaacctga ccccacaaca ggtggtggct    960
atcgcctcaa ataacgggg aaaacaggcc ctggagacag tgcagcggct gctccctgtg   1020
ctttgccagg ctcacggact gaccccccag caggtggtcg caatcgccag taacaacggc   1080
ggaaaacaag ccctggaaac agtccagcgc ctcctgcctg tgctgtgtca ggcccacggc   1140 ttgacccac agcaggtcgt cgccattgct tccaacaatg gcggaaagca ggctctggag   1200
actgtgcaga gactgctccc cgtgctgtgc caggcacacg gctgacacc tcagcaagtg   1260 gtcgccatcg caagcaacgg gggcggcaag caagcccttg agacagtcca acggctgctg   1320
ccagtgcttt gtcaggctca tgggctcacc cccgagcaag tcgtggccat tgcctctcac   1380
```

| | |
|---|---|
| gatggcggga agcaggcctt ggagaccgtc cagagactcc tgcccgtgct ctgccaagca | 1440 |
| catgggttga ctccagaaca ggtggtcgca attgccagtc atgatggcgg gaagcaagcg | 1500 |
| ttggaaactg tgcaaagact cctccccgtg ctgtgtcagg cacacggcct cacacctcaa | 1560 |
| caagtcgtgg caatcgcctc caacaatggg gggaagcagg ccctggagac agtccagagg | 1620 |
| ttgctgcccg tcctttgcca ggcccacggc ctgacccag aacaagtggt ggctatcgca | 1680 |
| agtaacatcg gcgggaaaca agccctcgag acagtgcagg ctctcttgcc tgtcttgtgt | 1740 |
| caagcccacg gactgactcc ccaacaggtc gtggccatcg cctctaacaa cgggggcaag | 1800 |
| caagcactcg agactgtcca cgcctcctg cccgtgcttt gccaagctca cggccttacc | 1860 |
| cctgagcaag tggtcgctat tgccagcaac attggcggaa agcaagccct ggaaaccgtg | 1920 |
| caggcactgc tgccagtgct gtgccaggct catgggctga cacccagca ggtggtggcc | 1980 |
| attgcctcaa atggcggagg gaaacaggcc ttggagactg tgcagaggct cctcccagtg | 2040 |
| ctgtgtcagg ctcatggcct gactcccag caagtcgtgg ccatcgcaag caataacggg | 2100 |
| gggaagcaag cactggagac cgtccagaga ctgctgcccg tgctctgtca agctcacgga | 2160 |
| ctgacaccac aacaggtggt cgccattgct ccaacggcg gcggcaagca agccctggag | 2220 |
| acagtgcaaa gactcctgcc tgtgttgtgc caggctcacg gctgacccc tgagcaggtc | 2280 |
| gtggcaatcg cctcccatga cgggggaaaa caggccctcg agaccgtgca gaggctgctt | 2340 |
| cctgtccttt gccaggccca cggcctcaca cccgaacagg tcgtcgctat tgccagcaat | 2400 |
| atcggggca agcaggctct cgagacagtc caggccttgc tcccagtgct gtgccaagcc | 2460 |
| cacgggctta ctccacagca ggtggtggct atcgccagca acgggggagg gcggccagct | 2520 |
| ctggagagca ttgttgccca gttatctcgc cctgatccga gtggcagcgg aagtggcggg | 2580 |
| gatcctatca gccgttccca gctggtgaag tccgagctgg aggagaagaa atccgagttg | 2640 |
| aggcacaagc tgaagtacgt gccccacgag tacatcgagc tgatcgagat cgcccggaac | 2700 |
| agcacccagg accgtatcct ggagatgaag gtgatggagt tcttcatgaa ggtgtacggc | 2760 |
| tacaggggca agcacctggg cggctccagg aagcccgacg gcgccatcta caccgtgggc | 2820 |
| tcccccatcg actacggcgt gatcgtggac accaaggcct actccggcgg ctacaacctg | 2880 |
| cccatcggcc aggccgacga aatgcagagg tacgtggagg agaaccagac caggaacaag | 2940 |
| cacatcaacc ccaacgagtg gtggaaggtg taccctcca gcgtgaccga gttcaagttc | 3000 |
| ctgttcgtgt ccggccactt caagggcaac tacaaggccc agctgaccag gctgaaccac | 3060 |
| atcaccaact gcaacggcgc cgtgctgtcc gtggaggagc tcctgatcgg cggcgagatg | 3120 |
| atcaaggccg gcaccctgac cctggaggag gtgaggagga agttcaacaa cggcgagatc | 3180 |
| aacttcgcgg ccgactgata a | 3201 |

<210> SEQ ID NO 32
<211> LENGTH: 3198
<212> TYPE: DNA
<213> ORGANISM: artificial sequence
<220> FEATURE:
<223> OTHER INFORMATION: TALEN XPCT2L-N*

<400> SEQUENCE: 32

| | |
|---|---|
| atgggcgatc ctaaaaagaa acgtaaggtc atcgattacc catacgatgt tccagattac | 60 |
| gctatcgata tcgccgaccc cattcgttcg cgcacaccaa gtcctgcccg cgagcttctg | 120 |
| cccggacccc aacccgatgg ggttcagccg actgcagatc gtggggtgtc tccgcctgcc | 180 |
| ggcggccccc tggatggctt gccggctcgg cggacgatgt cccggacccg gctgccatct | 240 |

```
ccccctgccc cctcacctgc gttctcggcg ggcagcttca gtgacctgtt acgtcagttc    300
gatccgtcac ttttaatac atcgctttt gattcattgc ctcccttcgg cgctcaccat      360
acagaggctg ccacaggcga gtgggatgag gtgcaatcgg gtctgcgggc agccgacgcc    420
cccccaccca ccatgcgcgt ggctgtcact gccgcgcggc cccgcgcgc caagccggcg     480 ccgcgacgac gtgctgcgca accctccgac gcttcgccgg cggcgcaggt ggatctacgc    540
acgctcggct acagccagca gcaacaggag aagatcaaac cgaaggttcg ttcgacagtg    600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca acagtggtc cggcgcacgc     780 gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacctga ccccacaaca ggtggtggct    960
atcgcctcaa ataacggggg aaaacaggcc ctggagacag tgcagcggct gctccctgtg   1020
ctttgccagg ctcacggact gaccccccag caggtggtcg caatcgccag taacaacggc   1080
ggaaaacaag ccctggaaac agtccagcgc ctcctgcctg tgctgtgtca ggcccacggc   1140
ttgaccccac agcaggtcgt cgccattgct ccaacaatg gcggaaagca ggctctggag    1200
actgtgcaga gactgctccc cgtgctgtgc caggcacacg ggctgacacc tcagcaagtg   1260
gtcgccatcg caagcaacgg gggcggcaag caagcccttg agacagtcca acggctgctg   1320
ccagtgcttt gtcaggctca tgggctcacc cccgagcaag tcgtggccat tgcctctcac   1380
gatggcggga agcaggcctt ggagaccgtc cagagactcc tgcccgtgct ctgccaagca   1440
catgggttga ctccagaaca ggtggtcgca attgccagta atggcgggaa gcaagcgttg   1500
gaaactgtgc aaagactcct ccccgtgctg tgtcaggcac acggcctcac acctcaacaa   1560
gtcgtggcaa tcgcctccaa caatgggggg aagcaggccc tggagacagt ccagaggttg   1620
ctgcccgtcc tttgccaggc ccacggcctg accccagaac aagtggtggc tatcgcaagt   1680
aacatcggcg ggaaacaagc cctcgagaca gtgcaggctc tcttgcctgt cttgtgtcaa   1740
gcccacggac tgactcccca acaggtcgtg gccatcgcct ctaacaacgg gggcaagcaa   1800
gcactcgaga ctgtccagcg cctcctgccc gtgctttgcc aagctcacgg ccttacccct   1860
gagcaagtgg tcgctattgc cagcaacatt ggcggaaagc aagccctgga accgtgcag    1920 gcactgctgc cagtgctgtg ccaggctcat gggctgacac cccagcaggt ggtggccatt   1980
gcctcaaatg gcggagggaa acaggccttg gagactgtgc agaggctcct cccagtgctg   2040
tgtcaggctc atggcctgac tccccagcaa gtcgtggcca tcgcaagcaa taacgggggg   2100
aagcaagcac tggagaccgt ccagagactg ctgcccgtgc tctgtcaagc tcacggactg   2160
acaccacaac aggtggtcgc cattgcttcc aacggcggcg gcaagcaagc cctggagaca   2220
gtgcaaagac tcctgcctgt gttgtgccag gctcacggcc tgaccctga gcaggtcgtg    2280 gcaatcgcct cccatgacgg ggaaaacag gccctcgaga ccgtgcagag gctgcttcct    2340
gtcctttgcc aggcccacgg cctcacaccc gaacaggtcg tcgctattgc cagcaatatc   2400 ggggcaagc aggctctcga gacagtccag gccttgctcc cagtgctgtg ccaagcccac    2460
gggcttactc cacagcaggt ggtggctatc gccagcaacg ggggagggcg gccagctctg   2520
gagagcattg ttgcccagtt atctcgccct gatccgagtg gcagcggaag tggcggggat   2580
```

```
cctatcagcc gttcccagct ggtgaagtcc gagctggagg agaagaaatc cgagttgagg   2640
cacaagctga agtacgtgcc ccacgagtac atcgagctga tcgagatcgc ccggaacagc   2700
acccaggacc gtatcctgga gatgaaggtg atggagttct tcatgaaggt gtacggctac   2760
aggggcaagc acctgggcgg ctccaggaag cccgacggcg ccatctacac cgtgggctcc   2820
cccatcgact acggcgtgat cgtggacacc aaggcctact ccggcggcta caacctgccc   2880
atcggccagg ccgacgaaat gcagaggtac gtggaggaga accagaccag gaacaagcac   2940 atcaaccoca cgagtggtg gaaggtgtac ccctccagcg tgaccgagtt caagttcctg   3000
ttcgtgtccg gccacttcaa gggcaactac aaggcccagc tgaccaggct gaaccacatc   3060
accaactgca acggcgccgt gctgtccgtg gaggagctcc tgatcggcgg cgagatgatc   3120
aaggccggca ccctgaccct ggaggaggtg aggaggaagt caacaacgg cgagatcaac   3180 ttcgcggccg actgataa                                                 3198

<210> SEQ ID NO 33
<211> LENGTH: 3219
<212> TYPE: DNA
<213> ORGANISM: artificial sequence
<220> FEATURE:
<223> OTHER INFORMATION: TALEN XPCT2R

<400> SEQUENCE: 33
atgggcgatc taaaaagaa acgtaaggtc atcgataagg agaccgccgc tgccaagttc    60
gagagacagc acatggacag catcgatatc gccgacccca ttcgttcgcg cacaccaagt   120
cctgcccgcg agcttctgcc cggaccccaa cccgatgggg ttcagccgac tgcagatcgt   180
ggggtgtctc cgcctgccgg cggcccctg gatggcttgc cggctcggcg gacgatgtcc   240
cggacccggc tgccatctcc ccctgccccc tcacctgcgt tctcggcggg cagcttcagt   300
gacctgttac gtcagttcga tccgtcactt tttaatacat cgcttttga ttcattgcct   360 ccttcggcg ctcaccatac agaggctgcc acaggcgagt gggatgaggt gcaatcgggt   420
ctgcgggcag ccgacgcccc cccacccacc atgcgcgtgg ctgtcactgc cgcgcggccc   480
ccgcgcgcca gccggcgcc gcgacgacgt gctgcgcaac cctccgacgc ttcgccggcg   540
gcgcaggtgg atctacgcac gctcggctac agccagcagc aacaggagaa gatcaaaccg   600
aaggttcgtt cgacagtggc gcagcaccac gaggcactgg tcggccacgg gtttacacac   660
gcgcacatcg ttgcgttaag ccaacacccg gcagcgttag ggaccgtcgc tgtcaagtat   720
caggacatga tcgcagcgtt gccagaggcg acacacgaag cgatcgttgg cgtcggcaaa   780
cagtggtccg gcgcacgcgc tctggaggcc ttgctcacgg tggcgggaga gttgagaggt   840
ccaccgttac agttggacac aggccaactt ctcaagattg caaaacgtgg cggcgtgacc   900
gcagtggagg cagtgcatgc atggcgcaat gcactgacgg gtgccccgct caacctgacc   960
ccacaacagg tggtggctat cgcctcaaat aacggggaa acaggccct ggagacagtg   1020 cagcggctgc tccctgtgct tgccaggct cacggactga ccccccagca ggtggtcgca   1080
atcgccagta acggaggcgg aaaacaagcc ctggaaacag tccagcgcct cctgcctgtg   1140
ctgtgtcagg cccacggctt gaccccagag caggtcgtcg ccattgcttc ccacgatggc   1200
ggaaagcagg ctctggagac tgtgcagaga ctgctccccg tgctgtgcca ggcacacggg   1260
ctgacacctg agcaagtggt cgccatcgca agcaacattg gcggcaagca agcccttgag   1320
acagtccaag ctctgctgcc agtgctttgt caggctcatg gctcacccc caacaagtc    1380 gtggccattg cctctaacgg cggcgggaag caggccttgg agaccgtcca gagactcctg   1440
```

```
cccgtgctct gccaagcaca tgggttgact ccagaacagg tggtcgcaat tgccagtcat   1500
gatggcggga agcaagcgtt ggaaactgtg caaagactcc tccccgtgct gtgtcaggca   1560
cacggcctca cacctgaaca agtcgtggca atcgcctccc atgacggggg aagcaggcc   1620 ctggagacag tccagaggtt gctgcccgtc ctttgccagg ccacggcct gaccccagaa   1680 caagtggtgg ctatcgcaag taacatcggc gggaaacaag ccctcgagac agtgcaggct   1740
ctcttgcctg tcttgtgtca agcccacgga ctgactcccc aacaggtcgt ggccatcgcc   1800
tctaacaacg ggggcaagca agcactcgag actgtccagc gcctcctgcc cgtgctttgc   1860
caagctcacg gccttacccc tgagcaagtg gtcgctattg ccagcaacat ggcggaaag   1920 caagccctgg aaaccgtgca ggcactgctg ccagtgctgt gccaggctca tgggctgaca   1980
cccgagcagg tggtggccat tgcctcacat gatggaggga acaggccttg gagactgtg   2040 cagaggctcc tcccagtgct gtgtcaggct catggcctga ctccccagca agtcgtggcc   2100
atcgcaagca acggaggggg gaagcaagca ctggagaccg tccagagact gctgcccgtg   2160
ctctgtcaag ctcacggact gacaccacaa caggtggtcg ccattgcttc caacaacggc   2220
ggcaagcaag ccctggagac agtgcaaaga ctcctgcctg tgttgtgcca ggctcacggc   2280
ctgacccctc aacaggtcgt ggcaatcgcc tccaataatg ggggaaaaca ggccctcgag   2340
accgtgcaga ggctgcttcc tgtccttgc caggcccacg gcctcacacc ccagcaggtc   2400
gtcgctattg ccagcaataa cggggggcaag caggctctcg agacagtcca gaggttgctc   2460
ccagtgctgt gccaagccca cgggcttact ccacagcagg tggtggctat cgccagcaac   2520
gggggagggc ggccagctct ggagagcatt gttgcccagt tatctcgccc tgatccgagt   2580
ggcagcggaa gtggcgggga tcctatcagc cgttcccagc tggtgaagtc cgagctggag   2640
gagaagaaat ccgagttgag gcacaagctg aagtacgtgc cccacgagta catcgagctg   2700
atcgagatcg cccggaacag cacccaggac cgtatcctgg agatgaaggt gatggagttc   2760
ttcatgaagg tgtacggcta caggggcaag cacctgggcg gctccaggaa gcccgacggc   2820
gccatctaca ccgtgggctc ccccatcgac tacggcgtga tcgtggacac caaggcctac   2880
tccggcggct acaacctgcc catcggccag gccgacgaaa tgcagaggta cgtggaggag   2940
aaccagacca ggaacaagca tcaaccccc aacgagtggt ggaaggtgta cccctccagc   3000
gtgaccgagt tcaagttcct gttcgtgtcc ggcacttca agggcaacta caaggcccag   3060
ctgaccaggc tgaaccacat caccaactgc aacggcgccg tgctgtccgt ggaggagctc   3120
ctgatcggcg gcgagatgat caaggccggc accctgaccc tggaggaggt gaggaggaag   3180
ttcaacaacg gcgagatcaa cttcgcggcc gactgataa                          3219
```

<210> SEQ ID NO 34
<211> LENGTH: 3201
<212> TYPE: DNA
<213> ORGANISM: artificial sequence
<220> FEATURE:
<223> OTHER INFORMATION: TALEN XPCT3L-HD

<400> SEQUENCE: 34

```
atgggcgatc ctaaaaagaa acgtaaggtc atcgattacc catacgatgt tccagattac     60
gctatcgata tcgccgaccc cattcgttcg cgcacaccaa gtcctgcccg cgagcttctg   120 cccgacccc aacccgatgg ggttcagccg actgcagatc gtggggtgtc tccgcctgcc   180 ggcggcccc tggatggctt gccggctcgg cggacgatgt cccggaccccg gctgccatct   240
```

```
cccccctgccc cctcacctgc gttctcggcg ggcagcttca gtgacctgtt acgtcagttc      300
gatccgtcac ttttaatac atcgcttttt gattcattgc ctcccttcgg cgctcaccat        360
acagaggctg ccacaggcga gtgggatgag gtgcaatcgg gtctgcgggc agccgacgcc      420
cccccaccca ccatgcgcgt ggctgtcact gccgcgcggc cccgcgcgc caagccggcg       480 ccgcgacgac gtgctgcgca accctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca acagtggtc cggcgcacgc     780 gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacctga ccccacaaca ggtggtggct    960
atcgcctcaa ataacggggg aaaacaggcc ctggagacag tgcagcggct gctccctgtg   1020
ctttgccagg ctcacggact gacccccag caggtggtcg caatcgccag taacggaggc     1080
ggaaaacaag ccctggaaac agtccagcgc ctcctgcctg tgctgtgtca ggcccacggc   1140
ttgaccccag agcaggtcgt cgccattgct tcccacgatg gcggaaagca ggctctggag   1200
actgtgcaga gactgctccc cgtgctgtgc caggcacacg gctgacacc tgagcaagtg     1260 gtcgccatcg caagcaacat tggcggcaag caagcccttg agacagtcca agctctgctg   1320
ccagtgcttt gtcaggctca tgggctcacc cccgagcaag tcgtggccat tgcctctcat   1380
gatggcggga agcaggcctt ggagaccgtc cagagactcc tgcccgtgct ctgccaagca   1440
catgggttga ctccagaaca ggtggtcgca attgccagta atattggcgg gaagcaagcg    1500
ttggaaactg tgcaagctct cctccccgtg ctgtgtcagg cacacggcct cacacctgaa    1560
caagtcgtgg caatcgcctc ccatgacggg gggaagcagg ccctggagac agtccagagg    1620
ttgctgcccg tccttttgcca ggcccacggc ctgaccccag aacaagtggt ggctatcgca   1680
agtaacatcg gcgggaaaca agccctcgag acagtgcagg ctctcttgcc tgtcttgtgt   1740
caagcccacg gactgactcc ccaacaggtc gtggccatcg cctctaacaa cgggggcaag    1800
caagcactcg agactgtcca gcgcctcctg cccgtgcttt gccaagctca cggccttacc    1860
cctgagcaag tggtcgctat tgccagcaac attggcggaa agcaagccct ggaaaccgtg    1920
caggcactgc tgccagtgct gtgccaggct catgggctga caccccagca ggtggtggcc    1980
attgcctcaa ataacggagg gaaacaggcc ttggagactg tgcagaggct cctcccagtg    2040
ctgtgtcagg ctcatggcct gactccccag caagtcgtgg ccatcgcaag caacaatggg    2100
gggaagcaag cactggagac cgtccagaga ctgctgcccg tgctctgtca agctcacgga    2160
ctgacaccac aacaggtggt cgccattgct tccaacggcg gcggcaagca agccctggag    2220
acagtgcaaa gactcctgcc tgtgttgtgc caggctcacg gctgacccc tgagcaggtc      2280 gtggcaatcg cctccaatat cggggaaaa caggccctcg agaccgtgca ggccctgctt      2340
cctgtccttt gccaggccca cggcctcaca cccgaacagg tcgtcgctat tgccagccat    2400
gacgggggca agcaggctct cgagacagtc cagaggttgc tcccagtgct gtgccaagcc   2460
cacgggctta ctccacagca ggtggtggct atcgccagca acgggggagg gcggccagct    2520
ctggagagca ttgttgccca gttatctcgc cctgatccga gtggcagcgg aagtggcggg    2580
gatcctatca gccgttccca gctggtgaag tccgagctgg aggagaagaa atccgagttg    2640
```

-continued

```
aggcacaagc tgaagtacgt gccccacgag tacatcgagc tgatcgagat cgcccggaac    2700
agcacccagg accgtatcct ggagatgaag gtgatggagt tcttcatgaa ggtgtacggc    2760
tacaggggca agcacctggg cggctccagg aagcccgacg gcgccatcta caccgtgggc    2820
tcccccatcg actacggcgt gatcgtggac accaaggcct actccggcgg ctacaacctg    2880
cccatcggcc aggccgacga aatgcagagg tacgtggagg agaaccagac caggaacaag    2940
cacatcaacc ccaacgagtg gtggaaggtg taccccctcca gcgtgaccga gttcaagttc    3000
ctgttcgtgt ccggccactt caagggcaac tacaaggccc agctgaccag gctgaaccac    3060
atcaccaact gcaacggcgc cgtgctgtcc gtggaggagc tcctgatcgg cggcgagatg    3120
atcaaggccg gcaccctgac cctggaggag gtgaggagga agttcaacaa cggcgagatc    3180
aacttcgcgg ccgactgata a                                              3201
```

<210> SEQ ID NO 35
<211> LENGTH: 3198
<212> TYPE: DNA
<213> ORGANISM: artificial sequence
<220> FEATURE:
<223> OTHER INFORMATION: TALEN XPCT3L-N*

<400> SEQUENCE: 35

```
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtggggtgtc tccgcctgcc     180
ggcggccccc tggatggctt gccggctcgg cggacgatgt cccggacccg gctgccatct     240 cccccctgccc cctcacctgc gttctcggcg ggcagcttca gtgacctgtt acgtcagttc     300
gatccgtcac ttttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc ccccgcgcgc caagccggcg     480
ccgcgacgac gtgctgcgca acccctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
agccaacacc cggcagcgtt agggaccgtc gctgtcaagt atcaggacat gatcgcagcg     720
ttgccagagg cgacacacga agcgatcgtt ggcgtcggca aacagtggtc cggcgcacgc     780
gctctggagg ccttgctcac ggtggcggga gagttgagag gtccaccgtt acagttggac     840
acaggccaac ttctcaagat tgcaaaacgt ggcggcgtga ccgcagtgga ggcagtgcat     900
gcatggcgca atgcactgac gggtgccccg ctcaacctga cccacacaaca ggtggtggct     960 atcgcctcaa ataacggggg aaaacaggcc ctggagacag tgcagcggct gctccctgtg    1020
ctttgccagg ctcacggact gaccccccag caggtggtcg caatcgccag taacggaggc    1080
ggaaaacaag ccctggaaac agtccagcgc ctcctgcctg tgctgtgtca ggcccacggc    1140 ttgacccccag agcaggtcgt cgccattgct tcccacgatg gcggaaagca ggctctggag    1200
actgtgcaga gactgctccc cgtgctgtgc aggcacacg gctgacacc tgagcaagtg    1260 gtcgccatcg caagcaacat tggcggcaag caagcccttg agacagtcca agctctgctg    1320
ccagtgcttt gtcaggctca tgggctcacc cccgagcaag tcgtggccat tgcctctcat    1380
gatggcggga agcaggcctt ggagaccgtc cagagactcc tgcccgtgct ctgccaagca    1440
```

```
catgggttga ctccagaaca ggtggtcgca attgccagta atattggcgg gaagcaagcg      1500
ttggaaactg tgcaagctct cctccccgtg ctgtgtcagg cacacggcct cacacctgaa      1560
caagtcgtgg caatcgcctc ccatgacggg gggaagcagg ccctggagac agtccagagg      1620
ttgctgcccg tcctttgcca ggcccacggc ctgaccccag acaagtggt ggctatcgca       1680 agtaacatcg gcgggaaaca agccctcgag acagtgcagg ctctcttgcc tgtcttgtgt      1740
caagcccacg gactgactcc caacaggtc gtgggccatcg cctctaacaa cgggggcaag      1800
caagcactcg agactgtcca gcgcctcctg cccgtgcttt gccaagctca cggccttacc      1860
cctgagcaag tggtcgctat tgccagcaac attggcggaa agcaagccct ggaaaccgtg      1920
caggcactgc tgccagtgct gtgccaggct catgggctga caccccagca ggtggtggcc      1980
attgcctcaa ataacggagg gaaacaggcc ttggagactg tgcagaggct cctcccagtg      2040
ctgtgtcagg ctcatggcct gactccccag caagtcgtgg ccatcgcaag caacaatggg      2100
gggaagcaag cactggagac cgtccagaga ctgctgcccg tgctctgtca agctcacgga      2160
ctgacaccac aacaggtggt cgccattgct tccaacggcg gcggcaagca agccctggag      2220
acagtgcaaa gactcctgcc tgtgttgtgc caggctcacg gcctgacccc tgagcaggtc      2280
gtggcaatcg cctccaatat cggggggaaaa caggccctcg agaccgtgca ggccctgctt      2340 cctgtcctttt gccaggccca cggcctcaca cccgaacagg tcgtcgctat tgccagcaat      2400
gggggcaagc aggctctcga cagtccag aggttgctcc cagtgctgtg ccaagcccac       2460
gggcttactc cacagcaggt ggtggctatc gccagcaacg ggggagggcg gccagctctg      2520
gagagcattg ttgcccagtt atctcgccct gatccgagtg gcagcggaag tggcgggggat     2580 cctatcagcc gttccagct ggtgaagtcc gagctggagg agaagaaatc cgagttgagg       2640
cacaagctga gtacgtgcc ccacgagtac atcgagctga tcgagatcgc ccggaacagc       2700
acccaggacc gtatcctgga gatgaaggtg atggagttct tcatgaaggt gtacggctac      2760
aggggcaagc acctgggcgg ctccaggaag cccgacggcg ccatctacac cgtgggctcc      2820
cccatcgact acggcgtgat cgtggacacc aaggcctact ccggcggcta caacctgccc      2880
atcggccagg ccgacgaaat gcagaggtac gtggaggaga accagaccag gaacaagcac      2940
atcaacccca cgagtggtg aaggtgtac ccctccagcg tgaccgagtt caagttcctg        3000
ttcgtgtccg ccacttcaa ggcaactac aaggcccagc tgaccaggct gaaccacatc        3060
accaactgca acggcgccgt gctgtccgtg gaggagctcc tgatcggcgg cgagatgatc      3120
aaggccggca ccctgaccct ggaggaggtg aggaggaagt tcaacaacgg cgagatcaac      3180
ttcgcggccg actgataa                                                    3198
```

<210> SEQ ID NO 36
<211> LENGTH: 3219
<212> TYPE: DNA
<213> ORGANISM: artificial sequence
<220> FEATURE:
<223> OTHER INFORMATION: TALEN XPCT3R-HD

<400> SEQUENCE: 36

```
atgggcgatc ctaaaaagaa acgtaaggtc atcgataagg agaccgccgc tgccaagttc        60
gagagacagc acatggacag catcgatatc gccgacccca ttcgttcgcg cacaccaagt       120
cctgcccgcg agcttctgcc cggacccaa cccgatgggg ttcagccgac tgcagatcgt        180
ggggtgtctc cgcctgccgg cggccccctg gatggcttgc cggctcggcg gacgatgtcc       240
cggacccggc tgccatctcc ccctgccccc tcacctgcgt tctcggcggg cagcttcagt       300
```

```
gacctgttac gtcagttcga tccgtcactt tttaatacat cgcttttga ttcattgcct    360 cccttcggcg ctcaccatac agaggctgcc acaggcgagt gggatgaggt gcaatcgggt    420
ctgcgggcag ccgacgcccc cccacccacc atgcgcgtgg ctgtcactgc cgcgcggccc    480
ccgcgcgcca agccggcgcc gcgacgacgt gctgcgcaac cctccgacgc ttcgccggcg    540
gcgcaggtgg atctacgcac gctcggctac agccagcagc aacaggagaa gatcaaaccg    600
aaggttcgtt cgacagtggc gcagcaccac gaggcactgg tcggccacgg gtttacacac    660
gcgcacatcg ttgcgttaag ccaacacccg gcagcgttag ggaccgtcgc tgtcaagtat    720
caggacatga tcgcagcgtt gccagaggcg acacacgaag cgatcgttgg cgtcggcaaa    780
cagtggtccg gcgcacgcgc tctggaggcc ttgctcacgg tggcgggaga gttgagaggt    840
ccaccgttac agttggacac aggccaactt ctcaagattg caaaacgtgg cggcgtgacc    900
gcagtggagg cagtgcatgc atggcgcaat gcactgacgg gtgccccgct caacctgacc    960
ccacaacagg tggtggctat cgcctcaaat ggcgggggaa acaggccct ggagacagtg    1020 cagcggctgc tccctgtgct ttgccaggct cacggactga ccccccagca ggtggtcgca    1080
atcgccagta acaacggcgg aaaacaagcc ctggaaacag tccagcgcct cctgcctgtg    1140
ctgtgtcagg cccacggctt gaccccagag caggtcgtcg ccattgcttc ccacgatggc    1200
ggaaagcagg ctctggagac tgtgcagaga ctgctccccg tgctgtgcca ggcacacggg    1260
ctgacacctc agcaagtggt cgccatcgca agcaacaatg gcggcaagca agcccttgag    1320
acagtccaac ggctgctgcc agtgctttgt caggctcatg gctcaccccc caacaagtc    1380 gtggccattg cctctaataa cggcgggaag caggccttgg agaccgtcca gagactcctg    1440
cccgtgctct gccaagcaca tgggttgact ccacaacagg tggtcgcaat tgccagtaac    1500
aatggcggga agcaagcgtt ggaaactgtg caaagactcc tccccgtgct gtgtcaggca    1560
cacggcctca cacctcaaca agtcgtggca atcgcctcca acggggggg gaagcaggcc    1620 ctggagacag tccagaggtt gctgcccgtc ctttgccagg cccacggcct gaccccagaa    1680
caagtggtgg ctatcgcaag tcatgacggc gggaaacaag ccctcgagac agtgcagcgg    1740
ctcttgcctg tcttgtgtca agcccacgga ctgactcccg agcaggtcgt ggccatcgcc    1800
tctaacattg ggggcaagca agcactcgag actgtccagg ccctcctgcc cgtgctttgc    1860
caagctcacg gccttacccc tgagcaagtg gtcgctattg ccagccatga tggcggaaag    1920
caagccctgg aaaccgtgca gagactgctg ccagtgctgt gccaggctca tgggctgaca    1980
ccccagcagg tggtggccat tgcctcaaat ggcggaggga acaggccttg gagactgtg    2040 cagaggctcc tcccagtgct gtgtcaggct catggcctga ctccccagca agtcgtggcc    2100
atcgcaagca ataacggggg gaagcaagca ctggagaccg tccagagact gctgcccgtg    2160
ctctgtcaag ctcacggact gacaccacaa caggtggtcg ccattgcttc caacggcggc    2220
ggcaagcaag ccctggagac agtgcaaaga ctcctgcctg tgttgtgcca ggctcacggc    2280 ctgaccctg agcaggtcgt ggcaatcgcc tccatgacg ggggaaaaca ggccctcgag    2340
accgtgcaga ggctgcttcc tgtcctttgc caggcccacg gcctcacacc cgaacaggtc    2400
gtcgctattg ccagcaatat cggggcaag caggctctcg agacagtcca ggccttgctc    2460
ccagtgctgt gccaagccca cgggcttact ccacagcagg tggtggctat cgccagcaac    2520
gggggagggc ggccagctct ggagagcatt gttgcccagt atctcgccc tgatccgagt    2580 ggcagcggaa gtggcgggga tcctatcagc cgttcccagc tggtgaagtc cgagctggag    2640
```

| | |
|---|---:|
| gagaagaaat ccgagttgag gcacaagctg aagtacgtgc cccacgagta catcgagctg | 2700 |
| atcgagatcg cccggaacag cacccaggac cgtatcctgg agatgaaggt gatggagttc | 2760 |
| ttcatgaagg tgtacggcta caggggcaag cacctgggcg gctccaggaa gcccgacggc | 2820 |
| gccatctaca ccgtgggctc ccccatcgac tacggcgtga tcgtggacac caaggcctac | 2880 |
| tccggcggct acaacctgcc catcggccag gccgacgaaa tgcagaggta cgtggaggag | 2940 |
| aaccagacca ggaacaagca catcaacccc aacgagtggt ggaaggtgta ccctccagc | 3000 |
| gtgaccgagt tcaagttcct gttcgtgtcc ggccacttca agggcaacta caaggcccag | 3060 |
| ctgaccaggc tgaaccacat caccaactgc aacggcgccg tgctgtccgt ggaggagctc | 3120 |
| ctgatcggcg gcgagatgat caaggccggc accctgaccc tggaggaggt gaggaggaag | 3180 |
| ttcaacaacg gcgagatcaa cttcgcggcc gactgataa | 3219 |

<210> SEQ ID NO 37
<211> LENGTH: 3216
<212> TYPE: DNA
<213> ORGANISM: artificial sequence
<220> FEATURE:
<223> OTHER INFORMATION: TALEN XPCT3R-N*

<400> SEQUENCE: 37

| | |
|---|---:|
| atgggcgatc ctaaaaagaa acgtaaggtc atcgataagg agaccgccgc tgccaagttc | 60 |
| gagagacagc acatggacag catcgatatc gccgaccccca ttcgttcgcg cacaccaagt | 120 |
| cctgcccgcg agcttctgcc cggaccccaa cccgatgggg ttcagccgac tgcagatcgt | 180 |
| ggggtgtctc cgcctgccgg cggccccctg gatggcttgc cggctcggcg gacgatgtcc | 240 |
| cggacccggc tgccatctcc ccctgccccc tcacctgcgt tctcggcggg cagcttcagt | 300 |
| gacctgttac gtcagttcga tccgtcactt tttaatacat cgcttttttga ttcattgcct | 360 |
| cccttcggcg ctcaccatac agaggctgcc acaggcgagt gggatgaggt gcaatcgggt | 420 |
| ctgcgggcag ccgacgcccc cccacccacc atgcgcgtgg ctgtcactgc cgcgcggccc | 480 |
| ccgcgcgcca agccggcgcc gcgacgacgt gctgcgcaac cctccgacgc ttcgccggcg | 540 |
| gcgcaggtgg atctacgcac gctcggctac agccagcagc aacaggagaa gatcaaaccg | 600 |
| aaggttcgtt cgacagtggc gcagcaccac gaggcactgg tcggccacgg gtttacacac | 660 |
| gcgcacatcg ttgcgttaag ccaacacccg gcagcgttag ggaccgtcgc tgtcaagtat | 720 |
| caggacatga tcgcagcgtt gccagaggcg acacacgaag cgatcgttgg cgtcggcaaa | 780 |
| cagtggtccg gcgcacgcgc tctggaggcc ttgctcacgg tggcgggaga gttgagaggt | 840 |
| ccaccgttac agttggacac aggccaactt ctcaagattg caaaacgtgg cggcgtgacc | 900 |
| gcagtggagg cagtgcatgc atggcgcaat gcactgacgg gtgccccgct caacctgacc | 960 |
| ccacaacagg tggtggctat cgcctcaaat ggcggggaa acaggccct ggagacagtg | 1020 |
| cagcggctgc tccctgtgct tgccaggct cacggactga cccccagca ggtggtcgca | 1080 |
| atcgccagta acaacggcgg aaaacaagcc ctggaaacag tccagcgcct cctgcctgtg | 1140 |
| ctgtgtcagg cccacggctt gaccccagag caggtcgtcg ccattgcttc caatggcgga | 1200 |
| aagcaggctc tggagactgt gcagagactg ctccccgtgc tgtgccaggc acacgggctg | 1260 |
| acacctcagc aagtggtcgc catcgcaagc aacaatggcg gcaagcaagc ccttgagaca | 1320 |
| gtccaacggc tgctgccagt gctttgtcag gctcatgggc tcaccccca acaagtcgtg | 1380 |
| gccattgcct ctaataacgg cgggaagcag gccttggaga ccgtccagag actcctgccc | 1440 |
| gtgctctgcc aagcacatgg gttgactcca caacaggtgg tcgcaattgc cagtaacaat | 1500 |

```
ggcgggaagc aagcgttgga aactgtgcaa agactcctcc ccgtgctgtg tcaggcacac   1560
ggcctcacac ctcaacaagt cgtggcaatc gcctccaacg gggggggaa gcaggccctg    1620
gagacagtcc agaggttgct gcccgtcctt tgccaggccc acggcctgac cccagaacaa   1680
gtggtggcta tcgcaagtca tgacggcggg aaacaagccc tcgagacagt gcagcggctc   1740
ttgcctgtct tgtgtcaagc ccacggactg actcccgagc aggtcgtggc catcgcctct   1800
aacattgggg gcaagcaagc actcgagact gtccaggccc cctgcccgt gctttgccaa    1860
gctcacggcc ttacccctga gcaagtggtc gctattgcca gccatgatgg cggaaagcaa   1920
gccctggaaa ccgtgcagag actgctgcca gtgctgtgcc aggctcatgg gctgacaccc   1980
cagcaggtgg tggccattgc ctcaaatggc ggagggaaac aggccttgga gactgtgcag   2040
aggctcctcc cagtgctgtg tcaggctcat ggcctgactc cccagcaagt cgtggccatc   2100
gcaagcaata cgggggggaa gcaagcactg agaccgtcc agagactgct gcccgtgctc    2160
tgtcaagctc acggactgac accacaacag gtggtcgcca ttgcttccaa cggcggcggc   2220
aagcaagccc tggagacagt gcaaagactc ctgcctgtgt tgtgccaggc tcacggcctg   2280
accctgagc aggtcgtggc aatcgcctcc catgacgggg aaaacaggc cctcgagacc     2340
gtgcagaggc tgcttcctgt cctttgccag gcccacggcc tcacacccga caggtcgtc    2400
gctattgcca gcaatatcgg gggcaagcag gctctcgaga cagtccaggc cttgctccca   2460
gtgctgtgcc aagcccacgg gcttactcca gcaggtgg tggctatcgc cagcaacggg     2520
ggagggcggc cagctctgga gagcattgtt gcccagttat ctcgccctga tccgagtggc   2580
agcggaagtg gcggggatcc tatcagccgt tcccagctgg tgaagtccga gctggaggag   2640
aagaaatccg agttgaggca caagctgaag tacgtgcccc acgagtacat cgagctgatc   2700
gagatcgccc ggaacagcac ccaggaccgt atcctggaga tgaaggtgat ggagttcttc   2760
atgaaggtgt acggctacag gggcaagcac ctgggcggct ccaggaagcc cgacggcgcc   2820
atctacaccg tgggctcccc catcgactac ggcgtgatcg tggacaccaa ggcctactcc   2880
ggcggctaca acctgcccat cggccaggcc gacgaaatgc agaggtacgt ggaggagaac   2940
cagaccagga caagcacat caacccccaac gagtggtgga ggtgtacccc ctccagcgtg    3000
accgagttca gttcctgtt cgtgtccggc cacttcaagg caactacaa ggcccagctg      3060
accaggctga accacatcac caactgcaac ggcgccgtgc tgtccgtgga ggagctcctg   3120
atcggcggcg agatgatcaa ggccggcacc ctgacccgg aggaggtgag gaggaagttc    3180
aacaacggcg agatcaactt cgcggccgac tgataa                            3216
```

<210> SEQ ID NO 38
<211> LENGTH: 1065
<212> TYPE: PRT
<213> ORGANISM: artificial sequence
<220> FEATURE:
<223> OTHER INFORMATION: TALEN XPCT1L-HD

<400> SEQUENCE: 38

```
Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
```

```
            50                  55                  60
Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
                115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
                275                 280                 285

Lys Arg Gly Gly Val Thr Ala Val Glu Ala Val His Ala Trp Arg Asn
290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Ala His Gly Leu Thr Pro Gln
370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
                420                 425                 430

Leu Glu Thr Val Gln Ala Leu Leu Pro Val Leu Cys Gln Ala His Gly
                435                 440                 445

Leu Thr Pro Gln Gln Val Val Ala Ile Ala Ser Asn Asn Gly Gly Lys
                450                 455                 460

Gln Ala Leu Glu Thr Val Gln Arg Leu Leu Pro Val Leu Cys Gln Ala
465                 470                 475                 480
```

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Gln Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Asn Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Ile Gly Gly Lys Gln Ala Leu Glu
            660                 665                 670

Thr Val Gln Ala Leu Leu Pro Val Leu Cys Gln Ala His Gly Leu Thr
        675                 680                 685

Pro Glu Gln Val Val Ala Ile Ala Ser His Asp Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser Asn Ile Gly Gly Lys
                725                 730                 735

Gln Ala Leu Glu Thr Val Gln Ala Leu Leu Pro Val Leu Cys Gln Ala
            740                 745                 750

His Gly Leu Thr Pro Glu Gln Val Val Ala Ile Ala Ser His Asp Gly
        755                 760                 765

Gly Lys Gln Ala Leu Glu Thr Val Gln Arg Leu Leu Pro Val Leu Cys
    770                 775                 780

Gln Ala His Gly Leu Thr Pro Glu Gln Val Val Ala Ile Ala Ser Asn
785                 790                 795                 800

Ile Gly Gly Lys Gln Ala Leu Glu Thr Val Gln Ala Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Asp Pro Ile Ser
    850                 855                 860

Arg Ser Gln Leu Val Lys Ser Glu Leu Glu Glu Lys Ser Glu Leu
865                 870                 875                 880

Arg His Lys Leu Lys Tyr Val Pro His Glu Tyr Ile Glu Leu Ile Glu
                885                 890                 895

```
Ile Ala Arg Asn Ser Thr Gln Asp Arg Ile Leu Glu Met Lys Val Met
                900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
        980                 985                 990

Ser Ser Val Thr Glu Phe Lys Phe Leu Phe Val Ser Gly His Phe Lys
    995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
                1060                1065

<210> SEQ ID NO 39
<211> LENGTH: 1064
<212> TYPE: PRT
<213> ORGANISM: artificial sequence
<220> FEATURE:
<223> OTHER INFORMATION: TALEN XPCT1L-N*

<400> SEQUENCE: 39

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125

Asp Glu Val Gln Ser Gly Leu Arg Ala Ala Asp Ala Pro Pro Pro Thr
        130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190
```

-continued

```
Lys Pro Lys Val Arg Ser Thr Val Ala Gln His His Glu Ala Leu Val
            195                 200                 205
Gly His Gly Phe Thr His Ala His Ile Val Ala Leu Ser Gln His Pro
    210                 215                 220
Ala Ala Leu Gly Thr Val Ala Val Lys Tyr Gln Asp Met Ile Ala Ala
225                 230                 235                 240
Leu Pro Glu Ala Thr His Glu Ala Ile Val Gly Val Gly Lys Gln Trp
                245                 250                 255
Ser Gly Ala Arg Ala Leu Glu Ala Leu Leu Thr Val Ala Gly Glu Leu
            260                 265                 270
Arg Gly Pro Pro Leu Gln Leu Asp Thr Gly Gln Leu Leu Lys Ile Ala
        275                 280                 285
Lys Arg Gly Gly Val Thr Ala Val Glu Ala Val His Ala Trp Arg Asn
    290                 295                 300
Ala Leu Thr Gly Ala Pro Leu Asn Leu Thr Pro Glu Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Ala His Gly Leu Thr Pro Glu Gln Val
            340                 345                 350
Val Ala Ile Ala Ser Asn Gly Gly Lys Gln Ala Leu Glu Thr Val Gln
        355                 360                 365
Arg Leu Leu Pro Val Leu Cys Gln Ala His Gly Leu Thr Pro Gln Gln
    370                 375                 380
Val Val Ala Ile Ala Ser Asn Asn Gly Gly Lys Gln Ala Leu Glu Thr
385                 390                 395                 400
Val Gln Arg Leu Leu Pro Val Leu Cys Gln Ala His Gly Leu Thr Pro
                405                 410                 415
Glu Gln Val Val Ala Ile Ala Ser Asn Ile Gly Gly Lys Gln Ala Leu
            420                 425                 430
Glu Thr Val Gln Ala Leu Leu Pro Val Leu Cys Gln Ala His Gly Leu
        435                 440                 445
Thr Pro Gln Gln Val Val Ala Ile Ala Ser Asn Asn Gly Gly Lys Gln
    450                 455                 460
Ala Leu Glu Thr Val Gln Arg Leu Leu Pro Val Leu Cys Gln Ala His
465                 470                 475                 480
Gly Leu Thr Pro Glu Gln Val Val Ala Ile Ala Ser Asn Ile Gly Gly
                485                 490                 495
Lys Gln Ala Leu Glu Thr Val Gln Ala Leu Leu Pro Val Leu Cys Gln
            500                 505                 510
Ala His Gly Leu Thr Pro Gln Gln Val Val Ala Ile Ala Ser Asn Gly
        515                 520                 525
Gly Gly Lys Gln Ala Leu Glu Thr Val Gln Arg Leu Leu Pro Val Leu
    530                 535                 540
Cys Gln Ala His Gly Leu Thr Pro Gln Gln Val Val Ala Ile Ala Ser
545                 550                 555                 560
Asn Asn Gly Gly Lys Gln Ala Leu Glu Thr Val Gln Arg Leu Leu Pro
                565                 570                 575
Val Leu Cys Gln Ala His Gly Leu Thr Pro Gln Gln Val Val Ala Ile
            580                 585                 590
Ala Ser Asn Gly Gly Gly Lys Gln Ala Leu Glu Thr Val Gln Arg Leu
        595                 600                 605
Leu Pro Val Leu Cys Gln Ala His Gly Leu Thr Pro Glu Gln Val Val
```

-continued

```
            610                 615                 620
Ala Ile Ala Ser His Asp Gly Lys Gln Ala Leu Glu Thr Val Gln
625                 630                 635                 640

Arg Leu Leu Pro Val Leu Cys Gln Ala His Gly Leu Thr Pro Glu Gln
                    645                 650                 655

Val Val Ala Ile Ala Ser Asn Ile Gly Gly Lys Gln Ala Leu Glu Thr
                    660                 665                 670

Val Gln Ala Leu Leu Pro Val Leu Cys Gln Ala His Gly Leu Thr Pro
675                 680                 685

Glu Gln Val Val Ala Ile Ala Ser His Asp Gly Gly Lys Gln Ala Leu
690                 695                 700

Glu Thr Val Gln Arg Leu Leu Pro Val Leu Cys Gln Ala His Gly Leu
705                 710                 715                 720

Thr Pro Glu Gln Val Val Ala Ile Ala Ser Asn Ile Gly Gly Lys Gln
                    725                 730                 735

Ala Leu Glu Thr Val Gln Ala Leu Leu Pro Val Leu Cys Gln Ala His
                    740                 745                 750

Gly Leu Thr Pro Glu Gln Val Val Ala Ile Ala Ser His Asp Gly Gly
                    755                 760                 765

Lys Gln Ala Leu Glu Thr Val Gln Arg Leu Leu Pro Val Leu Cys Gln
770                 775                 780

Ala His Gly Leu Thr Pro Glu Gln Val Val Ala Ile Ala Ser Asn Ile
785                 790                 795                 800

Gly Gly Lys Gln Ala Leu Glu Thr Val Gln Ala Leu Leu Pro Val Leu
                    805                 810                 815

Cys Gln Ala His Gly Leu Thr Pro Gln Val Val Ala Ile Ala Ser
                    820                 825                 830

Asn Gly Gly Gly Arg Pro Ala Leu Glu Ser Ile Val Ala Gln Leu Ser
                    835                 840                 845

Arg Pro Asp Pro Ser Gly Ser Gly Gly Asp Pro Ile Ser Arg
850                 855                 860

Ser Gln Leu Val Lys Ser Glu Leu Glu Glu Lys Lys Ser Glu Leu Arg
865                 870                 875                 880

His Lys Leu Lys Tyr Val Pro His Glu Tyr Ile Glu Leu Ile Glu Ile
                    885                 890                 895

Ala Arg Asn Ser Thr Gln Asp Arg Ile Leu Glu Met Lys Val Met Glu
                    900                 905                 910

Phe Phe Met Lys Val Tyr Gly Tyr Arg Gly Lys His Leu Gly Gly Ser
                    915                 920                 925

Arg Lys Pro Asp Gly Ala Ile Tyr Thr Val Gly Ser Pro Ile Asp Tyr
930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr
                    965                 970                 975

Arg Asn Lys His Ile Asn Pro Asn Glu Trp Trp Lys Val Tyr Pro Ser
                    980                 985                 990

Ser Val Thr Glu Phe Lys Phe Leu Phe Val Ser Gly His Phe Lys Gly
                    995                 1000                1005

Asn Tyr Lys Ala Gln Leu Thr Arg Leu Asn His Ile Thr Asn Cys Asn
                    1010                1015                1020

Gly Ala Val Leu Ser Val Glu Glu Leu Leu Ile Gly Gly Glu Met Ile
1025                1030                1035                1040
```

```
Lys Ala Gly Thr Leu Thr Leu Glu Glu Val Arg Arg Lys Phe Asn Asn
                1045                1050                1055

Gly Glu Ile Asn Phe Ala Ala Asp
            1060

<210> SEQ ID NO 40
<211> LENGTH: 1065
<212> TYPE: PRT
<213> ORGANISM: artificial sequence
<220> FEATURE:
<223> OTHER INFORMATION: TALEN XPCT1L-NG

<400> SEQUENCE: 40

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335
```

```
Leu Leu Pro Val Leu Cys Gln Ala His Gly Leu Thr Pro Glu Gln Val
            340                 345                 350
Val Ala Ile Ala Ser Asn Gly Gly Lys Gln Ala Leu Glu Thr Val
        355                 360                 365
Gln Arg Leu Leu Pro Val Leu Cys Gln Ala His Gly Leu Thr Pro Gln
370                 375                 380
Gln Val Ala Ile Ala Ser Asn Asn Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Glu Gln Val Val Ala Ile Ala Ser Asn Ile Gly Gly Lys Gln Ala
                420                 425                 430
Leu Glu Thr Val Gln Ala Leu Leu Pro Val Leu Cys Gln Ala His Gly
            435                 440                 445
Leu Thr Pro Gln Gln Val Val Ala Ile Ala Ser Asn Asn Gly Gly Lys
        450                 455                 460
Gln Ala Leu Glu Thr Val Gln Arg Leu Leu Pro Val Leu Cys Gln Ala
465                 470                 475                 480
His Gly Leu Thr Pro Glu Gln Val Val Ala Ile Ala Ser Asn Ile Gly
                485                 490                 495
Gly Lys Gln Ala Leu Glu Thr Val Gln Ala Leu Leu Pro Val Leu Cys
            500                 505                 510
Gln Ala His Gly Leu Thr Pro Gln Gln Val Val Ala Ile Ala Ser Asn
            515                 520                 525
Gly Gly Gly Lys Gln Ala Leu Glu Thr Val Gln Arg Leu Leu Pro Val
        530                 535                 540
Leu Cys Gln Ala His Gly Leu Thr Pro Gln Gln Val Val Ala Ile Ala
545                 550                 555                 560
Ser Asn Asn Gly Gly Lys Gln Ala Leu Glu Thr Val Gln Arg Leu Leu
                565                 570                 575
Pro Val Leu Cys Gln Ala His Gly Leu Thr Pro Gln Gln Val Val Ala
            580                 585                 590
Ile Ala Ser Asn Gly Gly Gly Lys Gln Ala Leu Glu Thr Val Gln Arg
        595                 600                 605
Leu Leu Pro Val Leu Cys Gln Ala His Gly Leu Thr Pro Glu Gln Val
        610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Glu
                645                 650                 655
Gln Val Val Ala Ile Ala Ser Asn Ile Gly Gly Lys Gln Ala Leu Glu
                660                 665                 670
Thr Val Gln Ala Leu Leu Pro Val Leu Cys Gln Ala His Gly Leu Thr
            675                 680                 685
Pro Glu Gln Val Val Ala Ile Ala Ser His Asp Gly Gly Lys Gln Ala
        690                 695                 700
Leu Glu Thr Val Gln Arg Leu Leu Pro Val Leu Cys Gln Ala His Gly
705                 710                 715                 720
Leu Thr Pro Glu Gln Val Val Ala Ile Ala Ser Asn Ile Gly Gly Lys
                725                 730                 735
Gln Ala Leu Glu Thr Val Gln Ala Leu Leu Pro Val Leu Cys Gln Ala
            740                 745                 750
```

His Gly Leu Thr Pro Glu Gln Val Ala Ile Ala Ser His Asp Gly
          755                 760                 765

Gly Lys Gln Ala Leu Glu Thr Val Gln Arg Leu Leu Pro Val Leu Cys
770                 775                 780

Gln Ala His Gly Leu Thr Pro Glu Gln Val Val Ala Ile Ala Ser Asn
785                 790                 795                 800

Ile Gly Gly Lys Gln Ala Leu Glu Thr Val Gln Ala Leu Leu Pro Val
                805                 810                 815

Leu Cys Gln Ala His Gly Leu Thr Pro Gln Gln Val Val Ala Ile Ala
                820                 825                 830

Ser Asn Gly Gly Arg Pro Ala Leu Glu Ser Ile Val Ala Gln Leu
        835                 840                 845

Ser Arg Pro Asp Pro Ser Gly Ser Gly Ser Gly Asp Pro Ile Ser
850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
                900                 905                 910

Glu Phe Phe Met Lys Val Tyr Gly Tyr Arg Gly Lys His Leu Gly Gly
            915                 920                 925

Ser Arg Lys Pro Asp Gly Ala Ile Tyr Thr Val Gly Ser Pro Ile Asp
        930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 41
<211> LENGTH: 1064
<212> TYPE: PRT
<213> ORGANISM: artificial sequence
<220> FEATURE:
<223> OTHER INFORMATION: TALEN XPCT1L-H*

<400> SEQUENCE: 41

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

-continued

```
Gln Pro Thr Ala Asp Arg Gly Val Ser Pro Ala Gly Gly Pro Leu
     50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
             115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
            275                 280                 285

Lys Arg Gly Gly Val Thr Ala Val Glu Ala Val His Ala Trp Arg Asn
            290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Gly Gly Lys Gln Ala Leu Glu Thr Val Gln
            355                 360                 365

Arg Leu Leu Pro Val Leu Cys Gln Ala His Gly Leu Thr Pro Gln Gln
370                 375                 380

Val Val Ala Ile Ala Ser Asn Asn Gly Gly Lys Gln Ala Leu Glu Thr
385                 390                 395                 400

Val Gln Arg Leu Leu Pro Val Leu Cys Gln Ala His Gly Leu Thr Pro
                405                 410                 415

Glu Gln Val Val Ala Ile Ala Ser Asn Ile Gly Gly Lys Gln Ala Leu
                420                 425                 430

Glu Thr Val Gln Ala Leu Leu Pro Val Leu Cys Gln Ala His Gly Leu
            435                 440                 445

Thr Pro Gln Gln Val Val Ala Ile Ala Ser Asn Asn Gly Gly Lys Gln
450                 455                 460

Ala Leu Glu Thr Val Gln Arg Leu Leu Pro Val Leu Cys Gln Ala His
```

```
            465                 470                 475                 480
        Gly Leu Thr Pro Glu Gln Val Ala Ile Ala Ser Asn Ile Gly Gly
                        485                 490                 495
        Lys Gln Ala Leu Glu Thr Val Gln Ala Leu Leu Pro Val Leu Cys Gln
                    500                 505                 510
        Ala His Gly Leu Thr Pro Gln Gln Val Val Ala Ile Ala Ser Asn Gly
                        515                 520                 525
        Gly Gly Lys Gln Ala Leu Glu Thr Val Gln Arg Leu Leu Pro Val Leu
                    530                 535                 540
        Cys Gln Ala His Gly Leu Thr Pro Gln Gln Val Val Ala Ile Ala Ser
        545                 550                 555                 560
        Asn Asn Gly Gly Lys Gln Ala Leu Glu Thr Val Gln Arg Leu Leu Pro
                        565                 570                 575
        Val Leu Cys Gln Ala His Gly Leu Thr Pro Gln Gln Val Val Ala Ile
                    580                 585                 590
        Ala Ser Asn Gly Gly Gly Lys Gln Ala Leu Glu Thr Val Gln Arg Leu
                    595                 600                 605
        Leu Pro Val Leu Cys Gln Ala His Gly Leu Thr Pro Glu Gln Val Val
                    610                 615                 620
        Ala Ile Ala Ser His Asp Gly Gly Lys Gln Ala Leu Glu Thr Val Gln
        625                 630                 635                 640
        Arg Leu Leu Pro Val Leu Cys Gln Ala His Gly Leu Thr Pro Glu Gln
                        645                 650                 655
        Val Val Ala Ile Ala Ser Asn Ile Gly Gly Lys Gln Ala Leu Glu Thr
                        660                 665                 670
        Val Gln Ala Leu Leu Pro Val Leu Cys Gln Ala His Gly Leu Thr Pro
                    675                 680                 685
        Glu Gln Val Val Ala Ile Ala Ser His Asp Gly Gly Lys Gln Ala Leu
                    690                 695                 700
        Glu Thr Val Gln Arg Leu Leu Pro Val Leu Cys Gln Ala His Gly Leu
        705                 710                 715                 720
        Thr Pro Glu Gln Val Val Ala Ile Ala Ser Asn Ile Gly Gly Lys Gln
                        725                 730                 735
        Ala Leu Glu Thr Val Gln Ala Leu Leu Pro Val Leu Cys Gln Ala His
                    740                 745                 750
        Gly Leu Thr Pro Glu Gln Val Val Ala Ile Ala Ser His Asp Gly Gly
                    755                 760                 765
        Lys Gln Ala Leu Glu Thr Val Gln Arg Leu Leu Pro Val Leu Cys Gln
                    770                 775                 780
        Ala His Gly Leu Thr Pro Glu Gln Val Val Ala Ile Ala Ser Asn Ile
        785                 790                 795                 800
        Gly Gly Lys Gln Ala Leu Glu Thr Val Gln Ala Leu Leu Pro Val Leu
                        805                 810                 815
        Cys Gln Ala His Gly Leu Thr Pro Gln Gln Val Val Ala Ile Ala Ser
                    820                 825                 830
        Asn Gly Gly Gly Arg Pro Ala Leu Glu Ser Ile Val Ala Gln Leu Ser
                    835                 840                 845
        Arg Pro Asp Pro Ser Gly Ser Gly Ser Gly Asp Pro Ile Ser Arg
                    850                 855                 860
        Ser Gln Leu Val Lys Ser Glu Leu Glu Lys Lys Ser Glu Leu Arg
        865                 870                 875                 880
        His Lys Leu Lys Tyr Val Pro His Glu Tyr Ile Glu Leu Ile Glu Ile
                        885                 890                 895
```

```
Ala Arg Asn Ser Thr Gln Asp Arg Ile Leu Glu Met Lys Val Met Glu
            900                 905                 910

Phe Phe Met Lys Val Tyr Gly Tyr Arg Gly Lys His Leu Gly Gly Ser
            915                 920                 925

Arg Lys Pro Asp Gly Ala Ile Tyr Thr Val Gly Ser Pro Ile Asp Tyr
            930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr
            965                 970                 975

Arg Asn Lys His Ile Asn Pro Asn Glu Trp Trp Lys Val Tyr Pro Ser
            980                 985                 990

Ser Val Thr Glu Phe Lys Phe Leu Phe Val Ser Gly His Phe Lys Gly
            995                 1000                1005

Asn Tyr Lys Ala Gln Leu Thr Arg Leu Asn His Ile Thr Asn Cys Asn
            1010                1015                1020

Gly Ala Val Leu Ser Val Glu Glu Leu Leu Ile Gly Gly Glu Met Ile
1025                1030                1035                1040

Lys Ala Gly Thr Leu Thr Leu Glu Glu Val Arg Arg Lys Phe Asn Asn
            1045                1050                1055

Gly Glu Ile Asn Phe Ala Ala Asp
            1060

<210> SEQ ID NO 42
<211> LENGTH: 1071
<212> TYPE: PRT
<213> ORGANISM: artificial sequence
<220> FEATURE:
<223> OTHER INFORMATION: TALEN XPCT1R

<400> SEQUENCE: 42

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
                20                  25                  30

Pro Ile Arg Ser Arg Thr Pro Ser Pro Ala Arg Glu Leu Leu Pro Gly
            35                  40                  45

Pro Gln Pro Asp Gly Val Gln Pro Thr Ala Asp Arg Gly Val Ser Pro
        50                  55                  60

Pro Ala Gly Gly Pro Leu Asp Gly Leu Pro Ala Arg Arg Thr Met Ser
65                  70                  75                  80

Arg Thr Arg Leu Pro Ser Pro Ala Pro Ser Pro Ala Phe Ser Ala
                85                  90                  95

Gly Ser Phe Ser Asp Leu Leu Arg Gln Phe Asp Pro Ser Leu Phe Asn
                100                 105                 110

Thr Ser Leu Phe Asp Ser Leu Pro Pro Phe Gly Ala His His Thr Glu
            115                 120                 125

Ala Ala Thr Gly Glu Trp Asp Glu Val Gln Ser Gly Leu Arg Ala Ala
        130                 135                 140

Asp Ala Pro Pro Pro Thr Met Arg Val Ala Val Thr Ala Ala Arg Pro
145                 150                 155                 160

Pro Arg Ala Lys Pro Ala Pro Arg Arg Ala Ala Gln Pro Ser Asp
                165                 170                 175

Ala Ser Pro Ala Ala Gln Val Asp Leu Arg Thr Leu Gly Tyr Ser Gln
                180                 185                 190
```

```
Gln Gln Gln Glu Lys Ile Lys Pro Lys Val Arg Ser Thr Val Ala Gln
            195                 200                 205

His His Glu Ala Leu Val Gly His Gly Phe Thr Ala His Ile Val
210                 215                 220

Ala Leu Ser Gln His Pro Ala Leu Gly Thr Val Ala Val Lys Tyr
225                 230                 235                 240

Gln Asp Met Ile Ala Ala Leu Pro Glu Ala Thr His Glu Ala Ile Val
            245                 250                 255

Gly Val Gly Lys Gln Trp Ser Gly Ala Arg Ala Leu Glu Ala Leu Leu
            260                 265                 270

Thr Val Ala Gly Glu Leu Arg Gly Pro Pro Leu Gln Leu Asp Thr Gly
            275                 280                 285

Gln Leu Leu Lys Ile Ala Lys Arg Gly Gly Val Thr Ala Val Glu Ala
290                 295                 300

Val His Ala Trp Arg Asn Ala Leu Thr Gly Ala Pro Leu Asn Leu Thr
305                 310                 315                 320

Pro Glu Gln Val Val Ala Ile Ala Ser His Asp Gly Gly Lys Gln Ala
                325                 330                 335

Leu Glu Thr Val Gln Arg Leu Leu Pro Val Leu Cys Gln Ala His Gly
            340                 345                 350

Leu Thr Pro Glu Gln Val Val Ala Ile Ala Ser Asn Ile Gly Gly Lys
            355                 360                 365

Gln Ala Leu Glu Thr Val Gln Ala Leu Leu Pro Val Leu Cys Gln Ala
370                 375                 380

His Gly Leu Thr Pro Glu Gln Val Val Ala Ile Ala Ser His Asp Gly
385                 390                 395                 400

Gly Lys Gln Ala Leu Glu Thr Val Gln Arg Leu Leu Pro Val Leu Cys
                405                 410                 415

Gln Ala His Gly Leu Thr Pro Gln Gln Val Val Ala Ile Ala Ser Asn
            420                 425                 430

Gly Gly Gly Lys Gln Ala Leu Glu Thr Val Gln Arg Leu Leu Pro Val
            435                 440                 445

Leu Cys Gln Ala His Gly Leu Thr Pro Gln Gln Val Val Ala Ile Ala
450                 455                 460

Ser Asn Asn Gly Gly Lys Gln Ala Leu Glu Thr Val Gln Arg Leu Leu
465                 470                 475                 480

Pro Val Leu Cys Gln Ala His Gly Leu Thr Pro Gln Gln Val Val Ala
                485                 490                 495

Ile Ala Ser Asn Gly Gly Lys Gln Ala Leu Glu Thr Val Gln Arg
            500                 505                 510

Leu Leu Pro Val Leu Cys Gln Ala His Gly Leu Thr Pro Glu Gln Val
            515                 520                 525

Val Ala Ile Ala Ser His Asp Gly Gly Lys Gln Ala Leu Glu Thr Val
530                 535                 540

Gln Arg Leu Leu Pro Val Leu Cys Gln Ala His Gly Leu Thr Pro Glu
545                 550                 555                 560

Gln Val Val Ala Ile Ala Ser Asn Ile Gly Gly Lys Gln Ala Leu Glu
                565                 570                 575

Thr Val Gln Ala Leu Leu Pro Val Leu Cys Gln Ala His Gly Leu Thr
            580                 585                 590

Pro Gln Gln Val Val Ala Ile Ala Ser Asn Gly Gly Gly Lys Gln Ala
            595                 600                 605
```

```
Leu Glu Thr Val Gln Arg Leu Leu Pro Val Leu Cys Gln Ala His Gly
610                 615                 620

Leu Thr Pro Glu Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
            645                 650                 655

His Gly Leu Thr Pro Glu Gln Val Val Ala Ile Ala Ser His Asp Gly
            660                 665                 670

Gly Lys Gln Ala Leu Glu Thr Val Gln Arg Leu Leu Pro Val Leu Cys
        675                 680                 685

Gln Ala His Gly Leu Thr Pro Glu Gln Val Val Ala Ile Ala Ser Asn
690                 695                 700

Ile Gly Gly Lys Gln Ala Leu Glu Thr Val Gln Ala Leu Leu Pro Val
705                 710                 715                 720

Leu Cys Gln Ala His Gly Leu Thr Pro Gln Gln Val Val Ala Ile Ala
            725                 730                 735

Ser Asn Asn Gly Gly Lys Gln Ala Leu Glu Thr Val Gln Arg Leu Leu
            740                 745                 750

Pro Val Leu Cys Gln Ala His Gly Leu Thr Pro Glu Gln Val Val Ala
            755                 760                 765

Ile Ala Ser Asn Ile Gly Gly Lys Gln Ala Leu Glu Thr Val Gln Ala
770                 775                 780

Leu Leu Pro Val Leu Cys Gln Ala His Gly Leu Thr Pro Glu Gln Val
785                 790                 795                 800

Val Ala Ile Ala Ser His Asp Gly Gly Lys Gln Ala Leu Glu Thr Val
            805                 810                 815

Gln Arg Leu Leu Pro Val Leu Cys Gln Ala His Gly Leu Thr Pro Gln
            820                 825                 830

Gln Val Val Ala Ile Ala Ser Asn Gly Gly Arg Pro Ala Leu Glu
            835                 840                 845

Ser Ile Val Ala Gln Leu Ser Arg Pro Asp Pro Ser Gly Ser Gly Ser
850                 855                 860

Gly Gly Asp Pro Ile Ser Arg Ser Gln Leu Val Lys Ser Glu Leu Glu
865                 870                 875                 880

Glu Lys Lys Ser Glu Leu Arg His Lys Leu Lys Tyr Val Pro His Glu
            885                 890                 895

Tyr Ile Glu Leu Ile Glu Ile Ala Arg Asn Ser Thr Gln Asp Arg Ile
            900                 905                 910

Leu Glu Met Lys Val Met Glu Phe Phe Met Lys Val Tyr Gly Tyr Arg
            915                 920                 925

Gly Lys His Leu Gly Gly Ser Arg Lys Pro Asp Gly Ala Ile Tyr Thr
930                 935                 940

Val Gly Ser Pro Ile Asp Tyr Gly Val Ile Val Asp Thr Lys Ala Tyr
945                 950                 955                 960

Ser Gly Gly Tyr Asn Leu Pro Ile Gly Gln Ala Asp Glu Met Gln Arg
            965                 970                 975

Tyr Val Glu Glu Asn Gln Thr Arg Asn Lys His Ile Asn Pro Asn Glu
            980                 985                 990

Trp Trp Lys Val Tyr Pro Ser Ser Val Thr Glu Phe Lys Phe Leu Phe
            995                 1000                1005

Val Ser Gly His Phe Lys Gly Asn Tyr Lys Ala Gln Leu Thr Arg Leu
            1010                1015                1020

Asn His Ile Thr Asn Cys Asn Gly Ala Val Leu Ser Val Glu Glu Leu
```

```
            1025                1030                1035                1040
Leu Ile Gly Gly Glu Met Ile Lys Ala Gly Thr Leu Thr Leu Glu Glu
                    1045                1050                1055

Val Arg Arg Lys Phe Asn Asn Gly Glu Ile Asn Phe Ala Ala Asp
                    1060                1065                1070

<210> SEQ ID NO 43
<211> LENGTH: 1065
<212> TYPE: PRT
<213> ORGANISM: artificial sequence
<220> FEATURE:
<223> OTHER INFORMATION: TALEN XPCT2L-HD

<400> SEQUENCE: 43

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
```

```
                    325                 330                 335
Leu Leu Pro Val Leu Cys Gln Ala His Gly Leu Thr Pro Gln Gln Val
                340                 345                 350
Val Ala Ile Ala Ser Asn Asn Gly Gly Lys Gln Ala Leu Glu Thr Val
                355                 360                 365
Gln Arg Leu Leu Pro Val Leu Cys Gln Ala His Gly Leu Thr Pro Gln
            370                 375                 380
Gln Val Val Ala Ile Ala Ser Asn Asn Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Gln Gln Val Val Ala Ile Ala Ser Asn Gly Gly Gly Lys Gln Ala
            420                 425                 430
Leu Glu Thr Val Gln Arg Leu Leu Pro Val Leu Cys Gln Ala His Gly
                435                 440                 445
Leu Thr Pro Glu Gln Val Val Ala Ile Ala Ser His Asp Gly Gly Lys
            450                 455                 460
Gln Ala Leu Glu Thr Val Gln Arg Leu Leu Pro Val Leu Cys Gln Ala
465                 470                 475                 480
His Gly Leu Thr Pro Glu Gln Val Val Ala Ile Ala Ser His Asp Gly
                485                 490                 495
Gly Lys Gln Ala Leu Glu Thr Val Gln Arg Leu Leu Pro Val Leu Cys
            500                 505                 510
Gln Ala His Gly Leu Thr Pro Gln Gln Val Val Ala Ile Ala Ser Asn
            515                 520                 525
Asn Gly Gly Lys Gln Ala Leu Glu Thr Val Gln Arg Leu Leu Pro Val
        530                 535                 540
Leu Cys Gln Ala His Gly Leu Thr Pro Glu Gln Val Val Ala Ile Ala
545                 550                 555                 560
Ser Asn Ile Gly Gly Lys Gln Ala Leu Glu Thr Val Gln Ala Leu Leu
                565                 570                 575
Pro Val Leu Cys Gln Ala His Gly Leu Thr Pro Gln Gln Val Val Ala
            580                 585                 590
Ile Ala Ser Asn Asn Gly Gly Lys Gln Ala Leu Glu Thr Val Gln Arg
            595                 600                 605
Leu Leu Pro Val Leu Cys Gln Ala His Gly Leu Thr Pro Glu Gln Val
        610                 615                 620
Val Ala Ile Ala Ser Asn Ile Gly Gly Lys Gln Ala Leu Glu Thr Val
625                 630                 635                 640
Gln Ala Leu Leu Pro Val Leu Cys Gln Ala His Gly Leu Thr Pro Gln
                645                 650                 655
Gln Val Val Ala Ile Ala Ser Asn Gly Gly Gly Lys Gln Ala Leu Glu
            660                 665                 670
Thr Val Gln Arg Leu Leu Pro Val Leu Cys Gln Ala His Gly Leu Thr
            675                 680                 685
Pro Gln Gln Val Val Ala Ile Ala Ser Asn Asn Gly Gly Lys Gln Ala
        690                 695                 700
Leu Glu Thr Val Gln Arg Leu Leu Pro Val Leu Cys Gln Ala His Gly
705                 710                 715                 720
Leu Thr Pro Gln Gln Val Val Ala Ile Ala Ser Asn Gly Gly Gly Lys
                725                 730                 735
Gln Ala Leu Glu Thr Val Gln Arg Leu Leu Pro Val Leu Cys Gln Ala
            740                 745                 750
```

-continued

```
His Gly Leu Thr Pro Glu Gln Val Ala Ile Ala Ser His Asp Gly
        755                 760                 765
Gly Lys Gln Ala Leu Glu Thr Val Gln Arg Leu Leu Pro Val Leu Cys
770                 775                 780
Gln Ala His Gly Leu Thr Pro Glu Gln Val Val Ala Ile Ala Ser Asn
785                 790                 795                 800
Ile Gly Gly Lys Gln Ala Leu Glu Thr Val Gln Ala Leu Leu Pro Val
                805                 810                 815
Leu Cys Gln Ala His Gly Leu Thr Pro Gln Val Val Ala Ile Ala
                820                 825                 830
Ser Asn Gly Gly Gly Arg Pro Ala Leu Glu Ser Ile Val Ala Gln Leu
                835                 840                 845
Ser Arg Pro Asp Pro Ser Gly Ser Gly Ser Gly Gly Asp Pro Ile Ser
        850                 855                 860
Arg Ser Gln Leu Val Lys Ser Glu Leu Glu Glu Lys Ser Glu Leu
865                 870                 875                 880
Arg His Lys Leu Lys Tyr Val Pro His Glu Tyr Ile Glu Leu Ile Glu
                885                 890                 895
Ile Ala Arg Asn Ser Thr Gln Asp Arg Ile Leu Glu Met Lys Val Met
            900                 905                 910
Glu Phe Phe Met Lys Val Tyr Gly Tyr Arg Gly Lys His Leu Gly Gly
            915                 920                 925
Ser Arg Lys Pro Asp Gly Ala Ile Tyr Thr Val Gly Ser Pro Ile Asp
        930                 935                 940
Tyr Gly Val Ile Val Asp Thr Lys Ala Tyr Ser Gly Gly Tyr Asn Leu
945                 950                 955                 960
Pro Ile Gly Gln Ala Asp Glu Met Gln Arg Tyr Val Glu Glu Asn Gln
                965                 970                 975
Thr Arg Asn Lys His Ile Asn Pro Asn Glu Trp Trp Lys Val Tyr Pro
            980                 985                 990
Ser Ser Val Thr Glu Phe Lys Phe Leu Phe Val Ser Gly His Phe Lys
        995                 1000                1005
Gly Asn Tyr Lys Ala Gln Leu Thr Arg Leu Asn His Ile Thr Asn Cys
    1010                1015                1020
Asn Gly Ala Val Leu Ser Val Glu Glu Leu Leu Ile Gly Gly Glu Met
1025                1030                1035                1040
Ile Lys Ala Gly Thr Leu Thr Leu Glu Glu Val Arg Arg Lys Phe Asn
                1045                1050                1055
Asn Gly Glu Ile Asn Phe Ala Ala Asp
                1060                1065
```

<210> SEQ ID NO 44
<211> LENGTH: 1064
<212> TYPE: PRT
<213> ORGANISM: artificial sequence
<220> FEATURE:
<223> OTHER INFORMATION: TALEN XPCT2L-N*

<400> SEQUENCE: 44

```
Met Gly Asp Pro Lys Lys Lys Arg Lys Val Ile Asp Tyr Pro Tyr Asp
1               5                   10                  15
Val Pro Asp Tyr Ala Ile Asp Ile Ala Asp Pro Ile Arg Ser Arg Thr
                20                  25                  30
Pro Ser Pro Ala Arg Glu Leu Leu Pro Gly Pro Gln Pro Asp Gly Val
        35                  40                  45
```

```
Gln Pro Thr Ala Asp Arg Gly Val Ser Pro Ala Gly Gly Pro Leu
 50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Gly Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser His Asp Gly Gly Lys
    450                 455                 460
```

```
Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Lys Gln Ala Leu Glu Thr Val Gln Arg Leu Leu Pro Val Leu Cys Gln
            500                 505                 510

Ala His Gly Leu Thr Pro Gln Gln Val Val Ala Ile Ala Ser Asn Asn
        515                 520                 525

Gly Gly Lys Gln Ala Leu Glu Thr Val Gln Arg Leu Pro Val Leu
    530                 535                 540

Cys Gln Ala His Gly Leu Thr Pro Glu Gln Val Val Ala Ile Ala Ser
545                 550                 555                 560

Asn Ile Gly Gly Lys Gln Ala Leu Glu Thr Val Gln Ala Leu Leu Pro
                565                 570                 575

Val Leu Cys Gln Ala His Gly Leu Thr Pro Gln Gln Val Val Ala Ile
                580                 585                 590

Ala Ser Asn Asn Gly Gly Lys Gln Ala Leu Glu Thr Val Gln Arg Leu
            595                 600                 605

Leu Pro Val Leu Cys Gln Ala His Gly Leu Thr Pro Glu Gln Val Val
        610                 615                 620

Ala Ile Ala Ser Asn Ile Gly Gly Lys Gln Ala Leu Glu Thr Val Gln
625                 630                 635                 640

Ala Leu Leu Pro Val Leu Cys Gln Ala His Gly Leu Thr Pro Gln Gln
                645                 650                 655

Val Val Ala Ile Ala Ser Asn Gly Gly Gly Lys Gln Ala Leu Glu Thr
            660                 665                 670

Val Gln Arg Leu Leu Pro Val Leu Cys Gln Ala His Gly Leu Thr Pro
        675                 680                 685

Gln Gln Val Val Ala Ile Ala Ser Asn Asn Gly Gly Lys Gln Ala Leu
    690                 695                 700

Glu Thr Val Gln Arg Leu Leu Pro Val Leu Cys Gln Ala His Gly Leu
705                 710                 715                 720

Thr Pro Gln Gln Val Val Ala Ile Ala Ser Asn Gly Gly Gly Lys Gln
                725                 730                 735

Ala Leu Glu Thr Val Gln Arg Leu Leu Pro Val Leu Cys Gln Ala His
            740                 745                 750

Gly Leu Thr Pro Glu Gln Val Val Ala Ile Ala Ser His Asp Gly Gly
        755                 760                 765

Lys Gln Ala Leu Glu Thr Val Gln Arg Leu Leu Pro Val Leu Cys Gln
770                 775                 780

Ala His Gly Leu Thr Pro Glu Gln Val Val Ala Ile Ala Ser Asn Ile
785                 790                 795                 800

Gly Gly Lys Gln Ala Leu Glu Thr Val Gln Ala Leu Leu Pro Val Leu
                805                 810                 815

Cys Gln Ala His Gly Leu Thr Pro Gln Gln Val Val Ala Ile Ala Ser
            820                 825                 830

Asn Gly Gly Gly Arg Pro Ala Leu Glu Ser Ile Val Ala Gln Leu Ser
        835                 840                 845

Arg Pro Asp Pro Ser Gly Ser Gly Gly Asp Pro Ile Ser Arg
    850                 855                 860

Ser Gln Leu Val Lys Ser Glu Leu Glu Lys Lys Ser Glu Leu Arg
865                 870                 875                 880

His Lys Leu Lys Tyr Val Pro His Glu Tyr Ile Glu Leu Ile Glu Ile
```

-continued

```
                    885                 890                 895
Ala Arg Asn Ser Thr Gln Asp Arg Ile Leu Glu Met Lys Val Met Glu
                900                 905                 910

Phe Phe Met Lys Val Tyr Gly Tyr Arg Gly Lys His Leu Gly Gly Ser
            915                 920                 925

Arg Lys Pro Asp Gly Ala Ile Tyr Thr Val Gly Ser Pro Ile Asp Tyr
        930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr
                965                 970                 975

Arg Asn Lys His Ile Asn Pro Asn Glu Trp Trp Lys Val Tyr Pro Ser
            980                 985                 990

Ser Val Thr Glu Phe Lys Phe Leu Phe Val Ser Gly His Phe Lys Gly
        995                1000                1005

Asn Tyr Lys Ala Gln Leu Thr Arg Leu Asn His Ile Thr Asn Cys Asn
    1010                1015                1020

Gly Ala Val Leu Ser Val Glu Glu Leu Leu Ile Gly Gly Glu Met Ile
1025                1030                1035                1040

Lys Ala Gly Thr Leu Thr Leu Glu Glu Val Arg Arg Lys Phe Asn Asn
                1045                1050                1055

Gly Glu Ile Asn Phe Ala Ala Asp
            1060
```

<210> SEQ ID NO 45
<211> LENGTH: 1071
<212> TYPE: PRT
<213> ORGANISM: artificial sequence
<220> FEATURE:
<223> OTHER INFORMATION: TALEN XPCT2R

<400> SEQUENCE: 45

```
Met Gly Asp Pro Lys Lys Lys Arg Lys Val Ile Asp Lys Glu Thr Ala
1               5                  10                  15

Ala Ala Lys Phe Glu Arg Gln His Met Asp Ser Ile Asp Ile Ala Asp
            20                  25                  30

Pro Ile Arg Ser Arg Thr Pro Ser Pro Ala Arg Glu Leu Leu Pro Gly
        35                  40                  45

Pro Gln Pro Asp Gly Val Gln Pro Thr Ala Asp Arg Gly Val Ser Pro
    50                  55                  60

Pro Ala Gly Gly Pro Leu Asp Gly Leu Pro Ala Arg Arg Thr Met Ser
65                  70                  75                  80

Arg Thr Arg Leu Pro Ser Pro Ala Pro Ser Pro Ala Phe Ser Ala
                85                  90                  95

Gly Ser Phe Ser Asp Leu Leu Arg Gln Phe Asp Pro Ser Leu Phe Asn
            100                 105                 110

Thr Ser Leu Phe Asp Ser Leu Pro Pro Phe Gly Ala His His Thr Glu
        115                 120                 125

Ala Ala Thr Gly Glu Trp Asp Glu Val Gln Ser Gly Leu Arg Ala Ala
    130                 135                 140

Asp Ala Pro Pro Pro Thr Met Arg Val Ala Val Thr Ala Ala Arg Pro
145                 150                 155                 160

Pro Arg Ala Lys Pro Ala Pro Arg Arg Ala Ala Gln Pro Ser Asp
                165                 170                 175

Ala Ser Pro Ala Ala Gln Val Asp Leu Arg Thr Leu Gly Tyr Ser Gln
```

```
                180             185             190
Gln Gln Gln Glu Lys Ile Lys Pro Lys Val Arg Ser Thr Val Ala Gln
            195                 200                 205

His His Glu Ala Leu Val Gly His Gly Phe Thr His Ala His Ile Val
        210                 215                 220

Ala Leu Ser Gln His Pro Ala Ala Leu Gly Thr Val Ala Val Lys Tyr
225                 230                 235                 240

Gln Asp Met Ile Ala Ala Leu Pro Glu Ala Thr His Glu Ala Ile Val
                245                 250                 255

Gly Val Gly Lys Gln Trp Ser Gly Ala Arg Ala Leu Glu Ala Leu Leu
                260                 265                 270

Thr Val Ala Gly Glu Leu Arg Gly Pro Pro Leu Gln Leu Asp Thr Gly
            275                 280                 285

Gln Leu Leu Lys Ile Ala Lys Arg Gly Gly Val Thr Ala Val Glu Ala
        290                 295                 300

Val His Ala Trp Arg Asn Ala Leu Thr Gly Ala Pro Leu Asn Leu Thr
305                 310                 315                 320

Pro Gln Gln Val Val Ala Ile Ala Ser Asn Asn Gly Gly Lys Gln Ala
                325                 330                 335

Leu Glu Thr Val Gln Arg Leu Leu Pro Val Leu Cys Gln Ala His Gly
                340                 345                 350

Leu Thr Pro Gln Gln Val Val Ala Ile Ala Ser Asn Gly Gly Gly Lys
            355                 360                 365

Gln Ala Leu Glu Thr Val Gln Arg Leu Leu Pro Val Leu Cys Gln Ala
        370                 375                 380

His Gly Leu Thr Pro Glu Gln Val Val Ala Ile Ala Ser His Asp Gly
385                 390                 395                 400

Gly Lys Gln Ala Leu Glu Thr Val Gln Arg Leu Leu Pro Val Leu Cys
                405                 410                 415

Gln Ala His Gly Leu Thr Pro Glu Gln Val Val Ala Ile Ala Ser Asn
                420                 425                 430

Ile Gly Gly Lys Gln Ala Leu Glu Thr Val Gln Ala Leu Leu Pro Val
            435                 440                 445

Leu Cys Gln Ala His Gly Leu Thr Pro Gln Gln Val Val Ala Ile Ala
        450                 455                 460

Ser Asn Gly Gly Gly Lys Gln Ala Leu Glu Thr Val Gln Arg Leu Leu
465                 470                 475                 480

Pro Val Leu Cys Gln Ala His Gly Leu Thr Pro Glu Gln Val Val Ala
                485                 490                 495

Ile Ala Ser His Asp Gly Gly Lys Gln Ala Leu Glu Thr Val Gln Arg
                500                 505                 510

Leu Leu Pro Val Leu Cys Gln Ala His Gly Leu Thr Pro Glu Gln Val
            515                 520                 525

Val Ala Ile Ala Ser His Asp Gly Gly Lys Gln Ala Leu Glu Thr Val
            530                 535                 540

Gln Arg Leu Leu Pro Val Leu Cys Gln Ala His Gly Leu Thr Pro Glu
545                 550                 555                 560

Gln Val Val Ala Ile Ala Ser Asn Ile Gly Gly Lys Gln Ala Leu Glu
                565                 570                 575

Thr Val Gln Ala Leu Leu Pro Val Leu Cys Gln Ala His Gly Leu Thr
                580                 585                 590

Pro Gln Gln Val Val Ala Ile Ala Ser Asn Asn Gly Gly Lys Gln Ala
            595                 600                 605
```

```
Leu Glu Thr Val Gln Arg Leu Leu Pro Val Leu Cys Gln Ala His Gly
    610                 615                 620

Leu Thr Pro Glu Gln Val Val Ala Ile Ala Ser Asn Ile Gly Gly Lys
625                 630                 635                 640

Gln Ala Leu Glu Thr Val Gln Ala Leu Leu Pro Val Leu Cys Gln Ala
                    645                 650                 655

His Gly Leu Thr Pro Glu Gln Val Val Ala Ile Ala Ser His Asp Gly
                660                 665                 670

Gly Lys Gln Ala Leu Glu Thr Val Gln Arg Leu Leu Pro Val Leu Cys
        675                 680                 685

Gln Ala His Gly Leu Thr Pro Gln Gln Val Val Ala Ile Ala Ser Asn
690                 695                 700

Gly Gly Gly Lys Gln Ala Leu Glu Thr Val Gln Arg Leu Leu Pro Val
705                 710                 715                 720

Leu Cys Gln Ala His Gly Leu Thr Pro Gln Gln Val Val Ala Ile Ala
                725                 730                 735

Ser Asn Asn Gly Gly Lys Gln Ala Leu Glu Thr Val Gln Arg Leu Leu
                740                 745                 750

Pro Val Leu Cys Gln Ala His Gly Leu Thr Pro Gln Gln Val Val Ala
            755                 760                 765

Ile Ala Ser Asn Asn Gly Gly Lys Gln Ala Leu Glu Thr Val Gln Arg
770                 775                 780

Leu Leu Pro Val Leu Cys Gln Ala His Gly Leu Thr Pro Gln Gln Val
785                 790                 795                 800

Val Ala Ile Ala Ser Asn Asn Gly Gly Lys Gln Ala Leu Glu Thr Val
                805                 810                 815

Gln Arg Leu Leu Pro Val Leu Cys Gln Ala His Gly Leu Thr Pro Gln
                820                 825                 830

Gln Val Val Ala Ile Ala Ser Asn Gly Gly Gly Arg Pro Ala Leu Glu
            835                 840                 845

Ser Ile Val Ala Gln Leu Ser Arg Pro Asp Pro Ser Gly Ser Gly Ser
850                 855                 860

Gly Gly Asp Pro Ile Ser Arg Ser Gln Leu Val Lys Ser Glu Leu Glu
865                 870                 875                 880

Glu Lys Lys Ser Glu Leu Arg His Lys Leu Lys Tyr Val Pro His Glu
                885                 890                 895

Tyr Ile Glu Leu Ile Glu Ile Ala Arg Asn Ser Thr Gln Asp Arg Ile
                900                 905                 910

Leu Glu Met Lys Val Met Glu Phe Phe Met Lys Val Tyr Gly Tyr Arg
            915                 920                 925

Gly Lys His Leu Gly Gly Ser Arg Lys Pro Asp Gly Ala Ile Tyr Thr
930                 935                 940

Val Gly Ser Pro Ile Asp Tyr Gly Val Ile Val Asp Thr Lys Ala Tyr
945                 950                 955                 960

Ser Gly Gly Tyr Asn Leu Pro Ile Gly Gln Ala Asp Glu Met Gln Arg
                965                 970                 975

Tyr Val Glu Glu Asn Gln Thr Arg Asn Lys His Ile Asn Pro Asn Glu
            980                 985                 990

Trp Trp Lys Val Tyr Pro Ser Ser Val Thr Glu Phe Lys Phe Leu Phe
            995                 1000                1005

Val Ser Gly His Phe Lys Gly Asn Tyr Lys Ala Gln Leu Thr Arg Leu
    1010                1015                1020
```

-continued

Asn His Ile Thr Asn Cys Asn Gly Ala Val Leu Ser Val Glu Glu Leu
1025                1030                1035                1040

Leu Ile Gly Gly Glu Met Ile Lys Ala Gly Thr Leu Thr Leu Glu Glu
            1045                1050                1055

Val Arg Arg Lys Phe Asn Asn Gly Glu Ile Asn Phe Ala Ala Asp
            1060                1065                1070

<210> SEQ ID NO 46
<211> LENGTH: 1065
<212> TYPE: PRT
<213> ORGANISM: artificial sequence
<220> FEATURE:
<223> OTHER INFORMATION: TALEN XPCT3L-HD

<400> SEQUENCE: 46

Met Gly Asp Pro Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
305                 310                 315                 320

-continued

```
Ile Ala Ser Asn Asn Gly Gly Lys Gln Ala Leu Glu Thr Val Gln Arg
            325                 330                 335

Leu Leu Pro Val Leu Cys Gln Ala His Gly Leu Thr Pro Gln Gln Val
        340                 345                 350

Val Ala Ile Ala Ser Asn Gly Gly Lys Gln Ala Leu Glu Thr Val
    355                 360                 365

Gln Arg Leu Leu Pro Val Leu Cys Gln Ala His Gly Leu Thr Pro Glu
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
            420                 425                 430

Leu Glu Thr Val Gln Ala Leu Leu Pro Val Leu Cys Gln Ala His Gly
        435                 440                 445

Leu Thr Pro Glu Gln Val Val Ala Ile Ala Ser His Asp Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Glu Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Ala Leu Leu
                565                 570                 575

Pro Val Leu Cys Gln Ala His Gly Leu Thr Pro Gln Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Ile Gly Gly Lys Gln Ala Leu Glu Thr Val
625                 630                 635                 640

Gln Ala Leu Leu Pro Val Leu Cys Gln Ala His Gly Leu Thr Pro Gln
                645                 650                 655

Gln Val Val Ala Ile Ala Ser Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Gln Gln Val Val Ala Ile Ala Ser Asn Asn Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Gln Gln Val Val Ala Ile Ala Ser Asn Gly Gly Gly Lys
                725                 730                 735

Gln Ala Leu Glu Thr Val Gln Arg Leu Leu Pro Val Leu Cys Gln Ala
```

```
                740                 745                 750
His Gly Leu Thr Pro Glu Gln Val Val Ala Ile Ala Ser Asn Ile Gly
            755                 760                 765

Gly Lys Gln Ala Leu Glu Thr Val Gln Ala Leu Leu Pro Val Leu Cys
        770                 775                 780

Gln Ala His Gly Leu Thr Pro Glu Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Gly Asp Pro Ile Ser
            850                 855                 860

Arg Ser Gln Leu Val Lys Ser Glu Leu Glu Glu Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 47
<211> LENGTH: 1064
<212> TYPE: PRT
<213> ORGANISM: artificial sequence
<220> FEATURE:
<223> OTHER INFORMATION: TALEN XPCT3L-N*

<400> SEQUENCE: 47

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
```

```
                35                  40                  45
Gln Pro Thr Ala Asp Arg Gly Val Ser Pro Ala Gly Gly Pro Leu
 50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
                115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
                210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
                275                 280                 285

Lys Arg Gly Gly Val Thr Ala Val Glu Ala Val His Ala Trp Arg Asn
290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
                340                 345                 350

Val Ala Ile Ala Ser Asn Gly Gly Gly Lys Gln Ala Leu Glu Thr Val
                355                 360                 365

Gln Arg Leu Leu Pro Val Leu Cys Gln Ala His Gly Leu Thr Pro Glu
                370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
                420                 425                 430

Leu Glu Thr Val Gln Ala Leu Leu Pro Val Leu Cys Gln Ala His Gly
                435                 440                 445

Leu Thr Pro Glu Gln Val Val Ala Ile Ala Ser His Asp Gly Gly Lys
450                 455                 460
```

-continued

```
Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Glu Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Ala Leu Leu
                565                 570                 575

Pro Val Leu Cys Gln Ala His Gly Leu Thr Pro Gln Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Ile Gly Gly Lys Gln Ala Leu Glu Thr Val
625                 630                 635                 640

Gln Ala Leu Leu Pro Val Leu Cys Gln Ala His Gly Leu Thr Pro Gln
                645                 650                 655

Gln Val Val Ala Ile Ala Ser Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Gln Gln Val Val Ala Ile Ala Ser Asn Asn Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Gln Gln Val Val Ala Ile Ala Ser Asn Gly Gly Gly Lys
                725                 730                 735

Gln Ala Leu Glu Thr Val Gln Arg Leu Leu Pro Val Leu Cys Gln Ala
            740                 745                 750

His Gly Leu Thr Pro Glu Gln Val Val Ala Ile Ala Ser Asn Ile Gly
        755                 760                 765

Gly Lys Gln Ala Leu Glu Thr Val Gln Ala Leu Leu Pro Val Leu Cys
    770                 775                 780

Gln Ala His Gly Leu Thr Pro Glu Gln Val Val Ala Ile Ala Ser Asn
785                 790                 795                 800

Gly Gly Lys Gln Ala Leu Glu Thr Val Gln Arg Leu Leu Pro Val Leu
                805                 810                 815

Cys Gln Ala His Gly Leu Thr Pro Gln Gln Val Val Ala Ile Ala Ser
            820                 825                 830

Asn Gly Gly Arg Pro Ala Leu Glu Ser Ile Val Ala Gln Leu Ser
        835                 840                 845

Arg Pro Asp Pro Ser Gly Ser Gly Gly Asp Pro Ile Ser Arg
    850                 855                 860

Ser Gln Leu Val Lys Ser Glu Leu Glu Glu Lys Lys Ser Glu Leu Arg
865                 870                 875                 880
```

His Lys Leu Lys Tyr Val Pro His Glu Tyr Ile Glu Leu Ile Glu Ile
                885                 890                 895

Ala Arg Asn Ser Thr Gln Asp Arg Ile Leu Glu Met Lys Val Met Glu
            900                 905                 910

Phe Phe Met Lys Val Tyr Gly Tyr Arg Gly Lys His Leu Gly Gly Ser
        915                 920                 925

Arg Lys Pro Asp Gly Ala Ile Tyr Thr Val Gly Ser Pro Ile Asp Tyr
    930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr
                965                 970                 975

Arg Asn Lys His Ile Asn Pro Asn Glu Trp Trp Lys Val Tyr Pro Ser
            980                 985                 990

Ser Val Thr Glu Phe Lys Phe Leu Phe Val Ser Gly His Phe Lys Gly
        995                 1000                1005

Asn Tyr Lys Ala Gln Leu Thr Arg Leu Asn His Ile Thr Asn Cys Asn
    1010                1015                1020

Gly Ala Val Leu Ser Val Glu Glu Leu Leu Ile Gly Gly Glu Met Ile
1025                1030                1035                1040

Lys Ala Gly Thr Leu Thr Leu Glu Glu Val Arg Arg Lys Phe Asn Asn
                1045                1050                1055

Gly Glu Ile Asn Phe Ala Ala Asp
            1060

<210> SEQ ID NO 48
<211> LENGTH: 1071
<212> TYPE: PRT
<213> ORGANISM: artificial sequence
<220> FEATURE:
<223> OTHER INFORMATION: TALEN XPCT3R-HD

<400> SEQUENCE: 48

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
                20                  25                  30

Pro Ile Arg Ser Arg Thr Pro Ser Pro Ala Arg Glu Leu Leu Pro Gly
            35                  40                  45

Pro Gln Pro Asp Gly Val Gln Pro Thr Ala Asp Arg Gly Val Ser Pro
        50                  55                  60

Pro Ala Gly Gly Pro Leu Asp Gly Leu Pro Ala Arg Arg Thr Met Ser
65                  70                  75                  80

Arg Thr Arg Leu Pro Ser Pro Pro Ala Pro Ser Pro Ala Phe Ser Ala
                85                  90                  95

Gly Ser Phe Ser Asp Leu Leu Arg Gln Phe Asp Pro Ser Leu Phe Asn
            100                 105                 110

Thr Ser Leu Phe Asp Ser Leu Pro Pro Phe Gly Ala His His Thr Glu
        115                 120                 125

Ala Ala Thr Gly Glu Trp Asp Glu Val Gln Ser Gly Leu Arg Ala Ala
    130                 135                 140

Asp Ala Pro Pro Pro Thr Met Arg Val Ala Val Thr Ala Ala Arg Pro
145                 150                 155                 160

Pro Arg Ala Lys Pro Ala Pro Arg Arg Ala Ala Gln Pro Ser Asp
                165                 170                 175

```
Ala Ser Pro Ala Ala Gln Val Asp Leu Arg Thr Leu Gly Tyr Ser Gln
            180                 185                 190

Gln Gln Gln Glu Lys Ile Lys Pro Lys Val Arg Ser Thr Val Ala Gln
        195                 200                 205

His His Glu Ala Leu Val Gly His Gly Phe Thr His Ala His Ile Val
    210                 215                 220

Ala Leu Ser Gln His Pro Ala Ala Leu Gly Thr Val Ala Val Lys Tyr
225                 230                 235                 240

Gln Asp Met Ile Ala Ala Leu Pro Glu Ala Thr His Glu Ala Ile Val
                245                 250                 255

Gly Val Gly Lys Gln Trp Ser Gly Ala Arg Ala Leu Glu Ala Leu Leu
            260                 265                 270

Thr Val Ala Gly Glu Leu Arg Gly Pro Pro Leu Gln Leu Asp Thr Gly
        275                 280                 285

Gln Leu Leu Lys Ile Ala Lys Arg Gly Gly Val Thr Ala Val Glu Ala
    290                 295                 300

Val His Ala Trp Arg Asn Ala Leu Thr Gly Ala Pro Leu Asn Leu Thr
305                 310                 315                 320

Pro Gln Gln Val Val Ala Ile Ala Ser Asn Gly Gly Lys Gln Ala
                325                 330                 335

Leu Glu Thr Val Gln Arg Leu Leu Pro Val Leu Cys Gln Ala His Gly
            340                 345                 350

Leu Thr Pro Gln Gln Val Val Ala Ile Ala Ser Asn Gly Gly Lys
        355                 360                 365

Gln Ala Leu Glu Thr Val Gln Arg Leu Leu Pro Val Leu Cys Gln Ala
370                 375                 380

His Gly Leu Thr Pro Glu Gln Val Val Ala Ile Ala Ser His Asp Gly
385                 390                 395                 400

Gly Lys Gln Ala Leu Glu Thr Val Gln Arg Leu Leu Pro Val Leu Cys
                405                 410                 415

Gln Ala His Gly Leu Thr Pro Gln Gln Val Val Ala Ile Ala Ser Asn
            420                 425                 430

Asn Gly Gly Lys Gln Ala Leu Glu Thr Val Gln Arg Leu Leu Pro Val
        435                 440                 445

Leu Cys Gln Ala His Gly Leu Thr Pro Gln Gln Val Val Ala Ile Ala
    450                 455                 460

Ser Asn Asn Gly Gly Lys Gln Ala Leu Glu Thr Val Gln Arg Leu Leu
465                 470                 475                 480

Pro Val Leu Cys Gln Ala His Gly Leu Thr Pro Gln Gln Val Val Ala
                485                 490                 495

Ile Ala Ser Asn Asn Gly Gly Lys Gln Ala Leu Glu Thr Val Gln Arg
            500                 505                 510

Leu Leu Pro Val Leu Cys Gln Ala His Gly Leu Thr Pro Gln Gln Val
        515                 520                 525

Val Ala Ile Ala Ser Asn Gly Gly Lys Gln Ala Leu Glu Thr Val
    530                 535                 540

Gln Arg Leu Leu Pro Val Leu Cys Gln Ala His Gly Leu Thr Pro Glu
545                 550                 555                 560

Gln Val Val Ala Ile Ala Ser His Asp Gly Gly Lys Gln Ala Leu Glu
                565                 570                 575

Thr Val Gln Arg Leu Leu Pro Val Leu Cys Gln Ala His Gly Leu Thr
            580                 585                 590

Pro Glu Gln Val Val Ala Ile Ala Ser Asn Ile Gly Gly Lys Gln Ala
```

```
                    595                 600                 605
Leu Glu Thr Val Gln Ala Leu Leu Pro Val Leu Cys Gln Ala His Gly
610                 615                 620

Leu Thr Pro Glu Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                    645                 650                 655

His Gly Leu Thr Pro Gln Gln Val Val Ala Ile Ala Ser Asn Gly Gly
                    660                 665                 670

Gly Lys Gln Ala Leu Glu Thr Val Gln Arg Leu Leu Pro Val Leu Cys
                675                 680                 685

Gln Ala His Gly Leu Thr Pro Gln Gln Val Val Ala Ile Ala Ser Asn
690                 695                 700

Asn Gly Gly Lys Gln Ala Leu Glu Thr Val Gln Arg Leu Leu Pro Val
705                 710                 715                 720

Leu Cys Gln Ala His Gly Leu Thr Pro Gln Gln Val Val Ala Ile Ala
                    725                 730                 735

Ser Asn Gly Gly Gly Lys Gln Ala Leu Glu Thr Val Gln Arg Leu Leu
                740                 745                 750

Pro Val Leu Cys Gln Ala His Gly Leu Thr Pro Glu Gln Val Val Ala
            755                 760                 765

Ile Ala Ser His Asp Gly Gly Lys Gln Ala Leu Glu Thr Val Gln Arg
770                 775                 780

Leu Leu Pro Val Leu Cys Gln Ala His Gly Leu Thr Pro Glu Gln Val
785                 790                 795                 800

Val Ala Ile Ala Ser Asn Ile Gly Gly Lys Gln Ala Leu Glu Thr Val
                    805                 810                 815

Gln Ala Leu Leu Pro Val Leu Cys Gln Ala His Gly Leu Thr Pro Gln
                820                 825                 830

Gln Val Val Ala Ile Ala Ser Asn Gly Gly Gly Arg Pro Ala Leu Glu
            835                 840                 845

Ser Ile Val Ala Gln Leu Ser Arg Pro Asp Pro Ser Gly Ser Gly Ser
850                 855                 860

Gly Gly Asp Pro Ile Ser Arg Ser Gln Leu Val Lys Ser Glu Leu Glu
865                 870                 875                 880

Glu Lys Lys Ser Glu Leu Arg His Lys Leu Lys Tyr Val Pro His Glu
                    885                 890                 895

Tyr Ile Glu Leu Ile Glu Ile Ala Arg Asn Ser Thr Gln Asp Arg Ile
                900                 905                 910

Leu Glu Met Lys Val Met Glu Phe Phe Met Lys Val Tyr Gly Tyr Arg
            915                 920                 925

Gly Lys His Leu Gly Gly Ser Arg Lys Pro Asp Gly Ala Ile Tyr Thr
        930                 935                 940

Val Gly Ser Pro Ile Asp Tyr Gly Val Ile Val Asp Thr Lys Ala Tyr
945                 950                 955                 960

Ser Gly Gly Tyr Asn Leu Pro Ile Gly Gln Ala Asp Glu Met Gln Arg
                    965                 970                 975

Tyr Val Glu Glu Asn Gln Thr Arg Asn Lys His Ile Asn Pro Asn Glu
                980                 985                 990

Trp Trp Lys Val Tyr Pro Ser Ser Val Thr Glu Phe Lys Phe Leu Phe
            995                 1000                1005

Val Ser Gly His Phe Lys Gly Asn Tyr Lys Ala Gln Leu Thr Arg Leu
        1010                1015                1020
```

```
Asn His Ile Thr Asn Cys Asn Gly Ala Val Leu Ser Val Glu Glu Leu
1025                1030                1035                1040

Leu Ile Gly Gly Glu Met Ile Lys Ala Gly Thr Leu Thr Leu Glu Glu
                1045                1050                1055

Val Arg Arg Lys Phe Asn Asn Gly Glu Ile Asn Phe Ala Ala Asp
    1060                1065                1070

<210> SEQ ID NO 49
<211> LENGTH: 1070
<212> TYPE: PRT
<213> ORGANISM: artificial sequence
<220> FEATURE:
<223> OTHER INFORMATION: TALEN XPCT3R-N*

<400> SEQUENCE: 49

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Pro Ile Arg Ser Arg Thr Pro Ser Pro Ala Arg Glu Leu Leu Pro Gly
        35                  40                  45

Pro Gln Pro Asp Gly Val Gln Pro Thr Ala Asp Arg Gly Val Ser Pro
    50                  55                  60

Pro Ala Gly Gly Pro Leu Asp Gly Leu Pro Ala Arg Arg Thr Met Ser
65                  70                  75                  80

Arg Thr Arg Leu Pro Ser Pro Pro Ala Pro Ser Pro Ala Phe Ser Ala
                85                  90                  95

Gly Ser Phe Ser Asp Leu Leu Arg Gln Phe Asp Pro Ser Leu Phe Asn
            100                 105                 110

Thr Ser Leu Phe Asp Ser Leu Pro Pro Phe Gly Ala His His Thr Glu
        115                 120                 125

Ala Ala Thr Gly Glu Trp Asp Glu Val Gln Ser Gly Leu Arg Ala Ala
    130                 135                 140

Asp Ala Pro Pro Pro Thr Met Arg Val Ala Val Thr Ala Ala Arg Pro
145                 150                 155                 160

Pro Arg Ala Lys Pro Ala Pro Arg Arg Ala Ala Gln Pro Ser Asp Ala
                165                 170                 175

Ala Ser Pro Ala Ala Gln Val Asp Leu Arg Thr Leu Gly Tyr Ser Gln
            180                 185                 190

Gln Gln Gln Glu Lys Ile Lys Pro Lys Val Arg Ser Thr Val Ala Gln
        195                 200                 205

His His Glu Ala Leu Val Gly His Gly Phe Thr His Ala His Ile Val
    210                 215                 220

Ala Leu Ser Gln His Pro Ala Ala Leu Gly Thr Val Ala Val Lys Tyr
225                 230                 235                 240

Gln Asp Met Ile Ala Ala Leu Pro Glu Ala Thr His Glu Ala Ile Val
                245                 250                 255

Gly Val Gly Lys Gln Trp Ser Gly Ala Arg Ala Leu Glu Ala Leu Leu
            260                 265                 270

Thr Val Ala Gly Glu Leu Arg Gly Pro Pro Leu Gln Leu Asp Thr Gly
        275                 280                 285

Gln Leu Leu Lys Ile Ala Lys Arg Gly Gly Val Thr Ala Val Glu Ala
    290                 295                 300

Val His Ala Trp Arg Asn Ala Leu Thr Gly Ala Pro Leu Asn Leu Thr
305                 310                 315                 320
```

```
Pro Gln Gln Val Val Ala Ile Ala Ser Asn Gly Gly Lys Gln Ala
            325                 330                 335

Leu Glu Thr Val Gln Arg Leu Leu Pro Val Leu Cys Gln Ala His Gly
            340                 345                 350

Leu Thr Pro Gln Gln Val Val Ala Ile Ala Ser Asn Asn Gly Gly Lys
            355                 360                 365

Gln Ala Leu Glu Thr Val Gln Arg Leu Leu Pro Val Leu Cys Gln Ala
        370                 375                 380

His Gly Leu Thr Pro Glu Gln Val Val Ala Ile Ala Ser Asn Gly Gly
385                 390                 395                 400

Lys Gln Ala Leu Glu Thr Val Gln Arg Leu Leu Pro Val Leu Cys Gln
            405                 410                 415

Ala His Gly Leu Thr Pro Gln Gln Val Val Ala Ile Ala Ser Asn Asn
            420                 425                 430

Gly Gly Lys Gln Ala Leu Glu Thr Val Gln Arg Leu Leu Pro Val Leu
            435                 440                 445

Cys Gln Ala His Gly Leu Thr Pro Gln Gln Val Val Ala Ile Ala Ser
        450                 455                 460

Asn Asn Gly Gly Lys Gln Ala Leu Glu Thr Val Gln Arg Leu Leu Pro
465                 470                 475                 480

Val Leu Cys Gln Ala His Gly Leu Thr Pro Gln Gln Val Val Ala Ile
            485                 490                 495

Ala Ser Asn Asn Gly Gly Lys Gln Ala Leu Glu Thr Val Gln Arg Leu
            500                 505                 510

Leu Pro Val Leu Cys Gln Ala His Gly Leu Thr Pro Gln Gln Val Val
            515                 520                 525

Ala Ile Ala Ser Asn Gly Gly Gly Lys Gln Ala Leu Glu Thr Val Gln
            530                 535                 540

Arg Leu Leu Pro Val Leu Cys Gln Ala His Gly Leu Thr Pro Glu Gln
545                 550                 555                 560

Val Val Ala Ile Ala Ser His Asp Gly Gly Lys Gln Ala Leu Glu Thr
                565                 570                 575

Val Gln Arg Leu Leu Pro Val Leu Cys Gln Ala His Gly Leu Thr Pro
            580                 585                 590

Glu Gln Val Val Ala Ile Ala Ser Asn Ile Gly Gly Lys Gln Ala Leu
            595                 600                 605

Glu Thr Val Gln Ala Leu Leu Pro Val Leu Cys Gln Ala His Gly Leu
            610                 615                 620

Thr Pro Glu Gln Val Val Ala Ile Ala Ser His Asp Gly Gly Lys Gln
625                 630                 635                 640

Ala Leu Glu Thr Val Gln Arg Leu Leu Pro Val Leu Cys Gln Ala His
            645                 650                 655

Gly Leu Thr Pro Gln Gln Val Val Ala Ile Ala Ser Asn Gly Gly Gly
            660                 665                 670

Lys Gln Ala Leu Glu Thr Val Gln Arg Leu Leu Pro Val Leu Cys Gln
            675                 680                 685

Ala His Gly Leu Thr Pro Gln Gln Val Val Ala Ile Ala Ser Asn Asn
            690                 695                 700

Gly Gly Lys Gln Ala Leu Glu Thr Val Gln Arg Leu Leu Pro Val Leu
705                 710                 715                 720

Cys Gln Ala His Gly Leu Thr Pro Gln Gln Val Val Ala Ile Ala Ser
            725                 730                 735
```

Asn Gly Gly Gly Lys Gln Ala Leu Glu Thr Val Gln Arg Leu Leu Pro
                740                 745                 750

Val Leu Cys Gln Ala His Gly Leu Thr Pro Glu Gln Val Val Ala Ile
            755                 760                 765

Ala Ser His Asp Gly Lys Gln Ala Leu Glu Thr Val Gln Arg Leu
        770                 775                 780

Leu Pro Val Leu Cys Gln Ala His Gly Leu Thr Pro Glu Gln Val Val
785                 790                 795                 800

Ala Ile Ala Ser Asn Ile Gly Lys Gln Ala Leu Glu Thr Val Gln
                805                 810                 815

Ala Leu Leu Pro Val Leu Cys Gln Ala His Gly Leu Thr Pro Gln Gln
            820                 825                 830

Val Val Ala Ile Ala Ser Asn Gly Gly Gly Arg Pro Ala Leu Glu Ser
            835                 840                 845

Ile Val Ala Gln Leu Ser Arg Pro Asp Pro Ser Gly Ser Gly Ser Gly
            850                 855                 860

Gly Asp Pro Ile Ser Arg Ser Gln Leu Val Lys Ser Glu Leu Glu Glu
865                 870                 875                 880

Lys Lys Ser Glu Leu Arg His Lys Leu Lys Tyr Val Pro His Glu Tyr
                885                 890                 895

Ile Glu Leu Ile Glu Ile Ala Arg Asn Ser Thr Gln Asp Arg Ile Leu
                900                 905                 910

Glu Met Lys Val Met Glu Phe Phe Met Lys Val Tyr Gly Tyr Arg Gly
                915                 920                 925

Lys His Leu Gly Gly Ser Arg Lys Pro Asp Gly Ala Ile Tyr Thr Val
            930                 935                 940

Gly Ser Pro Ile Asp Tyr Gly Val Ile Val Asp Thr Lys Ala Tyr Ser
945                 950                 955                 960

Gly Gly Tyr Asn Leu Pro Ile Gly Gln Ala Asp Glu Met Gln Arg Tyr
                965                 970                 975

Val Glu Glu Asn Gln Thr Arg Asn Lys His Ile Asn Pro Asn Glu Trp
            980                 985                 990

Trp Lys Val Tyr Pro Ser Ser Val Thr Glu Phe Lys Phe Leu Phe Val
            995                 1000                1005

Ser Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu Leu
1025                1030                1035                1040

Ile Gly Gly Glu Met Ile Lys Ala Gly Thr Leu Thr Leu Glu Glu Val
                1045                1050                1055

Arg Arg Lys Phe Asn Asn Gly Glu Ile Asn Phe Ala Ala Asp
            1060                1065                1070

<210> SEQ ID NO 50
<211> LENGTH: 45
<212> TYPE: DNA
<213> ORGANISM: artificial sequence
<220> FEATURE:
<223> OTHER INFORMATION: xpc2 locus

<400> SEQUENCE: 50
tgggtccgag atgtcacaca gaggtacgac ccagtctgga tgaca           45

<210> SEQ ID NO 51
<211> LENGTH: 45
<212> TYPE: DNA

<213> ORGANISM: artificial sequence
<220> FEATURE:
<223> OTHER INFORMATION: xpc3 locus

<400> SEQUENCE: 51

```
tgtcacacag aggtacgacc cagtctggat gacagtgacc cgcaa            45
```

<210> SEQ ID NO 52
<211> LENGTH: 3198
<212> TYPE: DNA
<213> ORGANISM: artificial sequence
<220> FEATURE:
<223> OTHER INFORMATION: TALEN XPCT1L-T*

<400> SEQUENCE: 52

```
atgggcgatc ctaaaaagaa acgtaaggtc atcgattacc catacgatgt tccagattac     60
gctatcgata tcgccgaccc cattcgttcg cgcacaccaa gtcctgcccg cgagcttctg    120
cccggacccc aacccgatgg ggttcagccg actgcagatc gtggggtgtc tccgcctgcc    180
ggcggccccc tggatggctt gccggctcgg cggacgatgt cccggacccg gctgccatct    240
cccctgccc cctcacctgc gttctcggcg ggcagcttca gtgacctgtt acgtcagttc    300
gatccgtcac ttttaatac atcgctttt gattcattgc ctcccttcgg cgctcaccat    360
acagaggctg ccacaggcga gtgggatgag gtgcaatcgg gtctgcgggc agccgacgcc    420
cccccaccca ccatgcgcgt ggctgtcact gccgcgcggc ccccgcgcgc caagccggcg    480
ccgcgacgac gtgctgcgca accctccgac gcttcgccgg cggcgcaggt ggatctacgc    540
acgctcggct acagccagca gcaacaggag aagatcaaac cgaaggttcg ttcgacagtg    600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca acagtggtc cggcgcacgc    780
gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga cccctgagca ggtggtggct    960
attgcctctc acgatggcgg gaaacaggcc ctggaaacag tgcagcggct cctgccgtg   1020
ctgtgccaag cccacggcct cacaccagaa caggtggtcg ccatcgcctc cacaggcggc   1080
aaacaagccc tggagactgt gcagcgcctg ttgcccgtcc tgtgccaggc tcacgggctg   1140
actcctcagc aagtcgtggc cattgccagc aataacggag ggaagcaggc actggagaca   1200
gtccagaggc tgctgcctgt cctctgtcag gcccacgggc tcactcccga caagtggtc   1260
gcaatcgcca gcaacatcgg gggaaagcag gcttttggaaa ccgtgcaggc cctgctgccc   1320
gtgttgtgtc aggcacacgg cttgaccccca gcaagtgg tggccatcgc cagtaacaac   1380
ggaggcaaac aggctcttga gacagtgcaa agactcctgc cagtcctctg ccaggcacat   1440
gggctgaccc ccgagcaggt cgtggctatc gcctccaaca ttgggggaaa acaggcattg   1500
gagaccgtcc aggcccttct gcctgtgctt tgtcaagcac acggactgac ccccaacaa   1560
gtcgtcgcca ttgcctcaaa cggggcggg aagcaagccc ttgaaacagt ccagcggctg   1620
ttgccagtgc tctgccaagc tcacgggttg acaccccaac aggtcgtcgc aattgcttcc   1680
aacaacggcg gcaagcaggc cctcgaaacc gtcagagac tcctcccgt cttgtgtcag   1740
gctcatggcc tgaccccca gcaggtggtc gctattgcca gcaatggggg gggcaaacag   1800
gccctggaga cagtgcagag gctcctccca gtgctctgtc aggcacatgg gctgacacca   1860
```

```
gagcaagtgg tcgccatcgc cagccatgat ggcgggaaac aggcactgga gaccgtccag    1920
cggttgcttc ctgtcctttg ccaagcacat ggcttgacac ctgagcaggt cgtcgccatt    1980
gcttccaaca ttggcggcaa gcaagccctg gaaaccgtcc aggccctgct ccccgtgctg    2040
tgccaggccc acgggctcac acccgaacag gtcgtggcta tcgccagtca cgatggaggc    2100
aaacaagctc tggaaacagt ccagagactg ctgcccgtcc tctgccaggc tcacgggttg    2160
actcccgagc aagtcgtcgc aatcgcaagc aacatcggag ggaagcaagc actggaaact    2220
gtccaggcac tcctgcctgt cctgtgccaa gcccacggac tgaccccga caagtcgtg     2280 gccattgcct cacatgacgg gggaaagcag gctcttgaga cagtccagcg cctgctccca    2340
gtcctgtgtc aagcacacgg cttgaccct gaacaagtgg tggcaatcgc ttctaacatt    2400
gggggcaagc aggcccttga gactgtccaa gcactgctgc cagtgctttg ccaggcacac    2460
gggctgactc cacaacaggt ggtggccatc gctagcaacg gaggcgggag ccagccctc    2520 gagagcattg ttgcccagtt atctcgccct gatccgagtg gcagcggaag tggcggggat    2580
cctatcagcc gttcccagct ggtgaagtcc gagctggagg agaagaaatc cgagttgagg    2640
cacaagctga gtacgtgcc ccacgagtac atcgagctga tcgagatcgc ccggaacagc    2700
acccaggacc gtatcctgga tgaaggtg atggagttct tcatgaaggt gtacggctac    2760
aggggcaagc acctgggcgg ctccaggaag cccgacggcg ccatctacac cgtgggctcc    2820
cccatcgact acggcgtgat cgtggacacc aaggcctact ccggcggcta caacctgccc    2880
atcggccagg ccgacgaaat gcagaggtac gtggaggaga accagaccag gaacaagcac    2940 atcaaccca cgagtggtg gaaggtgtac ccctccagcg tgaccgagtt caagttcctg    3000
ttcgtgtccg ccacttcaa gggcaactac aaggcccagc tgaccaggct gaaccacatc    3060
accaactgca acggcgccgt gctgtccgtg gaggagctcc tgatcggcgg cgagatgatc    3120
aaggccggca ccctgacct ggaggaggtg aggaggaagt caacaacgg cgagatcaac    3180 ttcgcggccg actgataa                                                 3198
```

<210> SEQ ID NO 53
<211> LENGTH: 3198
<212> TYPE: DNA
<213> ORGANISM: artificial sequence
<220> FEATURE:
<223> OTHER INFORMATION: TALEN XPCT1L-Q*

<400> SEQUENCE: 53

```
atgggcgatc taaaaagaa acgtaaggtc atcgattacc catacgatgt tccagattac      60
gctatcgata tcgccgaccc cattcgttcg cgcacaccaa gtcctgcccg cgagcttctg     120 cccggaccc aacccgatgg ggttcagccg actgcagatc gtggggtgtc tccgcctgcc     180 ggcggcccc tggatggctt gccggctcgg cggacgatgt cccggacccg gctgccatct     240
ccccctgccc cctcacctgc gttctcggcg ggcagcttca gtgacctgtt acgtcagttc     300
gatccgtcac tttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc cccgcgcgc caagccggcg     480 ccgcgacgac gtgctgcgca acctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
```

```
agccaacacc cggcagcgtt agggaccgtc gctgtcaagt atcaggacat gatcgcagcg    720
ttgccagagg cgacacacga agcgatcgtt ggcgtcggca aacagtggtc cggcgcacgc    780
gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga cccctgagca ggtggtggct    960
attgcctctc acgatggcgg gaaacaggcc ctggaaacag tgcagcggct cctgcccgtg   1020
ctgtgccaag cccacggcct cacaccagaa caggtggtcg ccatcgcctc caaggcggc    1080
aaacaagccc tggagactgt gcagcgcctg ttgcccgtcc tgtgccaggc tcacgggctg   1140
actcctcagc aagtcgtggc cattgccagc aataacggag ggaagcaggc actggagaca   1200
gtccagagcg tgctgcctgt cctctgtcag gcccacgggc tcactcccga caagtggtc   1260
gcaatcgcca gcaacatcgg gggaaagcag gctttggaaa ccgtgcaggc cctgctgccc   1320
gtgttgtgtc aggcacacgg cttgaccccca gcaagtgg tggccatcgc cagtaacaac   1380
ggaggcaaac aggctcttga gacagtgcaa agactcctgc cagtcctctg ccaggcacat   1440
gggctgaccc ccgagcaggt cgtggctatc gcctccaaca ttgggggaaa acaggcattg   1500
gagaccgtcc aggcccttct gcctgtgctt tgtcaagcac acggactgac cccccaacaa   1560
gtcgtcgcca ttgcctcaaa cggggcggg aagcaagccc ttgaaacagt ccagcggctg   1620
ttgccagtgc tctgccaagc tcacggggttg acacccaac aggtcgtcgc aattgcttcc   1680
aacaacggcg gcaagcaggc cctcgaaacc gtccagagac tcctcccgt cttgtgtcag   1740
gctcatggcc tgacccccca gcaggtggtc gctattgcca gcaatggggg gggcaaacag   1800
gccctggaga cagtgcagag gctcctccca gtgctctgtc aggcacatgg gctgacacca   1860
gagcaagtgg tcgccatcgc cagccatgat ggcgggaaac aggcactgga gaccgtccag   1920
cggttgcttc ctgtcctttg ccaagcacat ggcttgacac ctgagcaggt cgtcgccatt   1980
gcttccaaca ttggcggcaa gcaagccctg gaaaccgtcc aggccctgct ccccgtgctg   2040
tgccaggccc acgggctcac acccgaacag gtcgtggcta tcgccagtca cgatggaggc   2100
aaacaagctc tggaaacagt ccagagactg ctgcccgtcc tctgccaggc tcacggggttg   2160
actcccgagc aagtcgtcgc aatcgcaagc aacatcggag ggaagcaagc actggaaact   2220
gtccaggcac tcctgcctgt cctgtgccaa gcccacggac tgacccccga caagtcgtg   2280
gccattgcct cacatgacgg gggaaagcag gctcttgaga cagtccagcg cctgctccca   2340
gtcctgtgtc aagcacacgg cttgaccccct gaacaagtgg tggcaatcgc ttctaacatt   2400
gggggcaagc aggcccttga gactgtccaa gcactgctgc cagtgctttg ccaggcacac   2460
gggctgactc cacaacaggt ggtggccatc gctagcaacg gaggcgggag gccagccctc   2520
gagagcattg ttgcccagtt atctcgccct gatccgagtg gcagcggaag tggcggggat   2580
cctatcagcc gttcccagct ggtgaagtcc gagctggagg agaagaaatc cgagttgagg   2640
cacaagctga agtacgtgcc ccacgagtac atcgagctga tcgagatcgc ccggaacagc   2700
acccaggacc gtatcctgga gatgaaggtg atggagttct tcatgaaggt gtacggctac   2760
aggggcaagc acctgggcgg ctccaggaag cccgacggcg ccatctacac cgtgggctcc   2820
cccatcgact acggcgtgat cgtggacacc aaggcctact ccggcggcta caacctgccc   2880
atcggccagg ccgacgaaat gcagaggtac gtggaggaga accagaccag gaacaagcac   2940
atcaaccccca acgagtggtg gaaggtgtac ccctccagcg tgaccgagtt caagttcctg   3000
ttcgtgtccg gccacttcaa gggcaactac aaggcccagc tgaccaggct gaaccacatc   3060
```

| | | |
|---|---|---|
| accaactgca acggcgccgt gctgtccgtg gaggagctcc tgatcggcgg cgagatgatc | 3120 |
| aaggccggca ccctgaccct ggaggaggtg aggaggaagt tcaacaacgg cgagatcaac | 3180 |
| ttcgcggccg actgataa | 3198 |

<210> SEQ ID NO 54
<211> LENGTH: 3201
<212> TYPE: DNA
<213> ORGANISM: artificial sequence
<220> FEATURE:
<223> OTHER INFORMATION: TALEN XPCT1L-HG

<400> SEQUENCE: 54

| | | |
|---|---|---|
| atgggcgatc ctaaaaagaa acgtaaggtc atcgattacc catacgatgt tccagattac | 60 |
| gctatcgata tcgccgaccc cattcgttcg cgcacaccaa gtcctgcccg cgagcttctg | 120 |
| cccggacccc aacccgatgg ggttcagccg actgcagatc gtggggtgtc tccgcctgcc | 180 |
| ggcggccccc tggatggctt gccggctcgg cggacgatgt cccggacccg gctgccatct | 240 |
| cccctgccc cctcacctgc gttctcggcg ggcagcttca gtgacctgtt acgtcagttc | 300 |
| gatccgtcac tttttaatac atcgcttttt gattcattgc ctcccttcgg cgctcaccat | 360 |
| acagaggctg ccacaggcga gtgggatgag gtgcaatcgg gtctgcgggc agccgacgcc | 420 |
| cccccaccca ccatgcgcgt ggctgtcact gccgcgcggc cccgcgcgc caagccggcg | 480 |
| ccgcgacgac gtgctgcgca accctccgac gcttcgccgg cggcgcaggt ggatctacgc | 540 |
| acgctcggct acagccagca gcaacaggag aagatcaaac cgaaggttcg ttcgacagtg | 600 |
| gcgcagcacc acgaggcact ggtcggccac gggtttacac acgcgcacat cgttgcgtta | 660 |
| agccaacacc cggcagcgtt agggaccgtc gctgtcaagt atcaggacat gatcgcagcg | 720 |
| ttgccagagg cgacacacga agcgatcgtt ggcgtcggca acagtggtc cggcgcacgc | 780 |
| gctctggagg ccttgctcac ggtggcggga gagttgagag gtccaccgtt acagttggac | 840 |
| acaggccaac ttctcaagat tgcaaaacgt ggcggcgtga ccgcagtgga ggcagtgcat | 900 |
| gcatggcgca atgcactgac gggtgccccg ctcaacctga ccccagaaca ggtggtggct | 960 |
| atcgcctcac acgatggggg aaaacaggcc ctggagacag tgcagcggct gctccctgtg | 1020 |
| ctttgccagg ctcacggact gaccccgag caggtggtcg caatcgccag tcacgggggc | 1080 |
| ggaaaacaag ccctggaaac agtccagcgc ctcctgcctg tgctgtgtca ggcccacggc | 1140 |
| ttgacccac agcaggtcgt cgccattgct ccaacaatg gcggaaagca ggctctggag | 1200 |
| actgtgcaga gactgctccc cgtgctgtgc aggcacacg gctgacacc tgagcaagtg | 1260 |
| gtcgccatcg caagcaacat tggcggcaag caagcccttg agacagtcca agctctgctg | 1320 |
| ccagtgcttt gtcaggctca tgggctcacc ccccagcaag tcgtggccat tgcctctaac | 1380 |
| aacggcggga gcaggccctt ggagaccgtc cagagactcc tgcccgtgct ctgccaagca | 1440 |
| catgggttga ctccagaaca ggtggtcgca attgccagta acatcggcgg aagcaagcg | 1500 |
| ttggaaactg tgcaagctct cctccccgtg ctgtgtcagg cacacggcct cacacctcaa | 1560 |
| caagtcgtgg caatcgcctc caacgggggg gggaagcagg ccctggagac agtccagagg | 1620 |
| ttgctgcccg tcctttgcca ggcccacggc ctgacccca acaagtggt ggctatcgca | 1680 |
| agtaacaatg gcgggaaaca agccctcgag acagtgcagc ggctcttgcc tgtcttgtgt | 1740 |
| caagcccacg gactgactcc ccaacaggtc gtggccatcg cctctaacgg cggggggcaag | 1800 |
| caagcactcg agactgtcca gcgcctcctg cccgtgcttt gccaagctca cggccttacc | 1860 |

-continued

```
cctgagcaag tggtcgctat tgccagccat gatggcggaa agcaagccct ggaaaccgtg    1920
cagaggctgc tgccagtgct gtgccaggct catgggctga cacccgagca ggtggtggcc    1980
attgcctcaa atattggagg gaaacaggcc ttggagactg tgcaggcact cctcccagtg    2040
ctgtgtcagg ctcatggcct gactcccgag caagtcgtgg ccatcgcaag ccacgacggg    2100
gggaagcaag cactggagac cgtccagaga ctgctgcccg tgctctgtca agctcacgga    2160
ctgacaccag aacaggtggt cgccattgct ccaacattg gcggcaagca agccctggag    2220
acagtgcaag ctctcctgcc tgtgttgtgc caggctcacg gcctgacccc tgagcaggtc    2280
gtggcaatcg cctcccatga cggggggaaaa caggccctcg agaccgtgca gaggctgctt    2340
cctgtccttt gccaggccca cggcctcaca cccgaacagg tcgtcgctat tgccagcaat    2400
atcgggggca agcaggctct cgagacagtc caggccttgc tcccagtgct gtgccaagcc    2460
cacgggctta ctccacagca ggtggtggct atcgccagca acggggagg gcggccagct    2520 ctggagagca ttgttgccca gttatctcgc cctgatccga gtggcagcgg aagtggcggg    2580
gatcctatca gccgttccca gctggtgaag tccgagctgg aggagaagaa atccgagttg    2640
aggcacaagc tgaagtacgt gccccacgag tacatcgagc tgatcgagat cgcccggaac    2700
agcacccagg accgtatcct ggagatgaag gtgatggagt tcttcatgaa ggtgtacggc    2760
tacaggggca agcacctggg cggctccagg aagcccgacg cgccatcta ccgtgggc    2820 tcccccatcg actacggcgt gatcgtggac accaaggcct actccggcgg ctacaacctg    2880
cccatcggcc aggccgacga aatgcagagg tacgtggagg agaaccagac caggaacaag    2940
cacatcaacc ccaacgagtg gtggaaggtg taccctcca gcgtgaccga gttcaagttc    3000
ctgttcgtgt ccggccactt caagggcaac tacaaggccc agctgaccag gctgaaccac    3060
atcaccaact gcaacggcgc cgtgctgtcc gtggaggagc tcctgatcgg cggcgagatg    3120
atcaaggccg gcaccctgac cctggaggag gtgaggagga agttcaacaa cggcgagatc    3180
aacttcgcgg ccgactgata a    3201
```

<210> SEQ ID NO 55
<211> LENGTH: 1064
<212> TYPE: PRT
<213> ORGANISM: artificial sequence
<220> FEATURE:
<223> OTHER INFORMATION: TALEN XPCT1L-T*

<400> SEQUENCE: 55

```
Met Gly Asp Pro Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125
```

```
Asp Glu Val Gln Ser Gly Leu Arg Ala Ala Asp Ala Pro Pro Thr
    130                 135                 140

Met Arg Val Ala Val Thr Ala Ala Arg Pro Pro Arg Ala Lys Pro Ala
145                     150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
            275                 280                 285

Lys Arg Gly Gly Val Thr Ala Val Glu Ala Val His Ala Trp Arg Asn
        290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Thr Gly Gly Lys Gln Ala Leu Glu Thr Val Gln
        355                 360                 365

Arg Leu Leu Pro Val Leu Cys Gln Ala His Gly Leu Thr Pro Gln Gln
        370                 375                 380

Val Val Ala Ile Ala Ser Asn Asn Gly Gly Lys Gln Ala Leu Glu Thr
385                 390                 395                 400

Val Gln Arg Leu Leu Pro Val Leu Cys Gln Ala His Gly Leu Thr Pro
                405                 410                 415

Glu Gln Val Val Ala Ile Ala Ser Asn Ile Gly Gly Lys Gln Ala Leu
                420                 425                 430

Glu Thr Val Gln Ala Leu Leu Pro Val Leu Cys Gln Ala His Gly Leu
        435                 440                 445

Thr Pro Gln Gln Val Val Ala Ile Ala Ser Asn Gly Gly Lys Gln
    450                 455                 460

Ala Leu Glu Thr Val Gln Arg Leu Leu Pro Val Leu Cys Gln Ala His
465                 470                 475                 480

Gly Leu Thr Pro Glu Gln Val Val Ala Ile Ala Ser Asn Ile Gly Gly
                485                 490                 495

Lys Gln Ala Leu Glu Thr Val Gln Ala Leu Leu Pro Val Leu Cys Gln
            500                 505                 510

Ala His Gly Leu Thr Pro Gln Val Val Ala Ile Ala Ser Asn Gly
        515                 520                 525

Gly Gly Lys Gln Ala Leu Glu Thr Val Gln Arg Leu Leu Pro Val Leu
        530                 535                 540
```

-continued

Cys Gln Ala His Gly Leu Thr Pro Gln Gln Val Val Ala Ile Ala Ser
545                 550                 555                 560

Asn Asn Gly Gly Lys Gln Ala Leu Glu Thr Val Gln Arg Leu Leu Pro
            565                 570                 575

Val Leu Cys Gln Ala His Gly Leu Thr Pro Gln Gln Val Val Ala Ile
                580                 585                 590

Ala Ser Asn Gly Gly Gly Lys Gln Ala Leu Glu Thr Val Gln Arg Leu
        595                 600                 605

Leu Pro Val Leu Cys Gln Ala His Gly Leu Thr Pro Glu Gln Val Val
    610                 615                 620

Ala Ile Ala Ser His Asp Gly Gly Lys Gln Ala Leu Glu Thr Val Gln
625                 630                 635                 640

Arg Leu Leu Pro Val Leu Cys Gln Ala His Gly Leu Thr Pro Glu Gln
            645                 650                 655

Val Val Ala Ile Ala Ser Asn Ile Gly Gly Lys Gln Ala Leu Glu Thr
                660                 665                 670

Val Gln Ala Leu Leu Pro Val Leu Cys Gln Ala His Gly Leu Thr Pro
        675                 680                 685

Glu Gln Val Val Ala Ile Ala Ser His Asp Gly Gly Lys Gln Ala Leu
    690                 695                 700

Glu Thr Val Gln Arg Leu Leu Pro Val Leu Cys Gln Ala His Gly Leu
705                 710                 715                 720

Thr Pro Glu Gln Val Val Ala Ile Ala Ser Asn Ile Gly Gly Lys Gln
            725                 730                 735

Ala Leu Glu Thr Val Gln Ala Leu Leu Pro Val Leu Cys Gln Ala His
                740                 745                 750

Gly Leu Thr Pro Glu Gln Val Val Ala Ile Ala Ser His Asp Gly Gly
        755                 760                 765

Lys Gln Ala Leu Glu Thr Val Gln Arg Leu Leu Pro Val Leu Cys Gln
    770                 775                 780

Ala His Gly Leu Thr Pro Glu Gln Val Val Ala Ile Ala Ser Asn Ile
785                 790                 795                 800

Gly Gly Lys Gln Ala Leu Glu Thr Val Gln Ala Leu Leu Pro Val Leu
            805                 810                 815

Cys Gln Ala His Gly Leu Thr Pro Gln Gln Val Val Ala Ile Ala Ser
                820                 825                 830

Asn Gly Gly Gly Arg Pro Ala Leu Glu Ser Ile Val Ala Gln Leu Ser
        835                 840                 845

Arg Pro Asp Pro Ser Gly Ser Gly Ser Gly Asp Pro Ile Ser Arg
850                 855                 860

Ser Gln Leu Val Lys Ser Glu Leu Glu Glu Lys Lys Ser Glu Leu Arg
865                 870                 875                 880

His Lys Leu Lys Tyr Val Pro His Glu Tyr Ile Glu Leu Ile Glu Ile
            885                 890                 895

Ala Arg Asn Ser Thr Gln Asp Arg Ile Leu Glu Met Lys Val Met Glu
                900                 905                 910

Phe Phe Met Lys Val Tyr Gly Tyr Arg Gly Lys His Leu Gly Gly Ser
        915                 920                 925

Arg Lys Pro Asp Gly Ala Ile Tyr Thr Val Gly Ser Pro Ile Asp Tyr
    930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr

-continued

```
                965                 970                 975
Arg Asn Lys His Ile Asn Pro Asn Glu Trp Trp Lys Val Tyr Pro Ser
                    980                 985                 990

Ser Val Thr Glu Phe Lys Phe Leu Phe Val Ser Gly His Phe Lys Gly
                995                1000                1005

Asn Tyr Lys Ala Gln Leu Thr Arg Leu Asn His Ile Thr Asn Cys Asn
           1010                1015                1020

Gly Ala Val Leu Ser Val Glu Leu Ile Gly Gly Glu Met Ile
1025                1030                1035                1040

Lys Ala Gly Thr Leu Thr Leu Glu Glu Val Arg Arg Lys Phe Asn Asn
                    1045                1050                1055

Gly Glu Ile Asn Phe Ala Ala Asp
                1060

<210> SEQ ID NO 56
<211> LENGTH: 1064
<212> TYPE: PRT
<213> ORGANISM: artificial sequence
<220> FEATURE:
<223> OTHER INFORMATION: TALEN XPCT1L-Q*

<400> SEQUENCE: 56

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125

Asp Glu Val Gln Ser Gly Leu Arg Ala Ala Asp Ala Pro Pro Pro Thr
        130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
                180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
        210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
```

```
                260                 265                 270
Arg Gly Pro Pro Leu Gln Leu Asp Thr Gly Gln Leu Leu Lys Ile Ala
            275                 280                 285
Lys Arg Gly Gly Val Thr Ala Val Glu Ala Val His Ala Trp Arg Asn
        290                 295                 300
Ala Leu Thr Gly Ala Pro Leu Asn Leu Thr Pro Glu Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Ala His Gly Leu Thr Pro Glu Gln Val
            340                 345                 350
Val Ala Ile Ala Ser Gln Gly Gly Lys Gln Ala Leu Glu Thr Val Gln
        355                 360                 365
Arg Leu Leu Pro Val Leu Cys Gln Ala His Gly Leu Thr Pro Gln Gln
    370                 375                 380
Val Val Ala Ile Ala Ser Asn Asn Gly Gly Lys Gln Ala Leu Glu Thr
385                 390                 395                 400
Val Gln Arg Leu Leu Pro Val Leu Cys Gln Ala His Gly Leu Thr Pro
                405                 410                 415
Glu Gln Val Val Ala Ile Ala Ser Asn Ile Gly Gly Lys Gln Ala Leu
            420                 425                 430
Glu Thr Val Gln Ala Leu Leu Pro Val Leu Cys Gln Ala His Gly Leu
        435                 440                 445
Thr Pro Gln Gln Val Val Ala Ile Ala Ser Asn Asn Gly Gly Lys Gln
    450                 455                 460
Ala Leu Glu Thr Val Gln Arg Leu Leu Pro Val Leu Cys Gln Ala His
465                 470                 475                 480
Gly Leu Thr Pro Glu Gln Val Val Ala Ile Ala Ser Asn Ile Gly Gly
                485                 490                 495
Lys Gln Ala Leu Glu Thr Val Gln Ala Leu Leu Pro Val Leu Cys Gln
            500                 505                 510
Ala His Gly Leu Thr Pro Gln Gln Val Val Ala Ile Ala Ser Asn Gly
        515                 520                 525
Gly Gly Lys Gln Ala Leu Glu Thr Val Gln Arg Leu Leu Pro Val Leu
    530                 535                 540
Cys Gln Ala His Gly Leu Thr Pro Gln Gln Val Val Ala Ile Ala Ser
545                 550                 555                 560
Asn Asn Gly Gly Lys Gln Ala Leu Glu Thr Val Gln Arg Leu Leu Pro
                565                 570                 575
Val Leu Cys Gln Ala His Gly Leu Thr Pro Gln Gln Val Val Ala Ile
            580                 585                 590
Ala Ser Asn Gly Gly Gly Lys Gln Ala Leu Glu Thr Val Gln Arg Leu
        595                 600                 605
Leu Pro Val Leu Cys Gln Ala His Gly Leu Thr Pro Glu Gln Val Val
    610                 615                 620
Ala Ile Ala Ser His Asp Gly Gly Lys Gln Ala Leu Glu Thr Val Gln
625                 630                 635                 640
Arg Leu Leu Pro Val Leu Cys Gln Ala His Gly Leu Thr Pro Glu Gln
                645                 650                 655
Val Val Ala Ile Ala Ser Asn Ile Gly Gly Lys Gln Ala Leu Glu Thr
            660                 665                 670
Val Gln Ala Leu Leu Pro Val Leu Cys Gln Ala His Gly Leu Thr Pro
        675                 680                 685
```

Glu Gln Val Val Ala Ile Ala Ser His Asp Gly Gly Lys Gln Ala Leu
    690                 695                 700

Glu Thr Val Gln Arg Leu Leu Pro Val Leu Cys Gln Ala His Gly Leu
705                 710                 715                 720

Thr Pro Glu Gln Val Val Ala Ile Ala Ser Asn Ile Gly Gly Lys Gln
                725                 730                 735

Ala Leu Glu Thr Val Gln Ala Leu Leu Pro Val Leu Cys Gln Ala His
            740                 745                 750

Gly Leu Thr Pro Glu Gln Val Val Ala Ile Ala Ser His Asp Gly Gly
        755                 760                 765

Lys Gln Ala Leu Glu Thr Val Gln Arg Leu Leu Pro Val Leu Cys Gln
770                 775                 780

Ala His Gly Leu Thr Pro Glu Gln Val Val Ala Ile Ala Ser Asn Ile
785                 790                 795                 800

Gly Gly Lys Gln Ala Leu Glu Thr Val Gln Ala Leu Leu Pro Val Leu
                805                 810                 815

Cys Gln Ala His Gly Leu Thr Pro Gln Gln Val Val Ala Ile Ala Ser
            820                 825                 830

Asn Gly Gly Arg Pro Ala Leu Glu Ser Ile Val Ala Gln Leu Ser
        835                 840                 845

Arg Pro Asp Pro Ser Gly Ser Gly Ser Gly Asp Pro Ile Ser Arg
850                 855                 860

Ser Gln Leu Val Lys Ser Glu Leu Glu Lys Lys Ser Glu Leu Arg
865                 870                 875                 880

His Lys Leu Lys Tyr Val Pro His Glu Tyr Ile Glu Leu Ile Glu Ile
                885                 890                 895

Ala Arg Asn Ser Thr Gln Asp Arg Ile Leu Glu Met Lys Val Met Glu
            900                 905                 910

Phe Phe Met Lys Val Tyr Gly Tyr Arg Gly Lys His Leu Gly Gly Ser
        915                 920                 925

Arg Lys Pro Asp Gly Ala Ile Tyr Thr Val Gly Ser Pro Ile Asp Tyr
930                 935                 940

Gly Val Ile Val Asp Thr Lys Ala Tyr Ser Gly Gly Tyr Asn Leu Pro
945                 950                 955                 960

Ile Gly Gln Ala Asp Glu Met Gln Arg Tyr Val Glu Glu Asn Gln Thr
                965                 970                 975

Arg Asn Lys His Ile Asn Pro Asn Glu Trp Trp Lys Val Tyr Pro Ser
            980                 985                 990

Ser Val Thr Glu Phe Lys Phe Leu Phe Val Ser Gly His Phe Lys Gly
        995                 1000                1005

Asn Tyr Lys Ala Gln Leu Thr Arg Leu Asn His Ile Thr Asn Cys Asn
1010                1015                1020

Gly Ala Val Leu Ser Val Glu Glu Leu Leu Ile Gly Gly Glu Met Ile
1025                1030                1035                1040

Lys Ala Gly Thr Leu Thr Leu Glu Glu Val Arg Arg Lys Phe Asn Asn
                1045                1050                1055

Gly Glu Ile Asn Phe Ala Ala Asp
            1060

<210> SEQ ID NO 57
<211> LENGTH: 1065
<212> TYPE: PRT
<213> ORGANISM: artificial sequence
<220> FEATURE:

<223> OTHER INFORMATION: TALEN XPCT1L-HG

<400> SEQUENCE: 57

```
Met Gly Asp Pro Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
            35                  40                  45

Gln Pro Thr Ala Asp Arg Gly Val Ser Pro Ala Gly Gly Pro Leu
        50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400
```

-continued

```
Thr Val Gln Arg Leu Leu Pro Val Leu Cys Gln Ala His Gly Leu Thr
            405                 410                 415
Pro Glu Gln Val Val Ala Ile Ala Ser Asn Ile Gly Gly Lys Gln Ala
            420                 425                 430
Leu Glu Thr Val Gln Ala Leu Leu Pro Val Leu Cys Gln Ala His Gly
            435                 440                 445
Leu Thr Pro Gln Gln Val Val Ala Ile Ala Ser Asn Asn Gly Gly Lys
450                 455                 460
Gln Ala Leu Glu Thr Val Gln Arg Leu Leu Pro Val Leu Cys Gln Ala
465                 470                 475                 480
His Gly Leu Thr Pro Glu Gln Val Val Ala Ile Ala Ser Asn Ile Gly
            485                 490                 495
Gly Lys Gln Ala Leu Glu Thr Val Gln Ala Leu Leu Pro Val Leu Cys
            500                 505                 510
Gln Ala His Gly Leu Thr Pro Gln Gln Val Val Ala Ile Ala Ser Asn
            515                 520                 525
Gly Gly Gly Lys Gln Ala Leu Glu Thr Val Gln Arg Leu Leu Pro Val
            530                 535                 540
Leu Cys Gln Ala His Gly Leu Thr Pro Gln Gln Val Val Ala Ile Ala
545                 550                 555                 560
Ser Asn Asn Gly Gly Lys Gln Ala Leu Glu Thr Val Gln Arg Leu Leu
            565                 570                 575
Pro Val Leu Cys Gln Ala His Gly Leu Thr Pro Gln Gln Val Val Ala
            580                 585                 590
Ile Ala Ser Asn Gly Gly Lys Gln Ala Leu Glu Thr Val Gln Arg
            595                 600                 605
Leu Leu Pro Val Leu Cys Gln Ala His Gly Leu Thr Pro Glu Gln Val
            610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Glu
            645                 650                 655
Gln Val Val Ala Ile Ala Ser Asn Ile Gly Gly Lys Gln Ala Leu Glu
            660                 665                 670
Thr Val Gln Ala Leu Leu Pro Val Leu Cys Gln Ala His Gly Leu Thr
            675                 680                 685
Pro Glu Gln Val Val Ala Ile Ala Ser His Asp Gly Gly Lys Gln Ala
            690                 695                 700
Leu Glu Thr Val Gln Arg Leu Leu Pro Val Leu Cys Gln Ala His Gly
705                 710                 715                 720
Leu Thr Pro Glu Gln Val Val Ala Ile Ala Ser Asn Ile Gly Gly Lys
            725                 730                 735
Gln Ala Leu Glu Thr Val Gln Ala Leu Leu Pro Val Leu Cys Gln Ala
            740                 745                 750
His Gly Leu Thr Pro Glu Gln Val Val Ala Ile Ala Ser His Asp Gly
            755                 760                 765
Gly Lys Gln Ala Leu Glu Thr Val Gln Arg Leu Leu Pro Val Leu Cys
            770                 775                 780
Gln Ala His Gly Leu Thr Pro Glu Gln Val Val Ala Ile Ala Ser Asn
785                 790                 795                 800
Ile Gly Gly Lys Gln Ala Leu Glu Thr Val Gln Ala Leu Leu Pro Val
            805                 810                 815
Leu Cys Gln Ala His Gly Leu Thr Pro Gln Gln Val Val Ala Ile Ala
```

-continued

```
                820                 825                 830
Ser Asn Gly Gly Gly Arg Pro Ala Leu Glu Ser Ile Val Ala Gln Leu
            835                 840                 845

Ser Arg Pro Asp Pro Ser Gly Ser Gly Ser Gly Gly Asp Pro Ile Ser
    850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
            965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
        1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
                1060                1065
```